United States Patent [19]
Getman et al.

[11] Patent Number: 5,985,870
[45] Date of Patent: *Nov. 16, 1999

[54] SULFONYLALKANOYLAMINO HYDROXYETHYLAMINO SULFONAMIDE RETROVIRAL PROTEASE INHIBITORS

[75] Inventors: Daniel P Getman, Chesterfield; Gary A. Decrescenzo, St. Peter; John N. Freskos, Clayton, all of Mo.; Michael L. Vazquez, Gurnee, Ill.; James A. Sikorski, Des Peres, Mo.; Balekudru Devadas, Chesterfield, Mo.; Srinivasan Nagarajan, Chesterfield, Mo.; Joseph J. McDonald, Ballwin, Mo.

[73] Assignee: G.D. Searle & Co., Chicago, Ill.

[*] Notice: This patent is subject to a terminal disclaimer.

[21] Appl. No.: 08/913,069

[22] PCT Filed: Mar. 7, 1996

[86] PCT No.: PCT/US96/02682

§ 371 Date: Dec. 19, 1997

§ 102(e) Date: Dec. 19, 1997

[87] PCT Pub. No.: WO96/28418

PCT Pub. Date: Sep. 19, 1996

Related U.S. Application Data

[63] Continuation-in-part of application No. 08/401,838, Mar. 10, 1995, abandoned.

[51] Int. Cl.$^6$ .................. A61K 31/36; A61K 31/415; C07D 317/62; C07D 277/62
[52] U.S. Cl. .................. 514/228.2; 514/367; 514/375; 514/464; 514/469; 544/135; 544/137; 546/196; 546/198; 548/178; 548/217; 548/517; 548/518; 549/434; 549/438; 549/467
[58] Field of Search .................. 514/228.2, 464, 514/367, 469, 375; 549/438, 467, 434; 548/178, 217, 517, 518; 546/196, 198; 544/135, 137

[56] References Cited

U.S. PATENT DOCUMENTS

| | | | |
|---|---|---|---|
| H725 | 1/1990 | Gordon | 548/533 |
| 4,450,164 | 5/1984 | Bristol et al. | 424/256 |
| 4,477,441 | 10/1984 | Boger et al. | 424/177 |
| 4,514,391 | 4/1985 | Gordon et al. | 514/2 |
| 4,548,926 | 10/1985 | Matsueda et al. | 514/19 |
| 4,595,407 | 6/1986 | Carter | 71/90 |
| 4,599,198 | 7/1986 | Hoover | 260/998.2 |
| 4,616,088 | 10/1986 | Ryono et al. | 546/336 |
| 4,634,465 | 1/1987 | Ehrenfreund et al. | 71/91 |
| 4,668,769 | 5/1987 | Hoover | 530/331 |
| 4,668,770 | 5/1987 | Boger et al. | 530/331 |
| 4,757,050 | 7/1988 | Natarajan et al. | 514/18 |
| 4,880,938 | 11/1989 | Freidinger | 548/492 |
| 4,963,530 | 10/1990 | Hemmi et al. | 514/19 |
| 4,977,277 | 12/1990 | Rosenberg et al. | 549/215 |
| 5,508,294 | 4/1996 | Vazquez et al. | 514/453 |
| 5,705,500 | 1/1998 | Getman et al. | 514/228.2 |
| 5,753,660 | 5/1998 | Sikorski et al. | 514/253 |
| 5,760,064 | 6/1998 | Vazquez et al. | 514/357 |

FOREIGN PATENT DOCUMENTS

| | | |
|---|---|---|
| 0 104 041 | 3/1984 | European Pat. Off. . |
| 0 114 993 | 8/1984 | European Pat. Off. . |
| 0 172 347 | 2/1986 | European Pat. Off. . |
| 0 223 437 | 5/1987 | European Pat. Off. . |
| 0 264 795 | 4/1988 | European Pat. Off. . |
| 0 342 541 | 5/1989 | European Pat. Off. . |
| 0 337 714 | 10/1989 | European Pat. Off. . |
| 0 346 847 | 12/1989 | European Pat. Off. . |
| 0 356 223 | 2/1990 | European Pat. Off. . |
| 0 389 898 | 10/1990 | European Pat. Off. . |
| 0 393 445 | 10/1990 | European Pat. Off. . |
| 0 393 457 | 10/1990 | European Pat. Off. . |
| 0 402 646 | 12/1990 | European Pat. Off. . |
| 0 468 641 | 1/1992 | European Pat. Off. . |
| 2184730 | 7/1987 | United Kingdom . |
| 2200115 | 7/1988 | United Kingdom . |
| 2209752 | 5/1989 | United Kingdom . |
| 84/03044 | 8/1984 | WIPO . |
| 92/08699 | 5/1992 | WIPO . |
| 93/13066 | 7/1993 | WIPO . |
| 94/04493 | 3/1994 | WIPO . |
| 94/08458 | 5/1994 | WIPO . |
| 94/10136 | 5/1994 | WIPO . |
| 95/06030 | 3/1995 | WIPO . |
| 95/33464 | 12/1995 | WIPO . |

OTHER PUBLICATIONS

International Search Report of PCT/US96/02682 dated Aug. 21, 1996.
Roberts et al., *Science*, 248, 358 (1990).
Erickson et al., *Science*, 249, 527 (1990).
Pearl et al., *Nature* 328 (1987).
Martin, *Drugs of the Future*, (1991), 16(3), 210–212.
Meek et al., *Nature*, 343:90–92, (1990).
McQuade et al., *Science*, 274, 454 (1990).
Rich et al., *Pept. Struct. Funct. Am. Pept. Sym.* 8th ed. pp. 511–520 (1983).
Rosenberg et al., *J. Med. Chem.*, 30, 1224–1228 (1987).
Fittkau, *J. Prakt. Chem.* 315, 1037 (1973).
Hirsh et al., *N. Eng. J. Med.*, 328, 1686 (1993).
E. E. Gilbert, "Recent Developments in Preparative Sulfonation and Sulfation," *Synthesis*, 3 (1969).
Mitsuya et al., *Proc. Natl. Acad. Sci. USA*, 83, 1911–15 (1986).
Silcox et al., *J. Heterocycl Chem.*, 4, 166–67 (1967).
Cabiddu et al., *Synthesis*, 797–798 (1976).
Ncube et al., *Tet. Lett*, 26, 2345–2348 (1978).
Ncube et al., *Tet. Lett*, 3, 255–256 (1977).
Cole et al., *Aust. J. Chem.*, 33, 675–80 (1980).

*Primary Examiner*—Fiona T. Powers
*Attorney, Agent, or Firm*—Banner & Witcoff, Ltd.

[57] ABSTRACT

Selected sulfonylalkanoylamino hydroxyethylamine sulfonamide compounds are effective as retroviral protease inhibitors, and in particular as inhibitors of HIV protease. The present invention relates to such retroviral protease inhibitors and, more particularly, relates to selected novel compounds, composition and method for inhibiting retroviral proteases, such as human immunodeficiency virus (HIV) protease, prophylactically preventing retroviral infection or the spread of a retrovirus, and treatment of a retroviral infection.

10 Claims, No Drawings

SULFONYLALKANOYLAMINO HYDROXYETHYLAMINO SULFONAMIDE RETROVIRAL PROTEASE INHIBITORS

RELATED CASE

This application is the national stage entry of PCT/US96/02682, filed Mar. 7, 1996, which is a continuation-in-part of application Ser. No. 08/401,438, filed Mar. 10, 1995, now abandoned.

BACKGROUND OF THE INVENTION

The present invention relates to retroviral protease inhibitors and, more particularly, relates to novel compounds, composition and method for inhibiting retroviral proteases, such as human immunodeficiency virus (HIV) protease. This invention, in particular, relates to sulfonylalkanoylamino hydroxyethylamine sulfonamide protease inhibitor compounds, composition and method for inhibiting retroviral proteases, prophylactically preventing retroviral infection or the spread of a retrovirus, and treatment of a retroviral infection, e.g., an HIV infection. The subject invention also relates to processes for making such compounds as well as to intermediates useful in such processes.

During the replication cycle of retroviruses, gag and gag-pol gene transcription products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease active site that processing of the gag precursor protein is prevented. Thus, attempts have been made to inhibit viral replication by Inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit specific processing of structural proteins and the release of retroviral protease itself. In this manner, retroviral replication proteases can be effectively inhibited.

Several classes of compounds have been proposed, particularly for inhibition of proteases, such as for inhibition of HIV protease. WO 92/08701, WO 93/23368, WO 93/23379, WO 94/04493, WO 94/10136 and WO 94/14793 (each of which is incorporated herein by reference in its entirety) for example describe sulfonylalkanoylamino hydroxyethylamine, sulfonylalkanoylamino hydroxyethylurea, sulfonylalkanoylamino hydroxyethyl sulfonamide and sulfonylalkanoylamino hydroxyethylaminosulfonamide isostere containing retroviral protease inhibitors. Other such compounds include hydroxyethylamine isosteres and reduced amide isosteres. See, for example, EP O 346 847; EP O 342,541; Roberts et al, "Rational Design of Peptide-Based Proteinase Inhibitors," Science, 248, 358 (1990); and Erickson et al, "Design Activity, and 2.8 Å Crystal Structure of a $C_2$ Symmetric Inhibitor Complexed to HIV-1 Protease," Science, 249, 527 (1990). U.S. Pat. No. 5,157,041, WO 94/04491, WO 94/04492, WO 94/05639 and U.S. patent application Ser. No. 08/294,468, filed Aug. 23, 1994, (each of which is incorporated herein by reference in its entirety) for example describe hydroxyethylamine, hydroxyethylurea or hydroxyethyl sulfonamide isostere containing retroviral protease inhibitors.

Several classes of compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.B. 2,200,115, G.B. 2,209,752, EP O 264,795, U.S. SIR H725 and U.S. Pat. No. 4,599,198 disclose urea-containing hydroxyethylamine renin inhibitors. EP 468 641 discloses renin inhibitors and intermediates for the preparation of the inhibitors, which include sulfonamide-containing hydroxyethylamine compounds, such as 3-(t-butoxycarbonyl)amino-cyclohexyl-1-(phenylsulfonyl)amino-2(5)-butanol. G.B. 2,200,115 also discloses sulfamoyl-containing hydroxyethylamine renin inhibitors, and EP O 264 795 discloses certain sulfonamide-containing hydroxyethylamine renin inhibitors. However, it is known that, although renin and HIV proteases are both classified as aspartyl proteases, compounds which are effective renin inhibitors generally are not predictive for effective HIV protease inhibition.

BRIEF DESCRIPTION OF THE INVENTION

The present invention relates to selected retroviral protease inhibitor compounds, analogs and pharmaceutically acceptable salts, esters and prodrugs thereof. The subject compounds are characterized as sulfonylalkanoylamino hydroxyethylamine sulfonamide inhibitor compounds. The invention compounds advantageously inhibit retroviral proteases, such as human immunodeficiency virus (HIV) protease. Therefore, this invention also encompasses pharmaceutical compositions, methods for inhibiting retroviral proteases and methods for treatment or prophylaxis of a retroviral infection, such as an HIV infection. The subject invention also relates to processes for making such compounds as well as to intermediates useful in such processes.

DETAILED DESCRIPTION OF THE INVENTION

In accordance with the present invention, there is provided a retroviral protease inhibiting compound of the formula:

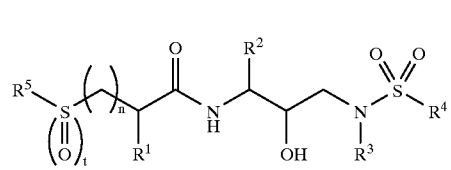

(I)

or a pharmaceutically acceptable salt, prodrug or ester thereof, wherein n and t each independently represent 0, 1 or 2; preferably n represents 1 and t represents 1 or 2;

$R^1$ represents hydrogen, alkyl, alkenyl, alkynyl, hydroxyalkyl, alkoxyalkyl, cyanoalkyl, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$ or —CH$_2$S(O)$_2$CH$_3$ radicals; preferably, $R^1$ represents hydrogen, alkyl of 1–5 carbon atoms, alkenyl of 2–5 carbon atoms, alkynyl of 2–5 carbon atoms, hydroxyalkyl of 1–3 carbon atoms, alkoxyalkyl of 1–3 alkyl and 1–3' alkoxy carbon atoms, cyanoalkyl of 1–3 alkyl carbon atoms, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$ or —CH$_2$S(O)$_2$CH$_3$ radicals; more preferably, R$^1$ represents hydrogen radical, alkyl radical of 1–3 carbon atoms, alkenyl radical of 2–3 carbon atoms, alkynyl radical of 2–3 carbon atoms or cyanomethyl radicals; even more preferably, R$^1$ represents hydrogen, methyl, ethyl or cyanomethyl radicals; yet more preferably, R$^1$ represents methyl or ethyl radicals; and most preferably, R$^1$ represents a methyl radical;

R$^2$ represents alkyl, aralkyl, alkylthioalkyl, arylthioalkyl or cycloalkylalkyl radicals; preferably, R$^2$ represents radicals of alkyl of 1–5 carbon atoms, aralkyl of 1–3 alkyl carbon atoms, alkylthioalkyl of 1–3 alkyl carbon atoms, arylthioalkyl of 1–3 alkyl carbon atoms or cycloalkylalkyl of 1–3 alkyl carbon atoms and 3–6 ring member carbon atoms; more preferably, R$^2$ represents radicals of alkyl of 3–5 carbon atoms, arylmethyl, alkylthioalkyl of 1–3 alkyl carbon atoms, arylthiomethyl or cycloalkylmethyl of 5–6 ring member carbon atoms radicals; even more preferably, R$^2$ represents isobutyl, n-butyl, CH$_3$SCH$_2$CH$_2$-, benzyl, phenylthiomethyl, (2-naphthylthio)methyl, 4-methoxy phenylmethyl, 4-hydroxyphenylmethyl, 4-fluorophenylmethyl or cyclohexylmethyl radicals; even more preferably, R$^2$ represents benzyl, 4-fluorophenylmethyl or cyclohexylmethyl radicals; most preferably, R$^2$ represents benzyl;

R$^3$ represents alkyl, cycloalkyl or cycloalkylalkyl radicals; preferably, R$^3$ represents radicals of alkyl radical of 1–5 carbon atoms, cycloalkyl of 5–8 ring members or cycloalkylmethyl radical of 3–6 ring members; more preferably, R$^3$ represents propyl, isoamyl, isobutyl, butyl, cyclopentylmethyl, cyclohexylmethyl, cyclohexyl or cycloheptyl radicals; more preferably R$^3$ represents isobutyl or cyclopentylmethyl radicals;

R$^4$ represents heteroaryl or heterocyclo radicals; preferably, R$^4$ represents benzo fused 5 to 6 ring member heteroaryl or benzo fused 5 to 6 ring member heterocyclo radicals; or R$^4$ represents a radical of the formula

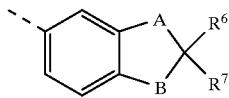

wherein A and B each independently represent O, S, SO or SO$_2$; preferably, A and B each represent O;

R$^6$ represents deuterium, alkyl or halogen radicals; preferably, R$^6$ represents deuterium, alkyl of 1–5 carbon atoms, fluoro or chloro radicals; more preferably R$^6$ represents deuterium, methyl, ethyl, propyl, isopropyl or fluoro radicals;

R$^7$ represents hydrogen, deuterium, alkyl or halogen radicals; preferably, R$^7$ represents hydrogen, deuterium, alkyl of 1–3 carbon atoms, fluoro or chloro radicals; more preferably, R$^7$ represents hydrogen, deuterium, methyl or fluoro radicals; or R$^6$ and R$^7$ each independently represent fluoro or chloro radicals; and preferably, R$^6$ and R$^7$ each represent a fluoro radical; or R$^4$ represents a radical of the formula

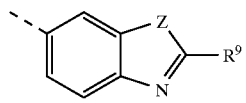

wherein Z represents O, S or NH; and R$^9$ represents a radical of formula

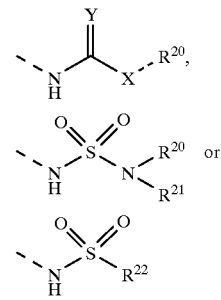

wherein Y represents O, S or NH; X represents a bond, O or NR$^{21}$;

R$^{20}$ represents hydrogen, alkyl, alkenyl, alkynyl, aralkyl, heteroaralkyl, heterocycloalkyl, aminoalkyl, N-mono-substituted or N,N-disubstituted aminoalkyl wherein said substituents are alkyl or aralkyl radicals, carboxyalkyl, alkoxycarbonylalkyl, cyanoalkyl or hydroxyalkyl radicals; preferably, R$^{20}$ represents hydrogen, alkyl of 1 to 5 carbon atoms, alkenyl of 2 to 5 carbon atoms, alkynyl of 2 to 5 carbon atoms, aralkyl of 1 to 5 alkyl carbon atoms, heteroaralkyl of 5 to 6 ring members and 1 to 5 alkyl carbon atoms, heterocycloalkyl of 5 to 6 ring members and 1 to 5 alkyl carbon atoms, aminoalkyl of 2 to 5 carbon atoms, N-mono-substituted or N,N-disubstituted aminoalkyl of 2 to 5 alkyl carbon atoms wherein said substituents are radicals of alkyl of 1 to 3 carbon atoms, aralkyl of 1 to 3 alkyl carbon atoms radicals, carboxyalkyl of 1 to 5 carbon atoms, alkoxycarbonylalkyl of 1 to 5 alkyl carbon atoms, cyanoalkyl of 1 to 5 carbon atoms or hydroxyalkyl of 2 to 5 carbon atoms; more preferably, R$^{20}$ represents hydrogen, alkyl of 1 to 5 carbon atoms, phenylalkyl of 1 to 3 alkyl carbon atoms, heterocycloalkyl of 5 to 6 ring members and 1 to 3 alkyl carbon atoms, or N-mono-substituted or N,N-disubstituted aminoalkyl of 2 to 3 carbon atoms wherein said substituents are alkyl radicals of 1 to 3 carbon atoms; and most preferably, R$^{20}$ represents hydrogen, methyl, ethyl, propyl, isopropyl, isobutyl, benzyl, 2-(1-pyrrolidinyl)ethyl, 2-(1-piperidinyl)ethyl, 2-(1-piperazinyl)ethyl, 2-(4-methylpiperazin-1-yl)ethyl, 2-(1-morpholinyl)ethyl, 2-(1-thiamorpholinyl)ethyl or 2-(N,N-dimethylamino)ethyl radicals;

R$^{21}$ represents hydrogen or alkyl radicals; preferably, R$^{21}$ represents hydrogen radical or alkyl radical of 1 to 3 carbon atoms; more preferably, R$^{21}$ represents hydrogen or methyl radicals; and most preferably, R$^{21}$ represents a hydrogen radical; or the radical of formula —NR$^{20}$R$^{21}$ represents a heterocyclo radical; preferably, the radical of formula —NR$^{20}$R$^{21}$ represents a 5 to 6 ring member heterocyclo radical; more preferably, the radical of formula —NR$^{20}$R$^{21}$ represents pyrrolidinyl, piperidinyl, piperazinyl, 4-methylpiperazinyl, 4-benzylpiperazinyl, morpholinyl or thiamorpholinyl radicals; and $R^{22}$ represents alkyl or $R^{20}R^{21}$N-alkyl radicals; preferably, $R^{22}$ represents alkyl or $R^{20}R^{21}$N-alkyl radicals wherein alkyl is 1 to 3 carbon atoms; and more preferably, $R^{22}$ represents alkyl radical of 1 to 3 carbon atoms; and preferably $R^4$ represents benzothiazol-5-yl, benzothiazol-6-yl, 2-amino-benzothiazol-5-yl, 2-(methoxycarbonylamino)benzothiazol-5-yl, 2-amino-benzothiazol-6-yl, 2-(methoxycarbonylamino)benzothiazol-6-yl, 5-benzoxazolyl, 6-benzoxazolyl, 6-benzopyranyl, 3,4-dihydrobenzopyran-6-yl, 7-benzopyranyl, 3,4-dihydrobenzopyran-7-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl, 1,4-benzodioxan-6-yl, 5-benzimidazolyl, 2-(methoxycarbonylamino) benzimidazol-5-yl, 6-quinolinyl, 7-quinolinyl, 6-isoquinolinyl or 7-isoquinolinyl radicals; more preferably, $R^4$ represents benzothiazol-5-yl, benzothiazol-6-yl, benzoxazol-5-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl, 1,4-benzodioxan-6-yl, 2-(methoxycarbonylamino) benzothiazol-5-yl, 2-(methoxycarbonylamino) benzothiazol-6-yl or 2-(methoxycarbonylamino) benzimidazol-5-yl radicals; and most preferably, $R^4$ represents benzothiazol-5-yl, benzothiazol-6-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl, 1,4-benzodioxan-6-yl, 2-(methoxycarbonylamino) benzothiazol-6-yl or 2-(methoxycarbonylamino) benzimidazol-5-yl radicals; and $R^5$ represents an alkyl, alkenyl, alkynyl or aralkyl radicals; preferably, $R^5$ represents an alkyl radical of 1–5 carbon atoms, alkenyl radical of 2–5 carbon atoms, alkynyl radical of 2–5 carbon atoms or aryl substituted alkyl of 1–5 carbon atoms; more preferably, $R^5$ represents an alkyl radical of 1–5 carbon atoms, alkenyl radical of 3–4 carbon atoms, alkynyl radical of 3–4 carbon atoms or aryl substituted alkyl of 1–4 carbon atoms; even more preferably, $R^5$ represents an alkyl radical of 1–5 carbon atoms or phenyl substituted alkyl of 2–4 carbon atoms; and most preferably, $R^5$ represents an methyl, ethyl, propyl, isopropyl or 2-phenylethyl radicals.

Preferably, the absolute stereochemistry of the carbon atom of —CH(OH)— group is (R) and the absolute stereochemistry of the carbon atoms of —CH($R^1$)— and —CH ($R^2$)— groups is (S).

A family of compounds of particular interest within Formula I are compounds embraced by the formula

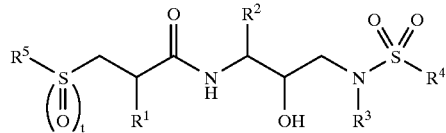

(II)

or a pharmaceutically acceptable salt, prodrug or ester thereof, wherein t, $R^1$, $R^2$, $R^3$, $R^4$ and $R^5$ are as defined above.

A family of compounds of further interest within Formula II are compounds embraced by the formula

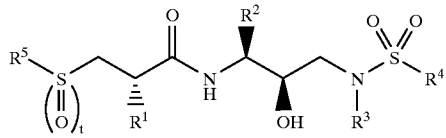

(III)

or a pharmaceutically acceptable salt, prodrug or ester thereof, wherein t, $R^1$, $R^2$, $R^3$, $R^4$ and $R^5$ are as defined above.

A more preferred family of compounds within Formula III consists of compounds or a pharmaceutically acceptable salt, prodrug or ester thereof, wherein t represents 2;

$R^1$ represents methyl or ethyl radicals;

$R^2$ represents a benzyl, 4-fluorophenylmethyl or cyclohexylmethyl radical;

$R^3$ represents propyl, isoamyl, isobutyl, butyl, cyclohexyl, cycloheptyl, cyclopentylmethyl or cyclohexylmethyl radicals;

$R^4$ represents 2,3-dihydrobenzofuran-5-yl, 1,3-benzodioxol-5-yl, 2-methyl-1,3-benzodioxol-5-yl, 2,2-dimethyl-1,3-benzodioxol-5-yl, benzothiazol-6-yl, 2,2-dideutero-1,3-benzodioxol-5-yl, 2,2-difluoro-1,3-benzodioxol-5-yl or 1,4-benzodioxan-6-yl radicals; and $R^5$ represents methyl, ethyl, propyl, isopropyl or 2-phenylethyl radicals.

Compounds of interest include the following:

N-[2R-hydroxy-3-[(2-methylpropyl)[(1,3-benzodioxol-5-yl)sulfonyl]amino]-1S-(phenylmethyl)propyl]-2S-methyl-3-(methylsulfonyl)propanamide;

N-[2R-hydroxy-3-[(2-methylpropyl)[(1,4-benzodioxan-6-yl)sulfonyl]amino]-1S-(phenylmethyl)propyl]-2S-methyl-3-(methylsulfonyl)propanamide;

N-[2R-hydroxy-3-[(2-methylpropyl)[(benzothiazol-6-yl) sulfonyl]amino]-1S-(phenylmethyl)propyl]-2S-methyl-3-(methylsulfonyl)propanamide;

N-[2R-hydroxy-3-[(2-methylpropyl)[(benzothiazol-5-yl) sulfonyl]amino]-1S-(phenylmethyl)propyl]-2S-methyl-3-(methylsulfonyl)propanamide; and N-[2R-hydroxy-3-[(2-methylpropyl)[(2,3-dihydrobenzofuran-5-yl)sulfonyl]amino]-1S-(phenylmethyl)propyl]-2S-methyl-3-(methylsulfonyl) propanamide.

As utilized herein, the term "alkyl", alone or in combination, means a straight-chain or branched-chain alkyl radical containing preferably from 1 to 8 carbon atoms, more preferably from 1 to 5 carbon atoms, most preferably 1–3 carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "hydroxyalkyl", alone or in combination, means an alkyl radical as defined above wherein at least one hydrogen radical is replaced with a hydroxyl radical, preferably 1–3 hydrogen radicals are replaced by hydroxyl radicals, more preferably, 1–2 hydrogen radicals are replaced by hydroxyl radicals, and most preferably, one hydrogen radical is replaced by a hydroxyl radical. The term "alkenyl", alone or in combination, means a straight-chain or branched-chain hydrocarbon radical having one or more double bonds and containing preferably from 2 to 8 carbon atoms, more preferably from 2 to 5 carbon atoms, most preferably from 2 to 3 carbon atoms. Examples of suitable alkenyl radicals include ethenyl, propenyl, 2-methylpropenyl, 1,4-butadienyl and the like. The term "alkynyl", alone or in combination, means a straight-chain or branched chain hydrocarbon radical having one or more triple bonds and containing preferably from 2 to 8 carbon atoms, more preferably from 2 to 5 carbon atoms, most preferably from 2 to 3 carbon atoms. Examples of alkynyl radicals include ethynyl, propynyl (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains preferably from 3 to 8 carbon atom ring members, more preferably from 3 to 7 carbon atom ring members, most preferably from 5 to 6 carbon atom ring members, and which may optionally be a benzo fused ring system which is optionally substituted as defined herein with respect to the definition of aryl. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as naphthyl and β-carbolinyl, and substituted ring systems, such as biphenyl, phenylpyridyl, naphthyl and diphenylpiperazinyl. The term "cycloalkylalkyl" means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like. The term "benzo", alone or in combination, means the divalent radical $C_6H_4=$ derived from benzene. The term "aryl", alone or in combination, means a phenyl or naphthyl radical which is optionally substituted with one or more substituents selected from alkyl, alkoxy, halogen, hydroxy, amino, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl and the like. Examples of aryl radicals are phenyl, p-tolyl, 4-methoxyphenyl, 4-(tert-butoxy)phenyl, 3-methyl-4-methoxyphenyl, 4-$CF_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like. The terms "aralkyl", and "aralkoxy", alone or in combination, means an alkyl or alkoxy radical as defined above in which at least one hydrogen atom is replaced by an aryl radical as defined above, such as benzyl, benzyloxy, 2-phenylethyl, dibenzylmethyl, hydroxyphenylmethyl, methylphenylmethyl, diphenylmethyl, diphenylmethoxy, 4-methoxyphenylmethoxy and the like. The term "aralkoxycarbonyl", alone or in combination, means a radical of the formula aralkyl-O—C(O)— in which the term "aralkyl" has the significance given above. Examples of an aralkoxycarbonyl radical are benzyloxycarbonyl and 4-methoxyphenylmethoxycarbonyl. The term aryloxy means a radical of the formula aryl-O— in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl radical of the formula cycloalkyl-C(O)— in which the term "cycloalkyl" has the significance give above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl and the like. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" means an acyl radical derived from an arylcarboxylic acid, "aryl" having the meaning given above. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The terms "heterocyclo," alone or in combination, means a saturated or partially unsaturated monocyclic, bicyclic or tricyclic heterocycle radical containing at least one, preferably 1 to 4, more preferably 1 to 2, nitrogen, oxygen or sulfur atom ring member and having preferably 3 to 8 ring members in each ring, more preferably 3 to 7 ring members in each ring and most preferably 5 to 6 ring members in each ring. "Heterocyclo" is intended to include sulfones, sulfoxides, N-oxides of tertiary nitrogen ring members, and carbocyclic fused and benzo fused ring systems. Such heterocyclo radicals may be optionally substituted on at least one, preferably 1 to 4, more preferably 1 to 2, carbon atoms by halogen, alkyl, alkoxy, hydroxy, oxo, aryl, aralkyl, heteroaryl, heteroaralkyl, amidino, N-alkylamidino, alkoxycarbonylamino, alkylsulfonylamino and the like, and/or on a secondary nitrogen atom (i.e., —NH—) by hydroxy, alkyl, aralkoxycarbonyl, alkanoyl, heteroaralkyl, phenyl or phenylalkyl and/or on a tertiary nitrogen atom (i.e., =N—) by oxido. "Heterocycloalkyl" means an alkyl radical as defined above in which at least one hydrogen atom is replaced by a heterocyclo radical as defined above, such as pyrrolidinylmethyl, tetrahydrothienylmethyl, pyridylmethyl and the like. The term "heteroaryl", alone or in combination, means an aromatic heterocyclo radical as defined above, which is optionally substituted as defined above with respect to the definitions of aryl and heterocyclo. Examples of such heterocyclo and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, (e.g., 2-(1-piperidinyl)pyridyl and 2-(4-benzyl piperazin-1-yl-1-pyridinyl, etc.), pyrazinyl, pyrimidinyl, furyl, tetrahydrofuryl, thienyl, tetrahydrothienyl and its sulfoxide and sulfone derivatives, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-,2-,4- or 5-benzimidazolyl, methylenedioxyphen-4-yl, methylenedioxyphen-5-yl, ethylenedioxyphenyl, benzothiazolyl, benzopyranyl, benzofuryl, 2,3-dihydrobenzofuryl, benzoxazolyl, thiophenyl and the like. The term "heteroaralkyl", alone or in combination, means an alkyl radical as defined above in which at least one hydrogen atom is replaced by an heteroaryl radical as defined above, such as benzofurylmethyl, 3-furylpropyl, quinolinylmethyl, 2-thienylethyl, pyridylmethyl, 2-pyrrolylpropyl, 1-imidazolylethyl and the like. The term "cycloalkylalkoxycarbonyl" means an acyl group derived from a cycloalkylalkoxycarboxylic acid of the formula cycloalkylalkyl-O—COOH wherein cycloalkylalkyl has the meaning given above. The term "aryloxyalkanoyl" means an acyl radical of the formula aryl-O-alkanoyl wherein aryl and alkanoyl have the meaning given above. The term "heterocycloalkoxycarbonyl" means an acyl group derived from heterocycloalkyl-O—COOH wherein heterocycloalkyl is as defined above. The term "heterocycloalkanoyl" is an acyl radical derived from a heterocycloalkylcarboxylic acid wherein heterocyclo has the meaning given above. The term "heterocycloalkoxycarbonyl" means an acyl radical derived from a heterocycloalkyl-O—COOH wherein heterocyclo has the meaning given above. The term "heteroaryloxycarbonyl" means an acyl radical derived from a carboxylic acid represented by heteroaryl-O—COOH wherein heteroaryl has the meaning given above. The term "aminocarbonyl" alone or in combination, means an amino-substituted carbonyl (carbamoyl) group wherein the amino group can be a primary, secondary or tertiary amino group containing substituents selected from alkyl, aryl, aralkyl, cycloalkyl, cycloalkylalkyl radicals and the like. The term "aminoalkanoyl" means an acyl group derived from an amino-substituted alkylcarboxylic acid wherein the amino group can be a primary, secondary or tertiary amino group containing substituents selected from alkyl, aryl, aralkyl, cycloalkyl, cycloalkylalkyl radicals and the like. The term "halogen" means fluorine, chlorine, bromine or iodine. The term "haloalkyl" means an alkyl radical having the meaning as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term "leaving group" (L or W) generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving group are indicated herein where appropriate.

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R). However, such procedures are generally applicable to those compounds of opposite configuration, e.g., where the stereochemistry about the hydroxyl group is (S). In addition, the compounds having the (R) stereochemistry can be utilized to produce those having the (S) stereochemistry. For example, a compound having the (R) stereochemistry can be inverted to the (S) stereochemistry using well-known methods.

Preparation of Compounds of Formula I

The compounds of the present invention represented by Formula I above can be prepared utilizing the following general procedures as schematically shown in Schemes I and II.

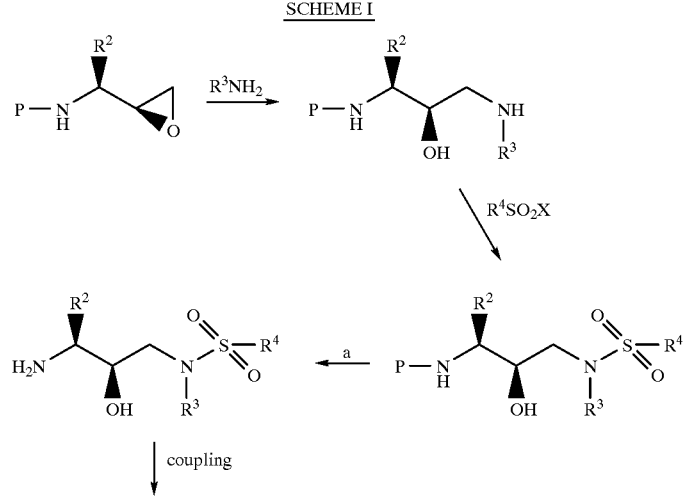

SCHEME I

-continued
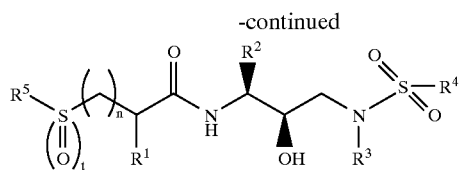
a) deprotection; X = Cl or Br.
SCHEME II
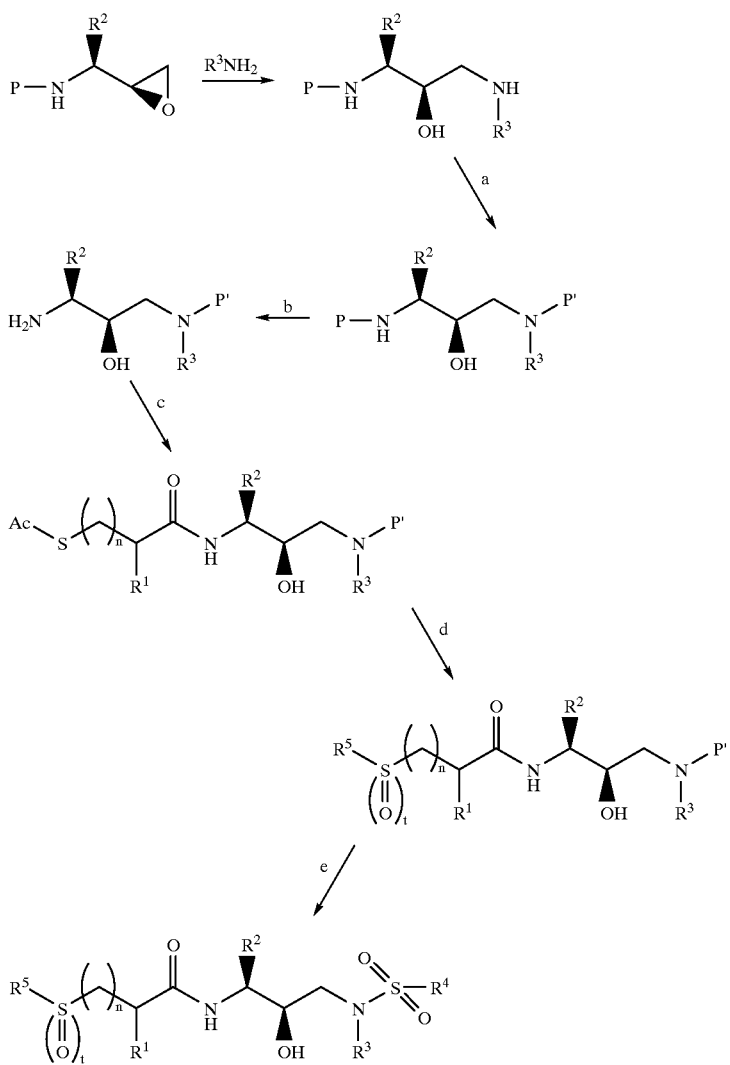
a) protection; b) selective deprotection;
c) AcS(CH$_2$)$_n$CH(R$^1$)CO$_2$H coupling; d) hydrolysis,
R$^5$L displacement, oxidation; e) deprotection,
R$^4$SO$_2$X coupling (X = Cl or Br).
An N-protected chloroketone derivative of an amino acid having the formula:

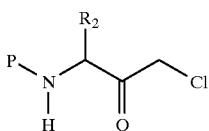

wherein P represents an amino protecting group, and $R^2$ is as defined above, is reduced to the corresponding alcohol utilizing an appropriate reducing agent. Suitable amino protecting groups are well known in the art and include carbobenzoxy, t-butoxycarbonyl, and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from –10° C. to about 25° C., preferably at about 0° C., in a suitable solvent system such as, for example, tetrahydrofuran, and the like. The N-protected chloroketones are commercially available, e.g., such as from Bachem, Inc., Torrance, Calif. Alternatively, the chloroketones can be prepared by the procedure set forth in S. J. Fittkau, *J. Prakt. Chem.*, 31, 1037 (1973), and subsequently N-protected utilizing procedures which are well known in the art.

The halo alcohol can be utilized directly, as described below, or, preferably, is reacted, preferably at room temperature, with a suitable base in a suitable solvent system to produce an N-protected amino epoxide of the formula:

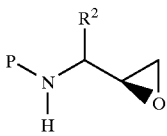

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared, such as in co-owned and co-pending PCT Patent Application Ser. No. PCT/US93/04804 (WO 93/23388) and PCT/US94/12201, and US Patent Application Attorney Docket No. C-2860, each of which is incorporated herein by reference in their entirety) disclose methods of preparing chiral epoxide, chiral cyanohydrin, chiral amine and other chiral intermediates useful in the preparation of retroviral protease inhibitors, starting with a DL-, D- or L-amino acid which is reacted with a suitable amino-protecting group in a suitable solvent to produce an amino-protected amino acid ester. For the purposes of illustration, a protected L-amino acid with the following formula will be used to prepare the inhibitors of this invention:

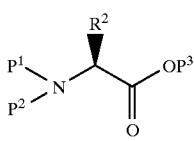

wherein $P^3$ represents carboxyl-protecting group, e.g., methyl, ethyl, benzyl, tertiary-butyl, 4-methoxyphenylmethyl and the like; $R^2$ is as defined above; and $P^1$ and $P^2$ and P' independently are selected from amine protecting groups, including but not limited to, aralkyl, substituted aralkyl, cycloalkenylalkyl and substituted cycloalkenylalkyl, allyl, substituted allyl, acyl, alkoxycarbonyl, aralkoxycarbonyl and silyl. Examples of aralkyl include, but are not limited to benzyl, ortho-methylbenzyl, trityl and benzhydryl, which can be optionally substituted with halogen, alkyl of $C_1$–$C_8$, alkoxy, hydroxy, nitro, alkylene, amino, alkylamino, acylamino and acyl, or their salts, such as phosphonium and ammonium salts. Examples of aryl groups include phenyl, naphthalenyl, indanyl, anthracenyl, durenyl, 9-(9-phenylfluorenyl) and phenanthrenyl, cycloalkenylalkyl or substituted cycloalkylenylalkyl radicals containing cycloalkyls of $C_6$–$C_{10}$. Suitable acyl groups include carbobenzoxy, t-butoxycarbonyl, iso-butoxycarbonyl, benzoyl, substituted benzoyl, butyryl, acetyl, tri-fluoroacetyl, tri-chloroacetyl, phthaloyl and the like. Preferably $P^1$ and $P^2$ are independently selected from aralkyl and substituted aralkyl. More preferably, each of $P^1$ and $P^2$ is benzyl.

Additionally, the $P^1$ and/or $P^2$ and/or P' protecting groups can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl. The term silyl refers to a silicon atom optionally substituted by one or more alkyl, aryl and aralkyl groups.

Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of the amine functions to provide mono- or bis-disilylamine can provide derivatives of the aminoalcohol, amino acid, amino acid esters and amino acid amide. In the case of amino acids, amino acid esters and amino acid amides, reduction of the carbonyl function provides the required mono- or bis-silyl aminoalcohol. Silylation of the aminoalcohol can lead to the N,N,O-tri-silyl derivative. Removal of the silyl function from the silyl ether function is readily accomplished by treatment with, for example, a metal hydroxide or ammonium flouride reagent, either as a discrete reaction step or in situ during the preparation of the amino aldehyde reagent. Suitable silylating agents are, for example, trimethylsilyl chloride, tert-buty-dimethylsilyl chloride, phenyldimethylsilyl chlorie, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

The amino-protected L-amino acid ester is then reduced, to the corresponding alcohol. For example, the amino-protected L-amino acid ester can be reduced with diisobutylaluminum hydride at –78° C. in a suitable solvent such as toluene. Preferred reducing agents include lithium aluminium hydride, lithium borohydride, sodium borohydride, borane, lithium tri-ter-butoxyaluminum hydride, borane/THF complex. Most preferably, the reducing agent is diisobutylaluminum hydride (DiBAL-H) in toluene. The resulting alcohol is then converted, for example, by way of a Swern oxidation, to the corresponding aldehyde of the formula:

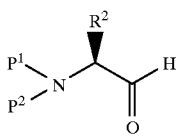

wherein $P^1$, $P^2$ and $R^2$ are as defined above. Thus, a dichloromethane solution of the alcohol is added to a cooled (−75 to −68° C.) solution of oxalyl chloride in dichloromethane and DMSO in dichloromethane and stirred for 35 minutes.

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydro thiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutyl chloroformate and DMSO. The oxidation conditions reported by Reetz et al [*Angew Chem.*, 99, p. 1186, (1987)], *Angew Chem. Int. Ed. Engl.*, 26, p. 1141, 1987) employed oxalyl chloride and DMSO at −78° C.

The preferred oxidation method described in this invention is sulfur trioxide pyridine complex, triethylamine and DMSO at room temperature. This system provides excellent yields of the desired chiral protected amino aldehyde usable without the need for purification i.e., the need to purify kilograms of intermediates by chromatography is eliminated and large scale operations are made less hazardous. Reaction at room temperature also eliminated the need for the use of low temperature reactor which makes the process more suitable for commercial production.

The reaction may be carried out under an inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2,6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted [either $P^1$ or $P^2$=H] or N,N-disubstituted aldehyde.

In addition, hydride reduction of an amide or ester derivative of the corresponding benzyl (or other suitable protecting group) nitrogen protected phenylalanine, substituted phenylalanine or cycloalkyl analog of phenylalanine derivative can be carried out to provide the aldehydes. Hydride transfer is an additional method of aldehyde synthesis under conditions where aldehyde condensations are avoided, cf, Oppenauer Oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −20° C. to about 45° C., and preferably from abut 5° C. to about 25° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

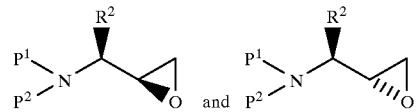

The diastereomers can be separated e.g., by chromatography, or, alternatively, once reacted in subsequent steps the diastereomeric products can be separated. A D-amino acid can be utilized in place of the L-amino acid in order to prepare compounds having an (S) stereochemistry at the carbon bonded to $R^2$.

The addition of chloromethyllithium or bromomethylithium to a chiral amino aldehyde is highly diastereoselective. Preferably, the chloromethyllithium or bromomethylithium is generated in-situ from the reaction of the dihalomethane and n-butyllithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane, ethylene dichloride, methylene chloride can be used as pure solvents or as a mixture. Dipolar aprotic solvents such as acetonitrile, DMF, N-methylpyrrolidone are useful as solvents or as part of a solvent mixture. The reaction can be carried out under an inert atmosphere such as nitrogen or argon. For n-butyl lithium can be substituted other organometalic reagents reagents such as methyllithium, tert-butyl lithium, sec-butyl lithium, phenyllithium, phenyl sodium and the like. The reaction can be carried out at temperatures of between about −80° C. to 0° C. but preferably between about −80° C. to −20° C. The most preferred reaction temperatures are between −40° C. to −15° C. Reagents can be added singly but multiple additions are preferred in certain conditions. The preferred pressure of the reaction is atmospheric however a positive pressure is valuable under certain conditions such as a high humidity environment.

Alternative methods of conversion to the epoxides of this invention include substitution of other charged methylenation precurser species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of this invention into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tosylate, methyl mesylate, methyl triflate, ethyl bromide, isopropyl bromine the benzyl chloride or the like, in the presence of an organic or inorganic base Alternatively, the protected aminosulfide alcohol can be alkylated with, for example, the alkylating agents above, to provide a sulfonium salts that are subsequently converted into the subject epoxides with tert-amine or mineral bases.

The desired epoxides formed, using most preferred conditions diastereoselectively in ratio amounts of at least about an 85:15 ratio (S:R). The product can be purified by chromatography to give the diastereomerically and enantiomerically pure product but it is more conveniently used directly without purification to prepare retroviral protease inhibitors. The foregoing process is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenylalaninol and the like, or resolution can occur at intermediate or final steps. Chiral auxiliaries such as one or two equivilants of camphor sulfonic acid, citric acid, camphoric acid, 2-methoxyphenylacetic acid and the like can be used to form salts, esters or amides of the compounds of this invention. These compounds or derivatives can be crystallized or separated chromatographically using either a chiral or achiral column as is well known to those skilled in the art.

The amino epoxide is then reacted, in a suitable solvent system, with an equal amount, or preferably an excess of, a desired amine of the formula $R^3NH_2$, wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. The resulting product is a 3-(N-protected amino)-3-($R^2$)-1-($NHR^3$)-propan-2-ol derivative (hereinafter referred to as an amino alcohol) can be represented by the formulas:

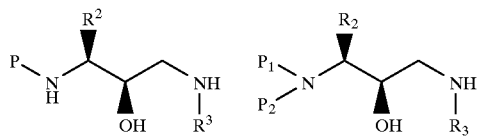

wherein P, $P^1$, $P^2$, $R^2$ and $R^3$ are as described above. Alternatively, a haloalcohol can be utilized in place of the amino epoxide.

The amino alcohol defined above is then reacted in a suitable solvent with the sulfonyl chloride $R^4SO_2Cl$, the sulfonyl bromide $R^4SO2Br$ or the corresponding sulfonyl anhydride, preferably in the presence of an acid scavenger. Suitable solvents in which the reaction can be conducted include methylene chloride, tetrahydrofuran and the like. Suitable acid scavengers include triethylamine, pyridine and the like. The resulting sulfonamide derivative can be represented, depending on the epoxide utilized by the formulas

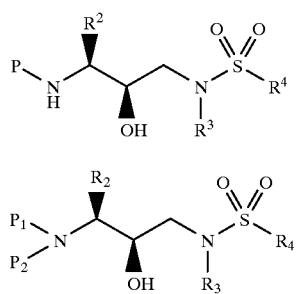

wherein P, $P^1$, $P^2$, $R^2$, $R^3$ and $R^4$ are as defined above. These intermediates are useful for preparing inhibitor compounds of the present invention.

Alternatively, the protected amino alcohol from the epoxide opening can be further protected at the newly introduced amino group with a protecting group P' which is not removed with the removal of the amino protecting groups P or $P^1$ and $P^2$, i.e., P' is selectively removable. One skilled in the art can choose appropriate combinations of P', P, $P^1$ and $P^2$. For example, suitable combinations are P=Cbz and P'=Boc; P'=Cbz and P=Boc; $P^1$=Cbz, $P^2$=benzyl and P'=Boc; and $P^1$=$P^2$=benzyl and P'=Boc. The resulting compound represented by the formula

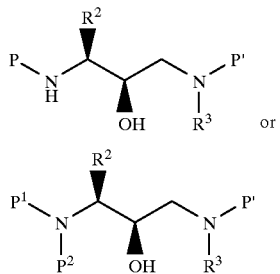

can be carried through the remainder of the synthesis to provide a compound of the formula

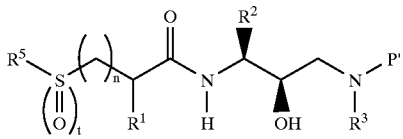

wherein n, t, P', $R^1$, $R^2$, $R^3$ and $R^5$ are as defined above. The remainder of the synthesis above can be carried out as desired either by the addition of desired residues or groups one at a time or in a preformed molecule made up of more that one residue or group in one step. The former approach is the sequential synthesis method and the latter is the convergent synthesis method. Synthetic transformations are possible at this stage also. The protecting group P' is then selectively removed and the resulting amine is reacted with the sulfonyl chloride $R^4SO_2Cl$, the sulfonyl bromide $R^4SO_2Br$ or the corresponding sulfonyl anhydride, preferably in the presence of an acid scavenger, to form the compounds of the present invention

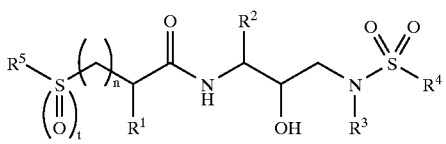

wherein n, t, $R^1$, $R^2$, $R^3$, $R^4$ and $R^5$ are as defined above. This selective deprotection and conversion to the sulfonamide can be accomplished at either the end of the synthesis or at any appropriate intermediate step as desired. An example is outlined in Scheme II.

The sulfonyl halides of the formula $R^4SO_2X$ can be prepared by the reaction of a suitable aryl, heteroaryl and benzo fused heterocyclo Grignard or lithium reagents with sulfuryl chloride, or sulfur dioxide followed by oxidation with a halogen, preferably chlorine. Aryl, heteroaryl and benzo fused heterocyclo Grignard or lithium reagents can be prepared from their corresponding halide (such as chloro or bromo) compounds which are commercially available or readily prepared from commercially available starting materials using known methods in the art. Also, thiols may be oxidized to sulfonyl chlorides using chlorine in the presence of water under carefully controlled conditions. Additionally, sulfonic acids, such as arylsulfonic acids, may be converted to sulfonyl halides using reagents such as $PCl_5$, $SOCl_2$, $ClC(O)C(O)Cl$ and the like, and also to anhydrides using suitable dehydrating reagents. The sulfonic acids may in turn be prepared using procedures well known in the art. Some sulfonic acids are commercially available. In place of the sulfonyl halides, sulfinyl halides ($R^4SOX$) or sulfenyl halides ($R^4SX$) can be utilized to prepare compounds wherein the $—SO_2—$ moiety is replaced by an $—SO—$ or $—S—$ moiety, respectively. Arylsulfonic acids, benzo fused heterocyclo sulfonic acids or heteroaryl sulfonic acids can be prepared by sulfonation of the aromatic ring by well known methods in the art, such as by reaction with sulfuric acid, $SO_3$, $SO_3$ complexes, such as $DMF(SO_3)$, pyridine $(SO_3)$, N,N-dimethylacetamide$(SO_3)$, and the like. Preferably, arylsulfonyl halides are prepared from aromatic compounds by reaction with $DMF(SO_3)$ and $SOCl_2$ or $ClC(O)C(O)Cl$. The reactions may be performed stepwise or in a single pot.

Arylsulfonic acids, benzo fused heterocyclo sulfonic acids, heteroaryl sulfonic acids, arylmercaptans, benzo fused heterocyclo mercaptans, heteroarylmercaptans, arylhalides, benzo fused heterocyclo halides, heteroarylhalides, and the like are commercially available or can be readily prepared from starting materials commercially available using standard methods well known in the art. For example, a number of sulfonic acids ($R^4SO_3H$) represented by the formulas

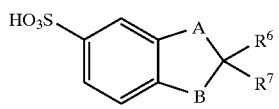

and

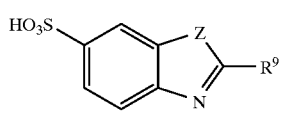

wherein A, B, Z, $R^6$, $R^7$ and $R^9$ are as defined above, have been prepared from 1,2-benzenedithiol, 2-mercaptanphenol, 1,2-benzenediol, 2-aminobenzothiazole, benzothiazole, 2-aminobenzimidazole, benzimidazole, and the like, which are commercially available, by Carter, U.S. Pat. No. 4,595,407; Ehrenfreund et al., U.S. Pat. No. 4,634,465; Yoder et al., J. Heterocycl. Chem. 4:166–167 (1967); Cole et al., Aust. J. Chem. 33:675–680 (1980); Cabiddu et al., Synthesis 797–798 (1976); Ncube et al., Tet. Letters 2345–2348 (1978); Ncube et al., Tet. Letters 255–256 (1977); Ansink & Cerfontain, Rec. Trav. Chim.Pays-Bas 108:395–403 (1989); and Kajihara & Tsuchiya, EP 638564 A1, each of which are incorporated herein by reference in their entirety. For example, 1,2-benzenedithiol, 2-mercaptanphenol or 1,2-benzenediol can be reacted with $R^6R^7C(L')_2$, where L' is as defined below, preferably, Br or I, in the presence of a base, such as hydroxide, or $R^6R^7C=O$ in the presence of acid, such as toluenesulfonic acid, or $P_2O_5$., to prepare the substituted benzo fused heterocycle of formula

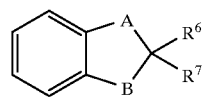

which can then be sulfonylated to the sulfonic acid above. For example, $CF_2Br_2$ or $CD_2Br2$ can be reacted with 1,2-benzenedithiol, 2-mercaptanphenol or 1,2-benzenediol in the presence of base to produce the compounds

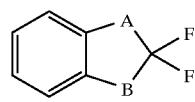

or

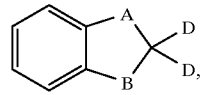

respectively, wherein A and B are O or S and D is a deuterium atom. Also, when A and/or B represent S, the sulfur can be oxidized using the methods described below to the sulfone or sulfoxide derivatives.

Following preparation of the sulfonamide derivative, the amino protecting group P or $P^1$ and $P^2$ amino protecting groups are removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative.

Following neutralization of the salt, the amine is then coupled to the sulfone/sulfoxidealkanoyl compound or an optical isomer thereof (such as where the group —CH($R^1$)— is R or S), corresponding to the formula

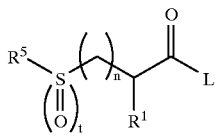

wherein n, t and $R^5$ are as defined above, and L is leaving group such as halide, anhydride, active ester, and the like. Alternatively, the sulfone/sulfoxide alkanoyl compound or an optical isomer thereof can be coupled to the protected amine

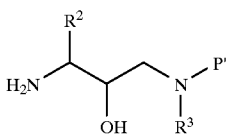

followed by deprotection and coupling to $R^4SO_2X$, where X is Cl or Br and P', $R^2$, $R^3$ and $R^4$ is as defined above.

Such sulfone/sulfoxidealkanoyl compounds where n is 1 can be prepared by reacting a mercaptan of the formula $R^5SH$ with a substituted methacrylate of the formula

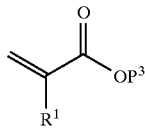

by way of a Michael Addition. Such substituted methacrylates are commercially available or readily prepared from commercially available starting materials using standard methods well known in the art. The Michael Addition is conducted in a suitable solvent and in the presence of a suitable base, to produce the corresponding thiol derivative represented by the formula

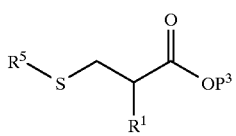

wherein $P^3$, $R^1$ and $R^5$ are as defined above. Suitable solvents in which the Michael Addition can be conducted include alcohols such as, for example, methanol, ethanol, butanol and the like, as well as ethers, e.g., THF, and acetonitrile, DMF, DMSO, and the like, including mixtures thereof. Suitable bases include Group I metal alkoxides such as, for example sodium methoxide, sodium ethoxide, sodium butoxide and the like as well as Group I metal hydrides, such as sodium hydride, including mixtures thereof. The thiol derivative is converted into the corresponding sulfone or sulfoxide of the formula

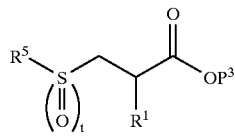

by oxidizing the thiol derivative with a suitable oxidation agent in a suitable solvent. Suitable oxidation agents include, for example, hydrogen peroxide, sodium meta-perborate, oxone (potassium peroxy monosulfate), meta-chloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The sulfone/sulfoxide is then converted into the corresponding free acid of the formula

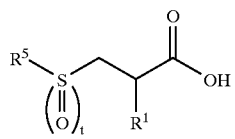

utilizing a suitable base, e.g., lithium hydroxide, sodium hydroxide, and the like, including mixtures thereof, in a suitable solvent, such as, for example, THF, acetonitrile, DMF, DMSO, methylene chloride and the like, including mixtures thereof. The free acid can then be converted into the sulfone/sulfoxidealkanoyl compound

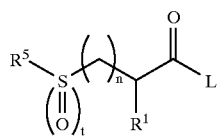

wherein n, t and $R^5$ are as defined above, and L is leaving group such as halide, anhydride, active ester, and the like. Alternatively, the free acid can be resolved into its optical isomers (such as where the group —CH($R^1$)— is R or S) using well known methods in the art, such As by forming diastereomeric salts or esters and crystallizing or chromatographing, and then converted into the sulfone/sulfoxidealkanoyl compound.

Alternatively, the thioether or corresponding protected thiol of formulas

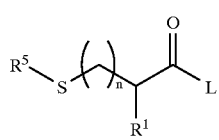

or

-continued

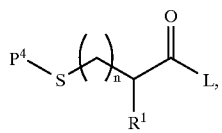

respectively, where n, L, R¹ and R⁵ are as defined above, can be coupled to one of the amines

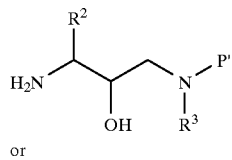

or

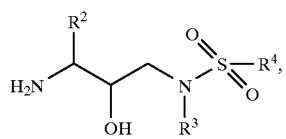

followed by conversion to the protease inhibitors of the present invention. $P^4$ is a sulfur protecting group, such as acetyl, benzoyl and the like. The acetyl and benzoyl groups can be removed by treatment with an inorganic base or an amine, preferably ammonia, in an appropriate solvent such as methanol, ethanol, isopropanol, toluene or tetrahydrofuran. The preferred solvent is methanol.

For example, one can couple the commercially available acid

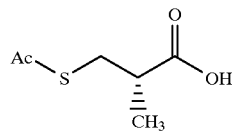

to one of the amines

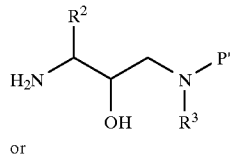

or

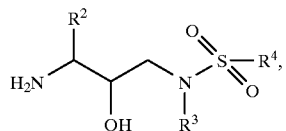

deacetylate the sulfur group, such as by hydrolysis with a suitable base, such as hydroxide, or an amine, such as ammonia, and then react the resulting thiol with $R^5L'$ agent, wherein $R^5$ and L' are as defined above, to afford compounds with one of the following structures

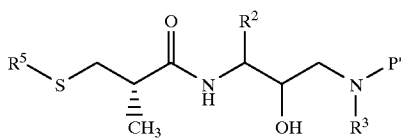

or

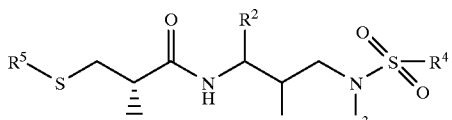

or specific diastereomeric isomers thereof. The sulfur can then be oxidized to the corresponding sulfone or sulfoxide using suitable oxidizing agents, as described above, to afford the desired intermediate followed by further reactions to prepare the sulfonamide inhibitor, or directly to the sulfonamide inhibitor. Alternatively, the acid or the $P^3$ protected acid can be deacetylated, reacted with $R^5L'$ agent, deprotected and oxidized to the corresponding sulfone or sulfoxide using suitable oxidizing agents, as described above to afford the compound of formula

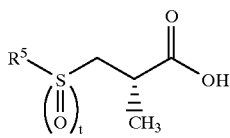

wherein t and $R^5$ are as defined above. This sulfone/sulfoxide carboxylic acid can then be coupled to the amine intermediate described above followed by further reaction to prepare the sulfonamide inhibitor, or to the sulfonamide amine compound to produce the sulfonamide inhibitor directly. The L' group of the $R^5L'$ agent is a leaving group such as a halide (chloride, bromide,. iodide), mesylate, tosylate or triflate. The reaction of the mercaptan with $R^5L'$ is performed in the presence of a suitable base, such as triethylamine, diisopropylethylamine, 1,8-diazabicyclo[5.4.0]undec-7-ene (DBu) and the like, in a suitable solvent such as toluene, tetrahydrofuran, or methylene chloride. The preferred base is DBU and the preferred solvent is toluene. Where $R^5$ is a methyl group, $R^5L'$ can be methyl chloride, methyl bromide, methyl iodide, or dimethyl sulfate, and preferably methyl iodide.

Alternatively, a substituted methacrylate of the formula

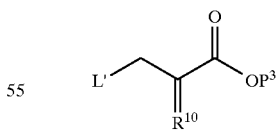

wherein L' represents a leaving group as previously defined, $P^3$ is as defined above and $R^{10}$ represents radicals which upon reduction of the double bond produce radicals of $R^1$, is reacted with $R^5SM$ followed by oxidation, as described above, or a suitable sulfonating agent, such as, for example, a sulfinic acid represented by the formula $R^5SO_2M$, wherein $R^5$ is as defined above and M represents a metal adapted to form a salt of the acid, e.g., sodium, to produce the corresponding sulfone represented by the formula

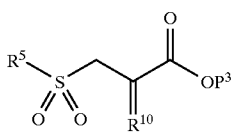

wherein $P^3$, $R^5$ and $R^{10}$ are as defined above. The sulfone is then deprotected to form the corresponding carboxylic acid. For example, when $P^3$ is a tertiary-butyl group, it can be removed by treatment with an acid, such as hydrochloric acid or trifluoracetic acid. The preferred method is using 4N hydrochloric acid in dioxane.

The resulting carboxylic acid is then asymmetrically hydrogenated utilizing an asymmetric hydrogenation catalyst such as, for example, a ruthenium-BINAP complex, to produce the reduced product, substantially enriched in the more desired isomer, represented by one of the formulas

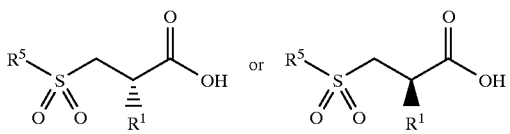

wherein $R^1$ and $R^5$ are as defined above. Where the more active isomer has the R-stereochemistry, a Ru(R-BINAP) asymmetric hydrogenation catalyst can be utilized. Conversely, where the more active isomer has the S-sterochemistry, a Ru(S-BINAP) catalyst can be utilized. Where both isomers are active, or where it is desired to have a mixture of the two diastereomers, a hydrogenation catalyst such as platinum or palladium on carbon can be utilized to reduce the above compound. The reduced compound is then coupled to an amine as described above.

The chemical reactions described above are generally disclosed in terms of their broadest application to the preparation of the compounds of this invention. occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples illustrate the preparation of inhibitor compounds of the present invention and intermediates useful in preparing the inhibitor compounds of the present invention.

EXAMPLE 1

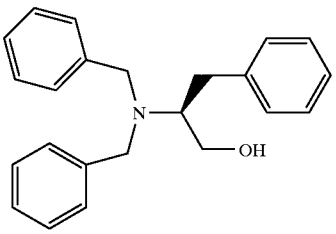

Preparation of 2S-[Bis(phenylmethyl)amino] benzenepropanol

Method 1

2S-[Bis(phenylmethyl)amino]benzenepropanol from the DIBAL Reduction of N,N-bis(phenylmethyl)-L-Phenylalanine phenylmethyl ester Step 1

A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time—25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexane). Usually the product is pure enough to be used directly in the next step without further purification. $^1$H NMR spectrum was in agreement with published literature. $^1$H NMR (CDCL$_3$) δ, 3.00 and 3.14 (ABX-system, 2H, $J_{AB}$=14.1 Hz, $J_{AX}$=7.3 Hz and $J_{BX}$=5.9 Hz), 3.54 and 3.92 (AB-System, 4H, $J_{AB}$=13.9 Hz), 3.71 (t, 1H, J=7.6 Hz), 5.11 and 5.23 (AB-System, 2H, $J_{AB}$=12.3 Hz), and 7.18 (m, 20H). EIMS: m/z 434 (M−1).

Step 2

The benzylated phenylalanine phenylmethyl ester (0.302 mol) from the previous reaction was dissolved in toluene (750 mL) and cooled to −55° C. A 1.5 M solution of DIBAL in toluene (443.9 mL, 0.666 mol) was added at a rate to maintain the temperature between −55 to −50° C. (addition time—1 hr). The mixture was stirred for 20 minutes under a nitrogen atmosphere and then quenched at −55° C. by the slow addition of methanol (37 ml). The cold solution was then poured into cold (5° C.) 1.5 N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5 N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of βS-2-[Bis(phenylmethyl)amino]benzenepropanol, 40% yield from L-phenylalanine. An additional 7 g (7%) of product can be obtained from recrystallization of the concentrated mother liquor. TLC of product Rf=0.23 (10% ethyl acetate/hexane, silica gel); $^1$H NMR (CDC13) δ 2.44 (m, 1H,), 3.09 (m, 2H), 3.33 (m, 1H), 3.48 and 3.92 (AB-System, 4H, $J_{AB}$=13.3 Hz), 3.52 (m, 1H) and 7.23 (m, 15H); $[α]_D25$+42.4 (c 1.45, $CH_2Cl_2$); DSC 77.67° C.; Anal. Calcd. for $C_{23}H_{25}ON$: C, 83.34; H, 7.60; N, 4.23. Found: C, 83.43; H, 7.59; N, 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

Method 2

Preparation of βS-2-[Bis(phenylmethyl)amino]benzenepropanol from the N,N-Dibenzylation of L-Phenylalaninol L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnight to give a semi-dry solid (407 g) which was recrystallized from 1.1 L of ethyl acetate/heptane (1:10 by volume). The product was isolated by filtration (at −80° C. ), washed with 1.6 L of cold (−10° C. ) ethyl acetate/heptane (1:10 by volume) and air-dried to give 339 g (88% yield) of βS-2-[Bis(phenylmethyl)amino]benzene-propanol, Mp=71.5–73.0° C. More product can be obtained from the mother liquor if necessary. The other analytical characterization was identical to compound prepared as described in Method 1.

EXAMPLE 2

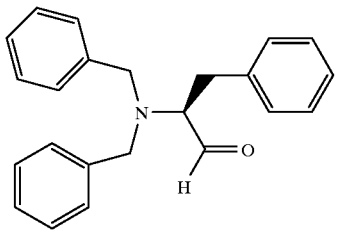

Preparation of 2S-[Bis(phenylmethyl)amino]benzenepropanaldehyde

Method 1

2S-[Bis(phenylmethyl)amino]benzene-propanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. (addition time—1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenched with 1.6 L of cold water (10–15° C.) over 45 minutes. The resultant solution was extracted with ethyl acetate (2.0 L), washed with 5% citric acid (2.0 L), and brine (2.2 L), dried over $MgSO_4$ (280 g) and filtered. The solvent was removed on a rotary evaporator at 35–40° C. and then dried under vacuum to give 198.8 g of 2S-[Bis-(phenylmethyl)amino] benzenepropanaldehyde as a pale yellow oil (99.9%). The crude product obtained was pure enough to be used directly in the next step without purification. The analytical data of the compound were consistent with the published literature. $[α]_D25$=−92.9° (c 1.87, $CH_2Cl_2$); $^1$H NMR (400 MHz, $CDCl_3$) δ, 2.94 and 3.15 (ABX-System, 2H, $J_{AB}$=13.9 Hz, $J_{AX}$=7.3 Hz and $J_{BX}$=6.2 Hz), 3.56 (t, 1H, 7.1 Hz), 3.69 and 3.82 (AB-System, 4H, $J_{AB}$=13.7 Hz), 7.25 (m, 15H) and 9.72 (s, 1H); HRMS Calcd for (M+1) $C_{23}H_{24}NO$ 330.450, found: 330.1836. Anal. Calcd. for $C_{23}H_{23}ON$: C, 83.86; H, 7.04; N, 4.25. Found: C, 83.64; H, 7.42; N, 4.19. HPLC on chiral stationary phase:(S,S) Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enantiomer 10.62 min.

Method 2

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time ~1.25 hr). The mixture was stirred for 5 min. followed by addition of a solution of βS-2-[bis(phenylmethyl)amino]benzene-propanol (0.074 mol) in 100 ml of dichloromethane (addition time −20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give αS-[bis(phenylmethyl)amino] benzenepropanaldehyde. The aldehyde was carried on to the next step without purification.

Method 3

To a mixture of 1.0 g (3.0 mmoles) of βS-2-[bis (phenylmethyl)amino]benzenepropanol 0.531 g (4.53 mmoles) of N-methyl morpholine, 2.27 g of molecular sieves(4A) and 9.1 mL of acetonitrile was added 53 mg (0.15 mmoles) of tetrapropylammonium perruthenate (TPAP). The mixture was stirred for 40 minutes at room temperature and concentrated under reduced pressure. The residue was suspended in 15 mL of ethyl acetate, filtered through a pad of silica gel. The filtrate was concentrated under reduced pressure to give a product containing approximately 50% of αS-2-[bis(phenylmethyl)amino]benzene propanaldehyde as a pale yellow oil.

Method 4

To a solution of 1.0 g (3.02 mmoles) of βS-2-[bis (phenylmethyl)amino]benzenepropanol in 9.0 mL of toluene was added 4.69 mg (0.03 mmoles) of 2,2,6,6-tetramethyl-1-piperidinyloxy, free radical (TEMPO), 0.32 g (3.11 mmoles) of sodium bromide, 9.0 mL of ethyl acetate and 1.5 mL of water. The mixture was cooled to 0° C. and an aqueous solution of 2.87 mL of 5% household bleach containing 0.735 g (8.75 mmoles) of sodium bicarbonate and 8.53 mL of water was added slowly over 25 minutes. The mixture was stirred at 0° C. for 60 minutes. Two more additions (1.44 mL each) of bleach was added followed by stirring for 10 minutes. The two phase mixture was allowed to separate. The aqueous layer was extracted twice with 20 mL of ethyl acetate. The combined organic layer was washed with 4.0 mL of a solution containing 25 mg of potassium iodide and water (4.0 mL), 20 mL of 10% aqueous sodium thiosulfate solution and then brine solution. The organic solution was dried over magnesium sulfate, filtered and concentrated under reduced pressure to give 1.34 g of crude oil containing a small amount of the desired product aldehyde, αS-[bis(phenylmethyl)amino] benzenepropanaldehyde.

Method 5

Following the same procedures as described in Method 1 of this Example except 3.0 equivalents of sulfur trioxide pyridine complex was used and αS-[bis(phenylmethyl) amino]benzenepropanaldehyde was isolated in comparable yields.

EXAMPLE 3

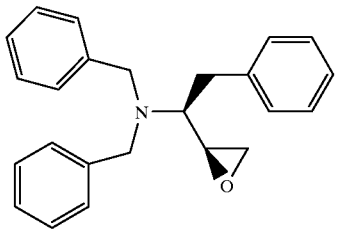

Preparation of N,N-dibenzyl-3(S)-amino-1,2-(S)-epoxy-4-phenylbutane

Method 1

A solution of αS-(Bis(phenylmethyl)amino] benzenepropanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyl lithium in hexane (1.6 M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyl lithium (110 mL) at <−25° C. After addition the mixture was stirred at −30 to −35° C. for 10 minutes. This was repeated once. (2) Additional chloroiodomethane (8.5 mL, 0.11 mol) was added, followed by n-butyl lithium (55 mL, 0.088 mol) at <−25° C. After addition the mixture was stirred at −30 to −35° C. for 10 minutes. This was repeated 5 times. (3) Additional chloroiodomethane (8.5 mL, 0.11 mol) was added, followed by n-butyl lithium (37 mL, 0.059 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR:(2S)/(2R):86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N,αS-Tris(phenylmethyl)-2S-oxiranemethanamine $^1$H NMR (400 MHz, CDCl$_3$) ∂ 2.49 and 2.51 (AB-System, 1H, J$_{AB}$=2.82), 2.76 and 2.77 (AB-System, 1H, J$_{AB}$=4.03), 2.83 (m, 2H), 2.99 & 3.03 (AB-System, 1H, J$_{AB}$=10.1 Hz), 3.15 (m, 1H), 3.73 & 3.84 (AB-System, 4H, J$_{AB}$=14.00), 7.21 (m, 15H); $^{13}$C NMR (400 MHz,CDCl$_3$) ∂ 139.55, 129.45, 128.42, 128.14, 128.09, 126.84, 125.97, 60.32, 54.23, 52.13, 45.99, 33.76; HRMS Calcd for C$_{24}$H$_{26}$NO (M+1) 344.477, found 344.2003.

N,N,αS-Tris(phenylmethyl)-2R-oxiranemethanamine $^1$H NMR (300 MHz, CDCl$_3$) ∂ 2.20 (m, 1H), 2.59 (m, 1H), 2.75 (m, 2H), 2.97 (m, 1H), 3.14 (m, 1H), 3.85 (AB-System, 4H), 7.25 (m, 15H).HPLC on chiral stationary phase: Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of(8): 9.38 min., retention time of enantiomer of (4): 13.75 min.

Method 2

A solution of the crude aldehyde 0.074 mol and chloroiodomethane (7.0 ml, 0.096 mol) in tetrahydrofuran (285 ml) was cooled to −78° C., under a nitrogen atmosphere. A 1.6 M solution of n-butyl lithium in hexane (25 ml, 0.040 mol) was then added at a rate to maintain the temperature at −75° C. (addition time—15 min.). After the first addition, additional chloroiodomethane (1.6 ml, 0.022 mol) was added again, followed by n-butyl lithium (23 ml, 0.037 mol), keeping the temperature at −75° C. The mixture was stirred for 15 min. Each of the reagents, chloroiodomethane (0.70 ml, 0.010 mol) and n-butyl lithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

Method 3

A solution of αS-[Bis(phenylmethyl)amino]benzene-propanaldehyde (178.84 g, 0.54 mol) and bromochloromethane (46 mL, 0.71 mol) in tetrahydrofuran (1.8 L) was cooled to −30 to −35° C. (colder temperature such as −70°

C. also worked well but warmer temperatures are more readily achieved in large scale operations) in a stainless steel reactor under a nitrogen atmosphere. A solution of n-butyl lithium in hexane (1.6 M, 340 mL, 0.54 mol) was then added at a rate that maintained the temperature below −25° C. After addition the mixture was stirred at −30 to −35° C. for 10 minutes. More additions of reagents were carried out in the following manner: (1) additional bromochloromethane (14 mL) was added, followed by n-butyl lithium (102 mL) at <−25° C. After addition the mixture was stirred at −30 to −35° C. for 10 minutes. This was repeated once. (2) Additional bromochloromethane (7 mL, 0.11 mol) was added, followed by n-butyl lithium (51 mL, 0.082 mol) at <−25° C. After addition the mixture was stirred at −30 to −35° C. for 10 minutes. This was repeated 5 times. (3) Additional bromochloromethane (7 mL, 0.11 mol) was added, followed by n-butyl lithium (51 mL, 0.082 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material.

Method 4

Following the same procedures as described in Method 3 of this Example except the reaction temperatures were at −20° C. The resulting N,N,αS-tris(phenylmethyl)-2S-oxiranemethanamine was a diastereomeric mixture of lesser purity then that of Method 3.

Method 5

Following the same procedures as described in Method 3 of this Example except the reaction temperatures were at −70−−78° C. The resulting N,N,αS-tris(phenylmethyl)-2S-oxiranemethanamine was a diastereomeric mixture, which was used directly in the subsequent steps without purification.

Method 6

Following the same procedures as described in Method 3 of this Example except a continuous addition of bromochloromethane and n-butyl lithium was used at −30 to −35° C. After the reaction and work up procedures as described in Method 3 of this Example, the desired N,N,αS-tris (phenylmethyl)-2S-oxiranemethanamine was isolated in comparable yields and purities.

Method 7

Following the same procedures as described in Method 2 of this Example except dibromomethane was used instead of chloroiodomethane. After the reaction and work up procedures as described in Method 2 of this Example, the desired N,N,αS-tris(phenylmethyl)-2S-oxirane-methanamine was isolated.

EXAMPLE 4

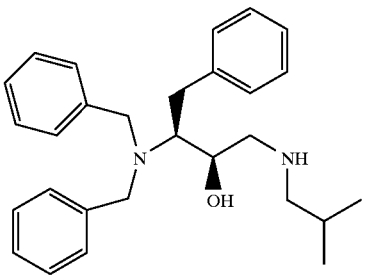

Preparation of N-[3(S)-[N,N-bis(phenylmethyl) amino]-2(R)-hydroxy-4-phenylbutyl]-N-isobutylamine To a solution of crude N,N-dibenzyl-3(S)-amino-1,2(S)-epoxy-4-phenylbutane (388.5 g, 1.13 mol) in isopropanol (2.7 L) (or ethyl acetate) was added isobutylamine (1.7 kgm, 23.1 mol) over 2 min. The temperature increased from 25° C. and to 30° C. The solution was heated to 82° C. and stirred at this temperature for 1.5 hours. The warm solution was concentrated under reduced pressure at 65° C. The brown oil residue was transferred to a 3-L flask and dried in vacuo (0.8 mm Hg) for 16 h to give 450 g of 3S-[N,N-bis(phenylmethyl)amino-4-phenylbutan-2R-ol as a crude oil.

An analytical sample of the desired major diastereomeric product was obtained by purifying a small sample of crude product by silica gel chromatography (40% ethyl acetate/hexane). Tlc analysis: silica gel, 40% ethyl acetate/hexane; Rf=0.28; HPLC analysis: ultrasphere ODS column, 25% triethylamino-/phosphate buffer pH 3-acetonitrile, flow rate 1 mL/min, UV detector; retention time 7.49 min.; HRMS Calcd for $C_{28}H_{27}N_2O$ (M+1) 417.616, found 417.2887. An analytical sample of the minor diastereomeric product, 3S-[N,N-bis(phenylmethyl)amino]1-(2-methylpropyl)amino-4-phenylbutan-2S-ol was also obtained by purifying a small sample of crude product by silica gel chromatography (40% ethyl acetate/hexane).

EXAMPLE 5

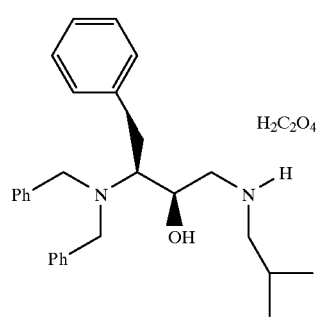

Preparation of N-[3(S)-[N,N-bis(phenylmethyl) amino]-2(R)-hydroxy-4-phenylbutyl]-N-isobutylamine-oxalic acid salt To a solution of oxalic acid (8.08 g, 89.72 mmol) in methanol (76 mL) was added a solution of crude 3(S)-[N, N-bis(phenylmethyl)amino]-1-(2-methylpropyl)amino-4-phenylbutan-2(R)-ol (39.68 g, which contains about 25.44 g (61.06 mmol) of 3(S),2(R) isomer and about 4.49 g (10.78 mmol) of 3(S),2(S) isomer) in ethyl acetate (90 mL) over 15 minutes. The mixture was stirred at room temperature for about 2 hours. Solid was isolated by filtration, washed with ethyl acetate (2×20 mL) and dried in vacuo for about 1 hour to yield 21.86 g (70.7% isomer recovery) of 97% diastereomerically pure salt (based on HPLC peak areas). HPLC analysis: Vydec-peptide/protein C18 column, UV detector 254 nm, flow rate 2 mL/min., gradient (A=0.05% trifluoroacetic acid in water, B=0.05% trifluoroacetic acid in acetonitrile, 0 min. 75% A/25% B, 30 min. 10% A/90% B, 35 min. 10% A/90% B, 37 min. 75% A/25% B); Retention time 10.68 min. (3(S),2(R) isomer) and 9.73 min. (3(S),2(S) isomer). Mp=174.99° C.; Microanalysis: Calc.: C 71.05%, H 7.50%, N 5.53%; Found: C 71.71%, H 7.75%, N 5.39%.

Alternatively, oxalic acid dihydrate (119 g, 0.94 mole) was added to a 5000 mL round bottom flask fitted with a mechanical stirrer and a dropping funnel. Methanol (1000 ml) was added and the mixture stirred until dissolution was complete. A solution of crude 3(S)-(N,N-bis(phenylmethyl) amino]-1-(2-methylpropyl)amino-4-phenylbutan-2(R)-ol in ethyl acetate (1800 ml, 0.212 g amino alcohol isomers/mL, 0.9160 moles) was added over a twenty minute period. The mixture was stirred for 18 hours and the solid product was isolated by centrifugation in six portions at 400 G. Each portion was washed with 125 mL of ethyl acetate. The salt was then collected and dried overnight at 1 torr to yield 336.3 g of product (71% based upon total amino alcohol). HPLC/MS (electrospray) was consistent with the desired product (m/z 417 [M+H]⁺).

Alternatively, crude 3(S)-[N,N-bis(phenylmethyl)amino]-1-(2-methylpropyl)amino-4-phenylbutan-2(R)-ol (5 g) was dissolved in methyl-tert-butylether (MTBE) (10 mL) and oxalic acid (1 g) in methanol (4 mL) was added. The mixture was stirred for about 2 hours. The resulting solid was filtered, washed with cold MTBE and dried to yield 2.1 g of white solid of about 98.9% diastereomerically pure (based on HPLC peak areas).

EXAMPLE 6

Preparation of N-[3(S)-[N,N-bis(phenylmethyl) amino]-2(R)-hydroxy-4-phenylbutyl]-N-isobutylamine.acetic acid salt To a solution of crude 3(S)-[N,N-bis(phenylmethyl) amino]-1-(2-methylpropyl)amino-4-phenylbutan-2(R)-ol in methyl-tert-butylether (MTBE) (45 mL, 1.1 g amino alcohol isomers/mL) was added acetic acid (6.9 mL) dropwise. The mixture was stirred for about 1 hour at room temperature. The solvent was removed in vacuo to yield a brown oil about 85% diastereomerically pure product (based on HPLC peak areas). The brown oil was crystallized as follows: 0.2 g of the oil was dissolved in the first solvent with heat to obtain a clear solution, the second solvent was added until the solution became cloudy, the mixture was heated again to clarity, seeded with about 99% diastereomerically pure product, cooled to room temperature and then stored in a refrigerator overnight. The crystals were filtered, washed with the second solvent and dried. The diastereomeric purity of the crystals was calculated from the HPLC peak areas. The results are shown in Table 1.

TABLE 1

| First Solvent | Second Solvent | Solvent Ratio | Recovery weight (g) | Diastereomeric Purity (%) |
|---|---|---|---|---|
| MTBE | Heptane | 1:10 | 0.13 | 98.3 |
| MTBE | Hexane | 1:10 | 0.03 | 99.6 |
| Methanol | Water | 1:1.5 | 0.05 | 99.5 |
| Toluene | Heptane | 1:10 | 0.14 | 98.7 |
| Toluene | Hexane | 1:10 | 0.10 | 99.7 |

Alternatively, crude 3(S)-[N,N-bis(phenylmethyl)amino]-1-(2-methylpropyl)amino-4-phenylbutan-2(R)-ol (50.0 g, which contains about 30.06 g (76.95 mmol) of 3(S),2(R) isomer and about 5.66 g (13.58 mmol) of 3(S),2(S) isomer} was dissolved in methyl-tert-butylether (45.0 mL). To this solution was added acetic acid (6.90 mL, 120.6 mmol) over a period of about 10 min. The mixture was stirred at room temperature for about 1 hour and concentrated under reduced pressure. The oily residue was purified by recrystallization from methyl-tert-butylether (32 mL) and heptane (320 mL). Solid was isolated by filtration, washed with cold heptane and dried in vacuo for about 1 hour to afford 21.34 g (58.2% isomer recovery) of 96% diastereomerically pure monoacetic acid salt (based on HPLC peak areas). Mp=105–106° C.; Microanalysis: Calc.: C 75.53%, H 8.39%, N 5.87%; Found: C 75.05%, H 8.75%, N 5.71%.

EXAMPLE 7

Preparation of N-[3(S)-[N,N-bis(phenylmethyl) amino]-2(R)-hydroxy-4-phenylbutyl]-N-isobutylamine.L-tartaric acid salt Crude 3(S)-[N,N-bis(phenylmethyl)amino]-1-(2-methylpropyl)amino-4-phenylbutan-2(R)-ol (10.48 g, which contains about 6.72 g (16.13 mmol) of 3(S),2(R) isomer and about 1.19 g (2.85 mmol) of 3(S),2(S) isomer} was dissolved in tetrahydrofuran (10.0 mL). To this solution was added a solution of L-tartaric acid (2.85 g, 19 mmol) in methanol (5.0 mL) over a period of about 5 min. The mixture was stirred at room temperature for about 10 min. and concentrated under reduced pressure. Methyl-tert-butylether (20.0 mL) was added to the oily residue and the mixture was stirred at room temperature for about 1 hour. Solid was isolated by filtration to afford 7.50 g of crude salt. The crude salt was purified by recrystallization from ethyl acetate and heptane at room temperature to yield 4.13 g (45.2% isomer recovery) of 95% diastereomerically pure L-tartaric acid salt (based on HPLC peak areas). Microanalysis: Calc.: C 67.76%, H 7.41%, N 4.94%; Found: C 70.06%, H 7.47%, N 5.07%.

EXAMPLE 8

Preparation of N-[3(S)-[N,N-bis(phenylmethyl) amino]-2(R)-hydroxy-4-phenylbutyl]-N-isobutylamine.dihydrochloric acid salt Crude 3(S)-[N,N-bis(phenylmethyl)amino]-1-(2-methylpropyl)amino-4-phenylbutan-2(R)-ol (10.0 g, which contains about 6.41 g (15.39 mmol) of 3(S),2(R) isomer and about 1.13 g (2.72 mmol) of 3(S),2(S) isomer} was dissolved in tetrahydrofuran (20.0 mL). To this solution was added hydrochloric acid (20 mL, 6.0 N) over a period of about 5 min. The mixture was stirred at room temperature for about 1 hour and concentrated under reduced pressure. The residue was recrystallized from ethanol at 0° C. to yield 3.20 g (42.7% isomer recovery) of 98% diastereomerically pure dihydrochloric acid salt (based on HPLC peak areas). Microanalysis: Calc.: C 68.64%, H 7.76%, N 5.72%; Found: C 68.79%, H 8.07%, N 5.55%.

EXAMPLE 9

Preparation of N-[3(S)-[N,N-bis(phenylmethyl) amino]-2(R)-hydroxy-4-phenylbutyl]-N-isobutylamine.toluenesulfonic acid salt Crude 3(S)-[N,N-bis(phenylmethyl)amino]-1-(2-methylpropyl)amino-4-phenylbutan-2(R)-ol (5.0 g, which contains about 3.18 g (7.63 mmol) of 3(S),2(R) isomer and about 0.56 g (1.35 mmol) of 3(S),2(S) isomer} was dissolved in methyl-tert-butylether (10.0 mL). To this solution was added a solution of toluenesulfonic acid (2.28 g, 12 mmol) in methyl-tert-butylether (2.0 mL) and methanol (2.0 mL) over a period of about 5 min. The mixture was stirred at room temperature for about 2 hours and concentrated under reduced pressure. The residue was recrystallized from methyl-tert-butylether and heptane at 0° C., filtered, washed with cold heptane and dried in vacuo to yield 1.85 g (40.0% isomer recovery) of 97% diastereomerically pure monotoluenesulfonic acid salt (based on HPLC peak areas).

EXAMPLE 10

Preparation of N-[3(S)-[N,N-bis(phenylmethyl) amino]-2(R)-hydroxy-4-phenylbutyl]-N-isobutylamine.methanesulfonic acid salt Crude 3(S)-[N,N-bis(phenylmethyl)amino]-1-(2-methylpropyl)amino-4-phenylbutan-2(R)-ol (10.68 g, which contains about 6.85 g (16.44 mmol) of 3(S),2(R) isomer and about 1.21 g (2.90 mmol) of 3(S),2(S) isomer} was dissolved in tetrahydrofuran (10.0 mL). To this solution was added methanesulfonic acid (1.25 mL, 19.26 mmol). The mixture was stirred at room temperature for about 2 hours and concentrated under reduced pressure. The oily residue was recrystallized from methanol and water at 0° C., filtered, washed with cold methanol/water (1:4) and dried in vacuo to yield 2.40 g (28.5% isomer recovery) of 98% diastereomerically pure monomethanesulfonic acid salt (based on HPLC peak areas).

EXAMPLE 11

Preparation of N-benzyl-L-phenylalaninol
Method 1
L-Phenylalaninol (89.51 g, 0.592 moles) was dissolved in 375 mL of methanol under inert atmosphere, 35.52 g (0.592 moles) of glacial acetic acid and 50 mL of methanol was added followed by a solution of 62.83 g (0.592 moles) of benzaldehyde in 100 mL of methanol. The mixture was cooled to approximately 15° C. and a solution of 134.6 g (2.14 moles) of sodium cyanoborohydride in 700 mL of methanol was added in approximately 40 minutes, keeping the temperature between 15° C. and 25° C. The mixture was stirred at room temperature for 18 hours. The mixture was concentrated under reduced pressure and partitioned between 1 L of 2M ammonium hydroxide solution and 2 L of ether. The ether layer was washed with 1 L of 1M ammonium hydroxide solution, twice with 500 mL water, 500 mL of brine and dried over magnesium sulfate for 1 hour. The ether layer was filtered, concentrated under reduced pressure and the crude solid product was recrystallized from 110 mL of ethyl acetate and 1.3 L of hexane to give 115 g (81% yield) of N-benzyl-L-phenylalaninol as a white solid.

Method 2
L-Phenylalaninol (5 g, 33 mmoles) and 3.59 g (33.83 mmoles) of benzaldehyde were dissolved in 55 mL of 3A ethanol under inert atmosphere in a Parr shaker and the mixture was warmed to 60° C. for 2.7 hours. The mixture was cooled to approximately 25° C. and 0.99 g of 5% platinum on carbon was added and the mixture was hydrogenated at 60 psi of hydrogen and 40° C. for 10 hours. The catalyst was filtered off, the product was concentrated under reduced pressure and the crude solid product was recrystallized from 150 mL of heptane to give 3.83 g (48 % yield) of N-benzyl-L-phenylalaninol as a white solid.

EXAMPLE 12

Preparation of N-(t-Butoxycarbonyl)-N-benzyl-L-phenylalaninol

N-benzyl-L-phenylalaninol (2.9 g, 12 mmoles) was dissolved in 3 mL of triethylamine and 27 mL of methanol and 5.25 g (24.1 mmoles) of di-tert-butyl dicarbonate was added. The mixture was warmed to 60° C. for 35 minutes and concentrated under reduced pressure. The residue was dissolved in 150 mL of ethyl acetate and washed twice with 10 mL of cold (0–5° C.), dilute hydrochloric acid (pH 2.5 to 3), 15 mL of water, 10 mL of brine, dried over magnesium sulfate, filtered and concentrated under reduced pressure. The crude product oil was purified by silica gel chromatography (ethyl acetate: hexane, 12:3 as eluting solvent) to give 3.98 g (97% yield) of colorless oil.

EXAMPLE 13

Preparation of N-(t-Butoxycarbonyl)-N-benzyl-L-phenylalaninal

Method 1
To a solution of 0.32 g (0.94 mmoles) of N-(t-butoxycarbonyl)-N-benzyl-L-phenylalaninol in 2.8 mL of toluene was added 2.4 mg (0.015 mmoles) of 2,2,6,6-tetramethyl-1-piperidinyloxy, free radical (TEMPO), 0.1 g (0.97 mmoles) of sodium bromide, 2.8 mL of ethyl acetate and 0.34 mL of water. The mixture was cooled to 0° C. and an aqueous solution of 4.2 mL of 5% household bleach containing 0.23 g (3.0 mL, 2.738 mmoles) of sodium bicarbonate was added slowly over 30 minutes. The mixture was stirred at 0° C. for 10 minutes. Three more additions (0.4 mL each) of bleach was added followed by stirring for 10 minutes after each addition to consume all the stating material. The two phase mixture was allowed to separate. The aqueous layer was extracted twice with 8 mL of toluene. The combined organic layer was washed with 1.25 mL of a solution containing 0.075 g of potassium iodide, sodium bisulfate (0.125 g) and water (1.1 mL), 1.25 mL of 10% aqueous sodium thiosulfate solution, 1.25 mL of pH 7 phosphate buffer and 1.5 mL of brine solution. The organic solution was dried over magnesium sulfate, filtered and concentrated under reduced pressure to give 0.32 g (100% yield) of N-(t-Butoxycarbonyl)-N-benzyl-L-phenylalaninal.
Method 2
To a solution of 2.38 g (6.98 mmoles) of N-(t-butoxycarbonyl)-N-benzyl-L-phenylalaninol in 3.8 mL (27.2 mmoles) of triethylamine at 10° C. was added a solution of 4.33 g (27.2 mmoles) of sulfur trioxide pyridine complex in 17 mL of dimethyl sulfoxide. The mixture was warmed to room temperature and stirred for one hour. Water (16 mL) was added and the mixture was extracted with 20 mL of ethyl acetate. The organic layer was washed with 20 mL of 5% citric acid, 20 mL of water, 20 mL of brine, dried over magnesium sulfate and filtered. The filtrate was concentrated under reduced pressure to give 2.37 g (100% yield) of N-(t-Butoxycarbonyl)-N-benzyl-L-phenylalaninal.

EXAMPLE 14

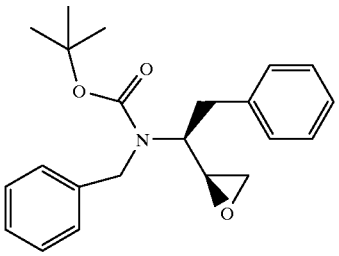

Preparation of 3(S)-[N-(t-butoxycarbonyl)-N-benzylamino]-1,2-(S)-epoxy-4-phenylbutane Method 1

A solution of 2.5 g (7.37 mmoles) of N-(t-butoxycarbonyl)-N-benzyl-L-phenylalaninal and 0.72 mL of chloroiodomethane in 35 mL of THF was cooled to −78° C. A 4.64 mL of a solution of n-butyllithium (1.6 M in hexane, 7.42 mmoles) was added slowly, keeping the temperature below −70° C. The mixture was stirred for 10 minutes between −70 to −75° C. Two additional portions of 0.22 mL of chloroiodomethane and 1.4 mL of n-butyllithium was added sequentially and the mixture was stirred for 10 minutes between −70 to −75° C. after each addition. Four additional portions of 0.11 mL of chloroiodomethane and 0.7 mL of n-butyllithium was added sequentially and the mixture was stirred for 10 minutes between −70 to −75° C. after each addition. The mixture was warmed to room temperature for 3.5 hours. The product was quenched at below 5° C. with 24 mL of ice-cold water. The biphasic layers were separated and the aqueous layer was extracted twice with 30 mL of ethyl acetate. The combined organic layers was washed three times with 10 mL water, then with 10 mL brine, dried over sodium sulfate, filtered and concentrated under reduced pressure to give 2.8 g of a yellow crude oil. This crude oil (>100% yield) is a mixture of the diastereomeric epoxides N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine. The crude mixture is used directly in the next step without purification.

Method 2

To a suspension of 2.92 g (13.28 mmoles) of trimethylsulfoxonium iodide in 45 mL of acetonitrile was added 1.49 g (13.28 mmoles) of potassium t-butoxide. A solution of 3.0 g (8.85 mmoles) of N-(t-butoxycarbonyl)-N-benzyl-L-phenylalaninal in 18 mL of acetonitrile was added and the mixture was stirred at room temperature for one hour. The mixture was diluted with 150 mL of water and extracted twice with 200 mL of ethyl acetate. The organic layers were combined and washed with 100 mL water, 50 mL brine, dried over sodium sulfate, filtered and concentrated under reduced pressure to give 3.0 g of a yellow crude oil. The crude product was purified by silica gel chromatography (ethyl acetate/hexane:1:8 as eluting solvent) to give 1.02 g (32.7% yield) of a mixture of the two diastereomers N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine.

Method 3

To a suspension of 0.90 g (4.42 mmoles) of trimethylsulfonium iodide in 18 mL of acetonitrile was added 0.495 g (4.42 mmoles) of potassium t-butoxide. A solution of 1.0 g (2.95 mmoles) of N-(t-butoxycarbonyl)-N-benzyl-L-phenylalaninal in 7 mL of acetonitrile was added and the mixture was stirred at room temperature for one hour. The mixture was diluted with 80 mL of water and extracted twice with 80 mL of ethyl acetate. The organic layers were combined and washed with 100 mL water, 30 mL brine, dried over sodium sulfate, filtered and concentrated under reduced pressure to give 1.04 g of a yellow crude oil. The crude product was a mixture of the two diastereomers N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine.

EXAMPLE 15

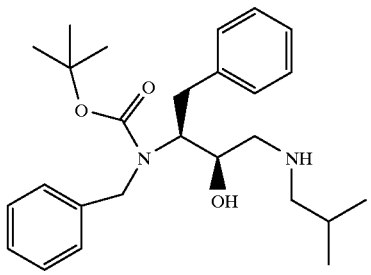

Preparation of 3S-[N-(t-Butoxycarbonyl)-N-(phenylmethyl)amino]-1-(2-methylpropyl)amino-4-phenylbutan-2R-ol To a solution of 500 mg (1.42 mmoles) of the crude epoxide (a mixture of the two diastereomers N,αS-bis(phenylmethyl)-N-(t-butoxycarbonyl)-2S-oxiranemethanamine and N,αS-bis(phenylmethyl)-N-(t-butoxycarbonyl)-2R-oxiranemethanamine) in 0.98 mL of isopropanol was added 0.71 mL (7.14 mmoles) of isobutylamine. The mixture was warmed to reflux at 85° C. to 90° C. for 1.5 hours. The mixture was concentrated under reduced pressure and the product oil was purified by silica gel chromatography (chloroform:methanol, 100:6 as eluting solvents) to give 330 mg of 3S-[N-(t-butoxycarbonyl)-N-(phenylmethyl)amino]-1-(2-methylpropyl)amino-4-phenylbutan-2R-ol as a colorless oil (54.5% yield). 3S-[N-(t-Butoxycarbonyl)-N-(phenylmethyl)amino]-1-(2-methylpropyl)amino-4-phenylbutan-2S-ol was also isolated. When purified N,αS-bis(phenylmethyl)-N-(t-butoxycarbonyl)-2S-oxiranemethanamine was used as starting material, 3S-[N-(t-butoxycarbonyl)-N-(phenylmethyl)amino]-1-(2-methylpropyl)amino-4-phenylbutan-2R-ol was isolated after purification by chromatography in an 86% yield.

EXAMPLE 16

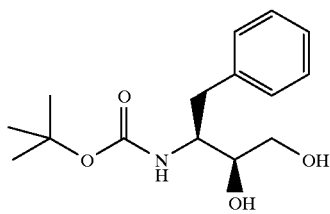

Preparation of 3S-(N-t-Butoxycarbonyl)amino-4-phenylbutan-1,2R-diol

To a solution of 1 g (3.39 mmoles) of 2S-(N-t-butoxycarbonyl)amino-1S-hydroxy-3-phenylbutanoic acid (commercially available from Nippon Kayaku, Japan) in 50 mL of THF at 0° C. was added 50 mL of borane-THF complex (liquid, 1.0 M in THF), keeping the temperatures below 5° C. The reaction mixture was warmed to room temperature and stirred for 16 hours. The mixture was cooled to 0° C. and 20 mL of water was added slowly to destroy the excess $BH_3$ and to quench the product mixture, keeping the temperature below 12° C. The quenched mixture was stirred for 20 minutes and concentrated under reduced pressure. The product mixture was extracted three times with 60 mL of ethyl acetate. The organic layers were combined and washed with 20 mL of water, 25 mL of saturated sodium chloride solution and concentrated under reduced pressure to give 1.1 g of crude oil. The crude product was purified by silica gel chromatography (chloroform/methanol, 10:6 as eluting solvents) to give 900 mg (94.4% yield) of 3S-(N-t-butoxycarbonyl)amino-4-phenylbutan-1,2R-diol as a white solid.

EXAMPLE 17

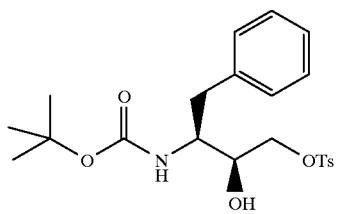

Preparation of 3S-(N-t-Butoxycarbonyl)amino-2R-hydroxy-4-phenylbut-1-yl Toluenesulfonate To a solution of 744.8 mg (2.65 mmoles) of 3S-(N-t-butoxycarbonyl)amino-4-phenylbutan-1,2R-diol in 13 mL of pyridine at 0° C. was added 914 mg of toluenesulfonyl chloride in one portion. The mixture was stirred at 0° C. to 5° C. for 5 hours. A mixture of 6.5 mL of ethyl acetate and 15 mL of 5% aqueous sodium bicarbonate solution was added to the reaction mixture and stirred for 5 minutes. The product mixture was extracted three times with 50 mL of ethyl acetate. The organic layers were combined and washed with 15 mL of water, 10 mL of saturated sodium chloride solution and concentrated under reduced pressure to give about 1.1 g of a yellow chunky solid. The crude product was purified by silica gel chromatography (ethyl acetate/hexane 1:3 as eluting solvents) to give 850 mg (74% yield) of 3S-(N-t-butoxycarbonyl)amino-2R-hydroxy-4-phenylbut-1-yl toluenesulfonate as a white solid.

EXAMPLE 18

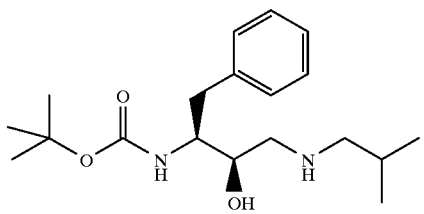

Preparation of 3S-[N-(t-Butoxycarbonyl)amino]-1-(2-methylpropyl)amino-4-phenylbutan-2R-ol To a solution of 90 mg (0.207 mmoles) of 3S-(N-t-butoxycarbonyl)amino-2R-hydroxy-4-phenylbut-1-yl toluenesulfonate in 0.143 mL of isopropanol and 0.5 mL of toluene was added 0.103 mL (1.034 mmoles) of isobutylamine. The mixture was warmed to 80 to 85 ° C. and stirred for 1.5 hours. The product mixture was concentrated under reduced pressure at 40 to 50 ° C. and purified by silica gel chromatography (chloroform/methanol, 10:1 as eluting solvents) to give 54.9 mg (76.8% yield) of 3S-[N-(t-butoxycarbonyl)amino]-1-(2-methylpropyl)amino-4-phenylbutan-2R-ol as a white solid.

EXAMPLE 19

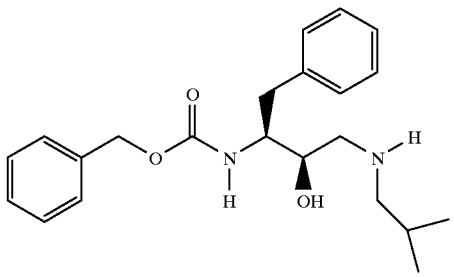

Preparation of N-[3(S)-benzyloxycarbonylamino-2(R)-hydroxy-4-phenylbutyl]-N-isobutylamine Part A To a solution of 75.0 g (0.226 mol) of N-benzyloxycarbonyl-L-phenylalanine chloromethyl ketone in a mixture of 807 mL of methanol and 807 mL of tetrahydrofuran at −2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150–151° C. and M+Li$^+$=340.

Part B

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102–103° C. and MH+298.

Part C

A solution of N-benzyloxycarbonyl 3(S)-amino-1,2-(S)-epoxy-4-phenylbutane (1.00 g, 3.36 mmol) and isobutylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N-[[3(S)-phenylmethylcarbamoyl)amino-2(R)-hydroxy-4-phenylbutyl]N-[(2-methylpropyl)]amine, $C_{22}H_{30}N_2O_3$, mp 108.0–109.5° C., MH+m/z=371.

EXAMPLE 20

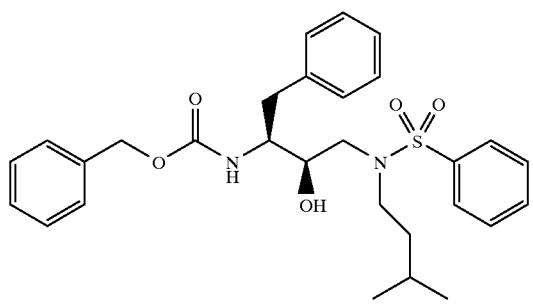

Preparation of phenylmethyl [2R-hydroxy-3-[(3-methylbutyl) (phenylsulfonyl)amino]-1S-(phenylmethyl)propoyl]carbamate From the reaction of N[3(S)-benzyloxycarbonylamino-2(R)-hydroxy-4-phenylbutyl] N-isoamylamine (1.47 gm, 3.8 mmol), triethylamine (528 uL, 3.8 mmol) and benzenesulfonyl chloride (483 uL, 3.8 mmol) one obtains phenylmethyl [2R-hydroxy-3-[(3-methylbutyl)(phenylsulfonyl)amino]-1S-(phenylmethyl)propyl]carbamate. Column chromotography on silica gel eluting with chloroform containing 1% ethanol afforded the pure product. Anal. Calcd for $C_{29}H_{36}N_2O_5S$: C, 66.39; H, 6.92; N, 5.34. Found: C, 66.37; H, 6.93; N, 5.26.

EXAMPLE 21

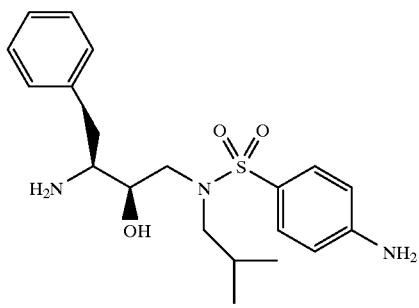

Preparation of 2R-hydroxy-3-[(4-aminophenyl)sulfonyl](2-methylpropyl)amino]-1S-(phenylmethyl) propylamine Part A Preparation of Carbamic acid, 2R-hydroxy-3-[[(4-nitrophenyl)sulfonyl](2-methylpropyl)amino]-1S-(phenylmethyl)propyl-, phenylmethyl ester To a solution of 4.0 g (10.8 mmol) of N-[3S-benzyloxy carbonylamino-2R-hydroxy-4-phenyl]-N-isobutylamine in 50 mL of anhydrous methylene chloride, was added 4.5 mL (3.27 g, 32.4 mmol) of triethylamine. The solution was cooled to 0° C. and 2.63 g (11.9 mmol) of 4-nitrobenzene sulfonyl chloride was added, stirred for 30 minutes at 0° C., then for 1 hour at room temperature. Ethyl acetate was added, washed with 5% citric acid, saturated sodium bicarbonate, brine, dried and concentrated to yield 5.9 g of crude material. This was recrystallized from ethyl acetate/hexane to afford 4.7 g of pure carbamic acid, [2R-hydroxy-3-[[(4-nitrophenyl)sulfonyl](2-methylpropyl)amino]-1S-(phenylmethyl)propyl-, phenylmethyl ester, m/e=556(M+H).

Part B

Preparation of 2R-hydroxy-3-[[(4-aminophenyl)sulfonyl](2-methylpropyl)amino]-1S-(phenylmethyl) propylamine A solution of 3.0 g (5.4 mmol) of carbamic acid, 2R-hydroxy-3-[[(4-nitrophenyl)sulfonyl](2-methylpropyl)amino]-1S-(phenylmethyl)propyl-, phenylmethyl ester in 20 mL of ethyl acetate was hydrogenated over 1.5 g of 10% palladium-on-carbon catalyst under 35 psig of hydrogen for 3.5 hours. The catalyst was removed by filtration and the solution concentrated to afford 2.05 g of the desired 2R-hydroxy-3-[[(4-aminophenyl)sulfonyl](2-methylpropyl)amino]-1S-(phenylmethyl)propylamine, m/e=392 (M+H).

EXAMPLE 22

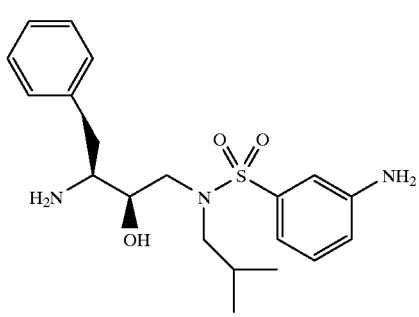

Preparation of 2R-hydroxy-3-[[(3-aminophenyl)sulfonyl](2-methylpropyl)amino]-1S-(phenylmethyl) propylamine

Part A

Preparation of Carbamic acid, [2R-hydroxy-3-[(3-nitrophenylsulfonyl)(2-methylpropyl)amino]-1S-(phenylmethyl)propyl-, phenylmethyl ester To a solution of 1.1 g (3.0 mmol) of N-[3S-benzyloxycarbonylamino-2R-hydroxy-4-phenyl]-N-isobutylamine in 15 mL of anhydrous methylene chloride, was added 1.3 mL (0.94 g, 9.3 mmol) of triethylamine. The solution was cooled to 0° C. and 0.67 g (3.0 mmol) of 3-nitrobenzene sulfonyl chloride was added, stirred for 30 minutes at 0° C., then for 1 hour at room temperature. Ethyl acetate was added, washed with 5% citric acid, saturated sodium bicarbonate, brine, dried and concentrated to yield 1.74 g of crude material. This was recrystallized from ethyl acetate/hexane to afford 1.40 g of pure carbamic acid, [2R-hydroxy-3-[(3-nitrophenylsulfonyl)(2-methylpropyl)amino]-1S-(phenylmethyl)propyl-, phenylmethyl ester, m/e=562(M+Li).

Part B

Preparation of [2R-hydroxy-3-[[(3-aminophenyl)sulfonyl](2-methylpropyl)amino]-1S-(phenylmethyl) propylamine A solution of 1.33 g (2.5 mmol) of carbamic acid, [2R-hydroxy-3-[(3-nitrophenylsulfonyl)(2-methylpropyl)amino]-1S-(phenylmethyl)propyl-, phenylmethyl ester in 40 mL of 1:1 methanol/tetrahydrofuran was hydrogenated over 0.70 g of 10% palladium-on-carbon catalyst under 40 psig of hydrogen for 1.5 hours. The catalyst was removed by filtration and the solution concentrated to afford 0.87 g of the desired [2R-hydroxy-3-[[(3-aminophenyl)sulfonyl](2-methylpropyl)amino]-1S-(phenylmethyl)propylamine.

EXAMPLE 23

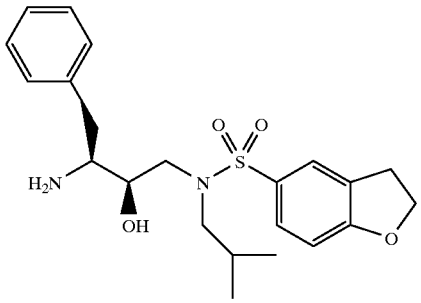

Preparation of 2R-hydroxy-3-[[(2,3-dihydrobenzofuran-5-yl)sulfonyl](2-methylpropyl)amino]-1S-(phenylmethyl)propylamine

Part A

Preparation of 5-(2,3-dihydrobenzofuranyl)sulfonyl chloride

To a solution of 3.35 g of anhydrous N,N-dimethylformamide at 0° C. under nitrogen was added 6.18 g of sulfuryl chloride, whereupon a solid formed. After stirring for 15 minutes, 4.69 g of 2,3-dihydrobenzofuran was added, and the mixture heated at 100° C. for 2 hours. The reaction was cooled, poured into ice water, extracted with methylene chloride, dried over magnesium sulfate, filtered and concentrated the crude material. This was recrystallized from ethyl acetate to afford 2.45 g of 5-(2,3-dihydrobenzofuranyl)sulfonyl chloride.

Part B

Preparation of Carbamic acid, 2R-hydroxy-3-[[(2,3-dihydrobenzofuran-5-yl)sulfonyl](2-methylpropyl)amino]-1S-(phenylmethyl)propyl-, phenylmethyl ester To a solution of 1.11 g (3.0 mmol) of N-[3S-benzyloxycarbonylamino-2R-hydroxy-4-phenyl]-N-isobutylamine in 20 mL of anhydrous methylene chloride, was added 1.3 mL (0.94 g, 9.3 mmol) of triethylamine. The solution was cooled to 0° C. and 0.66 g of 5-(2,3-dihydrobenzofuranyl)sulfonyl chloride was added, stirred for 15 minutes at 0° C., then for 2 hour at room temperature. Ethyl acetate was added, washed with 5% citric acid, saturated sodium bicarbonate, brine, dried and concentrated to yield 1.62 g of crude material. This was recrystallized from diethyl ether to afford 1.17 g of pure carbamic acid, [2R-hydroxy-3-[[(2,3-dihydrobenzofuran-5-yl)sulfonyl](2-methylpropyl)amino]-1S-(phenylmethyl)propyl-, phenylmethyl ester.

Part C

Preparation of [2R-hydroxy-3-[[(2,3-dihydrobenzofuran-5-yl)sulfonyl](2-methylpropyl)amino]-1S-(phenylmethyl) propylamine A solution of 2.86 g of carbamic acid, [2R-hydroxy-3-[[(2,3-dihydrobenzofuran-5-yl)sulfonyl](2-methylpropyl)amino]-1S-(phenylmethyl)propyl-, phenylmethyl ester in 30 mL of tetrahydrofuran was hydrogenated 0.99 g of 10% palladium-on-carbon under 50 psig of hydrogen for 16 hours. The catalyst was removed by filtration and the filtrate concentrated to afford 1.99 g of the desired [2R-hydroxy-3-[[(2,3-dihydrobenzofuran-5-yl)sulfonyl](2-methylpropyl)amino]-1S-(phenylmethyl)propylamine.

EXAMPLE 24

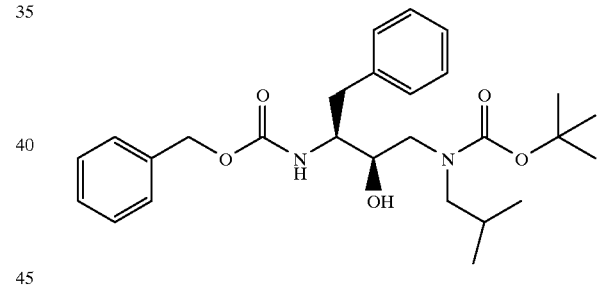

Preparation of N-[(1,1-dimethylethoxyl)carbonyl]-N-[2-methylpropyl]-3S-[N$^1$-(phenylmethoxycarbonyl)amino]-2R-hydroxy-4-phenylbutylamine To a solution of 7.51 g (20.3 mmol) of N-[3S-[(phenylmethoxycarbonyl)amino]-2R-hydroxy-4-phenylbutyl]-2-methylpropylamine in 67 mL of anhydrous tetrahydrofuran was added 2.25 g (22.3 mmol) of triethylamine. After cooling to 0° C., 4.4 g (20.3 mmol) of di-tert-butyldicarbonate was added and stirring continued at room temperature for 21 hours. The volatiles were removed in vacuo, ethyl acetate added, then washed with 5% citric acid, saturated sodium bicarbonate, brine, dried over magnesium sulfate, filtered and concentrated to afford 9.6 g of crude product. Chromatography on silica gel using 30% ethyl acetate/hexane afforded 8.2 g of pure N-[[3S-(phenylmethylcarbamoyl)amino]-2R-hydroxy-4-phenyl]-1-[(2-methylpropyl)amino-2-(1,1-dimethylethoxyl)carbonyl]butane, mass spectum m/e =477 (M+Li).

EXAMPLE 25

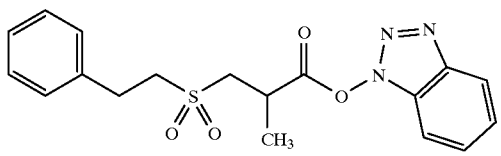

Preparation of 2-methyl-3-[(2-phenylethyl)sulfonyl] propionic acid N-hydroxybenzotriazole ester Part A A solution of methyl methacrylate (7.25 g, 72.5 mmol) and phenethyl mercaptan (10.0 g, 72.5 mmol) in 100 mL of methanol was cooled in an ice bath and treated with sodium methoxide (100 mg, 1.85 mmol). The solution was stirred under nitrogen for 3 h and then concentrated in vacuo to give an oil that was taken up in ether and washed with 1 N aqueous potassium hydrogen sulfate, saturated aqueous sodium chloride, dried over anhydrous magnesium sulfate, filtered and concentrated to give 16.83 g, 97.5% of methyl 2-(R,S)-methyl-4-thia-6-phenyl hexanoate as an oil. TLC on SiO$_2$ eluting with 20:1 hexane:ethyl acetate (v:v) R$_f$=0.41. Alternatively, one can use methyl 3-bromo-2-methyl propionate in place of methyl methacrylate.

Part B

A solution of methyl 2-(R,S)-methyl-4-thia-6-phenyl hexanoate (4.00 g, 16.8 mmol) in 100 mL of dichloromethane was stirred at room temperature and treated portion wise with meta-chloroperoxybenzoic acid (7.38 g, 39.2 mmol) over approximately 40 m. The solution was stirred at room temperature for 16 h and then filtered and the filtrate washed with saturated aqueous sodium bicarbonate, 1N sodium hydroxide, saturated aqueous sodium chloride, dried over anhydrous magnesium sulfate, filtered, and concentrated to give 4.50 g, 99% of desired sulfone. The unpurified sulfone was dissolved in 100 mL of tetrahydrofuran and treated with a solution of lithium hydroxide (1.04 g, 24.5 mmol) in 40 mL of water. The solution was stirred at room temperature for 2 m and then concentrated in vacuo. The residue was then acidified with 1N aqueous potassium hydrogen sulfate to pH=1 and then extracted three times with ethyl acetate. The combined ethyl acetate solution was washed with saturated aqueous sodium chloride, dried over anhydrous magnesium sulfate, filtered and concentrated to give a white solid. The solid was taken up in boiling ethyl acetate/hexane and allowed to stand undisturbed whereupon white needles formed that were isolated by filtration and air dried to give 3.38 g, 79% of 2-(R,S)-methyl-3(β-phenethylsulfonyl)-propionic acid, rmp 91–93° C.

Part C

A solution of 2-(R,S)-methyl-3(β-phenethylsulfonyl)-propionic acid (166.1 mg, 0.65 mmol), N-hydroxybenzotriazole (HOBT) (146.9 mg, 0.97 mmol), and 1-(3-dimethylaminopropyl)-3-ethylcarbodiimide hydrochloride (EDC) (145.8 mg, 0.75 mmol) in 4 mL of anhydrous dimethylformamide (DMF) cooled to 0° C. and stirred under nitrogen for 0.5 h. This solution is then treated with a desired protected amino or sulfonamide isostere intermediate and stirred at room temperature for 16 h. The solution is poured into 30 mL of 60% saturated aqueous sodium bicarbonate solution. The aqueous solution is then decanted from the organic residue. The organic residue is taken up in dichloromethane and washed with 10% aqueous citric acid, brine, dried over anhydrous magnesium sulfate, filtered and concentrated. Flash chromatography of the mixture on silica gel eluting with 1:1 hexane:ethyl acetate can be utilized and will afford the separated diastereomers.

EXAMPLE 26

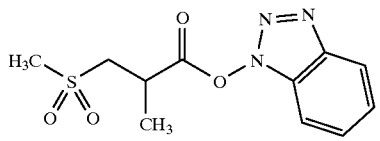

Preparation of 2-methyl-3-(methylsulfonyl) propionic acid N-hydroxybenzotriazole ester Part A A solution of methyl 2-(bromomethyl)-acrylate (26.4 g, 0.148 mol) in 100 mL of methanol was treated with sodium methanesulfinate (15.1 g, 0.148 mol) portion wise over 10 m at room temperature. The solution was then stirred at room temperature for a period of 1.25 h and the solution concentrated in vacuo. The residue was then taken up in water and extracted four times with ethyl acetate. The combined ethyl acetate solution was washed with saturated sodium chloride, dried over anhydrous magnesium sulfate, filtered and concentrated to give a white solid, 20.7 g which was taken up in boiling acetone/methyl tert-butyl ether and allowed to stand whereupon crystals of pure methyl 2-(methylsulfonylmethyl) acrylate 18.0 g, 68% formed, mp 65–68 0° C.

Part B

A solution of methyl 2-(methylsulfonylmethyl)acrylate (970 mg, 5.44 mmol) in 15 mL of tetrahydrofuran was treated with a solution of lithium hydroxide (270 mg, 6.4 mmol) in 7 mL of water. The solution was stirred at room temperature for 5 m and then acidified to pH=1 with 1 N aqueous potassium hydrogen sulfate and the solution extracted three times with ethyl acetate. The combined ethyl acetate solution was dried over anhydrous magnesium sulfate, filtered, and concentrated to give 793 mg, 89% of 2-(methylsulfonylmethyl) acrylic acid, mp 147–149 0° C.

Part C

A solution of 2-(methylsulfonylmethyl)acrylic acid (700 mg, 4.26 mmol) in 20 mL of methanol was charged into a Fisher-Porter bottle along with 10% palladium on carbon catalyst under a nitrogen atmosphere. The reaction vessel was sealed and flushed five times with nitrogen and then five times with hydrogen. The pressure was maintained at 50 psig for 16 h and then the hydrogen was replaced with nitrogen and the solution filtered through a pad of celite to remove the catalyst and the filterate concentrated in vacuo to give 682 mg 96% of 2-(R,S)-methyl-3-methylsulfonyl propionic acid.

Part D

A solution of 2-(R,S)-methyl-3(methylsulfonyl)propionic acid (263.5 mg, 1.585 mmol), N-hydroxybenzotriazole (HOBT) (322.2 mg, 2.13 mmol), and 1-(3-dimethylaminopropyl)-3-ethylcarbodiimide hydrochloride (EDC) (339.1 mg, 1.74 mmol) in 4 mL of anhydrous dimethylformamide (DMF) is cooled to 0° C. and stirred under nitrogen for 0.5 h. This solution is then treated with a desired protected amino or sulfonamide isostere intermediate and stirred at room temperature for 16 h. The solution is poured into 60 mL of 60% saturated aqueous sodium bicarbonate solution. The aqueous solution is then decanted from the organic residue. The organic residue is taken up in dichloromethane and washed with 10% aqueous citric acid, brine, dried over anhydrous magnesium sulfate, filtered and concentrated to give the desired product.

EXAMPLE 26A

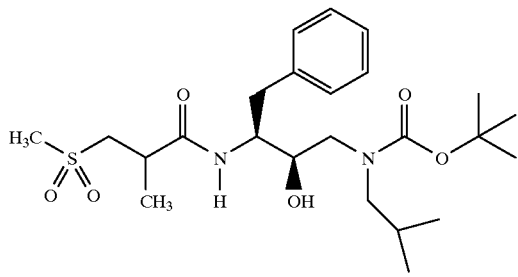

Preparation of N-[2R-hydroxy-3-[[1,1-dimethylethoxy)carbonyl](2-methylpropyl)amino]-1S-(phenylmethyl)propyl]-2-R,S-methyl-3-(methylsulfonyl)propanamide Part A
N-[(1,1-dimethylethoxyl)carbonyl]-N-[2-methylpropyl]-3S-[N¹-(phenylmethoxycarbonyl)amino]-2R-hydroxy-4-phenylbutylamine

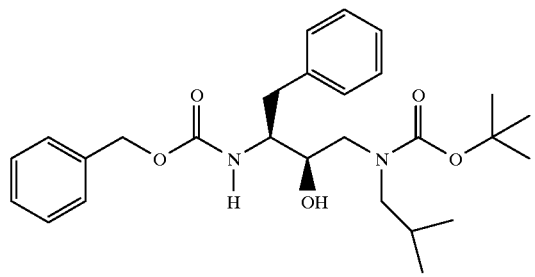

from Example 24 dissolved in ethanol was hydrogenated at 45 psi of hydrogen in the presence of 5% Pd(C) catalyst to yield N-[(1,1-dimethylethoxyl)carbonyl]-N-[2-methylpropyl]-3S-[N¹-amino]-2R-hydroxy-4-phenylbutylamine. Following standard workup by filtration of the 5% Pd(C) catalyst and evaporation of the filtrate solvent under reduced pressure using a rotary evaporator, the amine was obtained

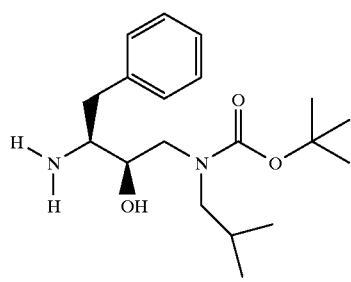

Part B
The amine from Part A is reacted in DMF with 2-methyl-3-(methylsulfonyl)propionic acid N-hydroxybenzotriazole ester from Example 26 at or about room temperature. The solution is washed with sodium bicarbonate solution and extracted with ethyl acetate. The ethyl acetate extract is washed with citric acid solution, brine and is dried over sodium sulfate. The drying agent is filtered and the organic solvent is removed to provide product

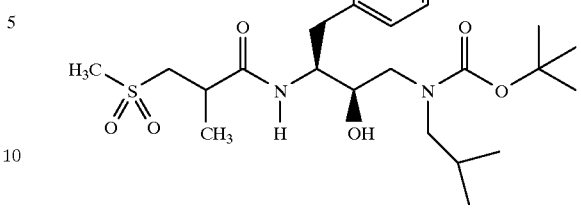

EXAMPLE 26B

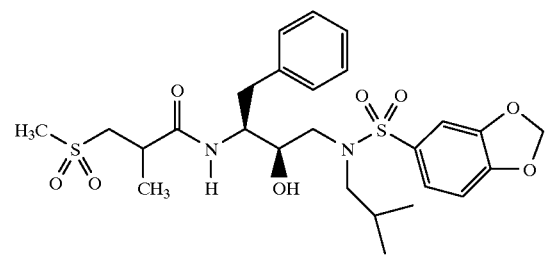

Preparation of N-[2R-hydroxy-3-[(2-methypropyl)[1,3-benzodioxol-5-yl)sulfonyl]amino]-1S-(phenylmethyl)propyl]-3S-[2-R,S-methyl-3-(methylsulfonyl)]propanamide N-[2R-hydroxy-3-[[(1,1-dimethylethoxy) carbonyl](2-methylpropyl)amino]-1S-(phenylmethyl)propyl]-3S-[2-R,S-methyl-3-(methylsulfonyl)]propanamide (Example 26A) is dissolved in dioxane/HCl and it is stirred for about 2 hours at room temperature. The solvent is removed and the residue is dried in vacuo to produce the amine

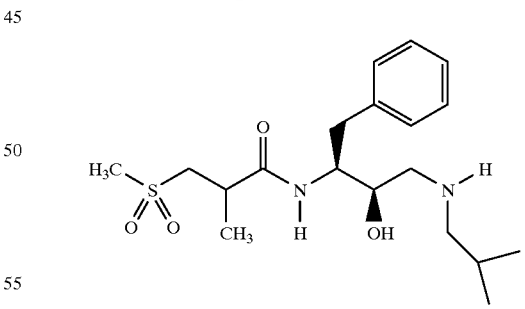

The residue is stirred in ethyl acetate, 1,3-benzodioxol-5-yl sulfonyl chloride is added followed by triethylamine and the mixture is stirred at about room temperature. The reaction mixture is diluted with ethyl acetate, is washed with saturated sodium bicarbonate (saturated) and brine, dried (MgSO₄) and concentrated to provide product. The residue is chromatographed if further purification and/or separation of the isomer (e.g., see below) is desired.

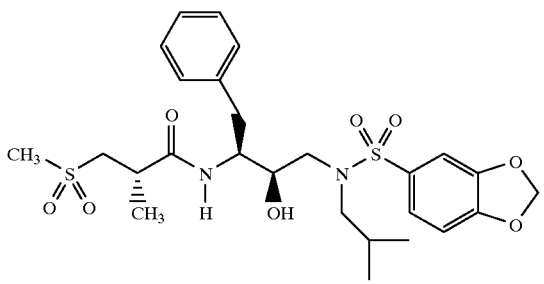

EXAMPLE 27

Preparation of Sulfone Inhibitors From L-(+)-S-acetyl-β-mercaptoisobutyric Acid

Part A

A round-bottomed flask is charged with the desired protected amino or sulfonamide isostere intermediate (2.575 mmol) and coupled to L-(+)-S-acetyl-b-mercapto butyric acid in the presence of 1-(3-dimethylaminopropyl)-3-ethylcarbodiimide hydrochloride (EDC) (339.1 mg, 1.74 mmol), in 10 mL of $CH_2Cl_2$ and is allowed to stir at room temperature for 16 h. The solution is concentrated in vacuo and the residue taken up in ethyl acetate, washed with 1N $KHSO_4$, sat. aq. $NaHCO_3$, brine, dried over anhydrous $MgSO_4$, filtered and concentrated to give an oil which can be purified by radial chromatography on $SiO_2$ eluting with ethyl acetate to give the pure product.

Part B

A solution of the product of Part A (0.85 mmol) in 10 mL of methanol is treated with anhydrous ammonia for ca. 1 m at 0° C. The solution is stirred at that temperature for 16 h and then concentrated in vacuo to give the desired product that can be used directly in the next step without further purification.

Part C

A solution of the product of Part B (0.841 mmol) in 10 mL of dry toluene under nitrogen is treated in rapid succession with 1,8-diazabicyclo[5.4.0]undec-7-ene, (DBU), (128.1 mg. 0.841 mmol) and iodomethane (119.0 mg, 0.841 mmol). After 0.5 h at room temperature the reaction is diluted with ethyl acetate washed with 1N $KHSO_4$, sat. aq. $NaHCO_3$, brine. After the solution is dried over anhydrous $MgSO_4$, filtered and concentrated in vacuo the desired product is obtained and can be used directly in the next step.

Part D

A solution of the product of Part C (0.73 mmol) and sodium perborate (500 mg, 3.25 mmol) in 30 mL of glacial acetic acid is warmed to 55° C. for 16 h. The solution is concentrated in vacuo and then the residue is taken up in ethyl acetate, washed with water, sat. aq. $NaHCO_3$, brine, dried over anhydrous $MgSO_4$, filtered and concentrated to give the desired product.

General Procedure for Coupling Sulfonyl Compounds to Sulfonamides

A mixture of the sulfonyl alkanoyl compound (approximately 1 mmol), N-hydroxybenzotriazole (1.5 mmol), and 1-(3-dimethylaminopropyl)-3-ethylcarbodiimide hydrochloride (EDC) (1.2 mmol) is dissolved in a suitable solvent such as DMF and allowed to react for about 30 min. at 0° C. A desired protected amino or sulfonamide isostere intermediate (1.05 mmol) is dissolved in DMF, added to the above mixture and stirred at room temperature for a period of time sufficient for the reaction to take place. The solution is then poured into saturated aqueous $NaHCO_3$ and extracted with, for example, ethyl acetate. The extracts are washed, dried, filtered and concentrated. The resulting material is then crystallized from a suitable solvent or solvent mixture such as hexanes and ethyl acetate to produce the product.

EXAMPLE 28

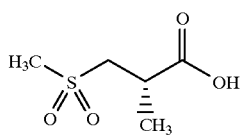

Preparation of 2(S)-methyl-3-(methylsulfonyl) prorionic Acid

Part A

To a solution of 10 g of D-(−)-S-benzoyl-b-mercaptoisobutyric acid t-butyl ester in 20 mL of methanol was bubbled in gaseous ammonia at 0° C. The reaction was allowed to then warm to room temperature, stirred overnight and concentrated under reduced pressure. The resulting mixture of a solid (benzamide) and liquid was filtered to provide 5.21 g of a pale oil which then solidified. This was identified as 2(S)-methyl-3-mercaptopropionic acid t-butyl ester.

Part B

To a solution of 5.21 g of 2(S)-methyl-3-mercaptopropionic acid t-butyl ester in 75 mL of toluene at 0° C. was added 4.50 g of 1,8-diazabicyclo[5.40]undec-7-ene and 1.94 mL of methyl iodide. After stirring at room temperature for 2.5 hours, the volatiles were removed, ethyl acetate added, washed with dilute hydrochloric acid, water, brine, dried and concentrated to afford 2.82 g of a pale oil, identified as 2(S)-methyl-3-(thiomethyl)propionic acid t-butyl ester.

Part C

To a solution of 2.82 g of 2(S)-methyl-3-(thiomethyl) propionic acid t-butyl ester in 50 mL of acetic acid was added 5.58 g of sodium perborate and the mixture heated to 55° C. for 17 hours. The reaction was poured into water, extracted with methylene chloride, washed with aqueous sodium bicarbonate, dried and concentrated to afford 2.68 g of 2(S)-methyl-3-(methylsulfonyl)propionic acid t-butyl ester as a white solid.

Part D

To 2.68 g of 2(S)-methyl-3-(methylsulfonyl)propionic acid t-butyl ester was added 20 mL of 4N hydrochloric acid/dioxane and the mixture stirred at room temperature for 19 hours. The solvent was removed under reduced pressure to afford 2.18 g of crude product, which was recrystallized from ethyl acetate/hexane to yield 1.44 g of 2(S)-methyl-3-(methylsulfonyl)propionic acid as white crystals.

EXAMPLE 29

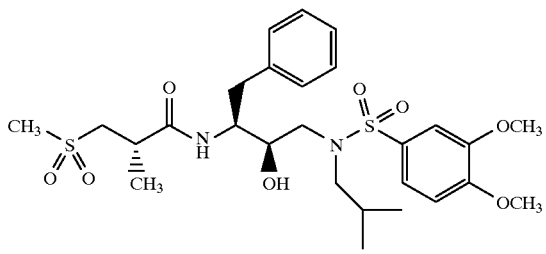

Preparation of [1S-[1R*(R*),2S*]]-N-[2-hydroxy-3-[(2-methylpropyl)(3,4-dimethoxyphenylsulfonyl)amino]-1-(phenylmethyl)propyl]-2-methyl-3-(methylsulfonyl)propanamide Part A A solution of N-benzyloxycarbonyl-3(S)-amino-1,2-(S)-epoxy-4-phenylbutane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N-[3(S)-benzyloxycarbonylamino-2(R)-hydroxy-4-phenyl] N-isobutylamine, mp 108.0–109.5 ° C., MH+m/z=371.

Part B

A solution of N-[3(S)-benzyloxycarbonylamino-2(R)-hydroxy-4-phenyl]N-isobutylamine (1.5356 g, 4.14 mmol) and triethylamine (522 mg, 5.17 mmol) in 15 mL of dichloromethane was treated with 3,4-dimethoxybenzenesulfonyl chloride (1.0087 g, 4.26 mmol) at room temperature for 14 h. The solvent was removed in vacuo and the residue taken up in ethyl acetate and then washed with 1N KHSO$_4$, saturated aqueous NaHCO$_3$, brine, dried over anhyd MgSO$_4$, filtered and concentrated to give 2.147 g, 90.5%, of a white solid, mp 124–127° C., HRFAB MS; M+Li; calc'd. for C$_{30}$H$_{38}$N$_2$O$_7$S+Li: 577.2560. Found: 577.2604.

Part C

A solution of carbamic acid, product from Part B (513 mg, 0.90 mmol) in 30 mL of methanol was stirred with 20 mg of palladium black catalyst and 10 mL of formic acid for 15 h at room temperature. The catalyst was removed by filtration through diatomaceous earth and the filtrate concentrated in vacuo and the residue taken up in ethyl acetate. The ethyl acetate solution was washed with saturated aqueous NaHCO$_3$, brine and dried over anhyd MgSO$_4$, filtered and concentrated in vacuo to give a white solid, 386 mg, 98%, mp 123–130° C., FAB MS; M+Li$^+$=443, that was used directly in the next step without further purification.

Part D

A mixture of 2(S)-methyl-3-methylsulfonyl propionic acid (128 mg, 0.77 mmol), N-hydroxybenzotriazole hydrochloride (EDC) (177.3 mg, 0.92 mmol) was dissolved in 1.5 mL of dimethylformamide (DMF) and allowed to react for 30 min at 0° C. The amine from Part C (359 mg, 0.82 mmol) dissolved in 1 mL of DMF was added to the above mixture and stirred at room temperature for 48 h. The solution was then poured into 75 mL of saturated aqueous NaHCO$_3$ and extracted with ethyl acetate. The ethyl acetate extracts were washed with 5% aqueous citric acid, saturated aqueous NaHCO$_3$, brine, dried over anhyd MgSO$_4$, filtered and concentrated to give a clear oil, 220 mg. The material was crystallized from hexanes and ethyl acetate to give 178 mg, 40% of pure product with mp 130–133° C. HRFAB MS;M+Li$^+$; calc'd. for C$_{27}$H$_{40}$N$_2$O$_8$S$_2$Li: 591.2386. Found: 591.2396.

EXAMPLE 30

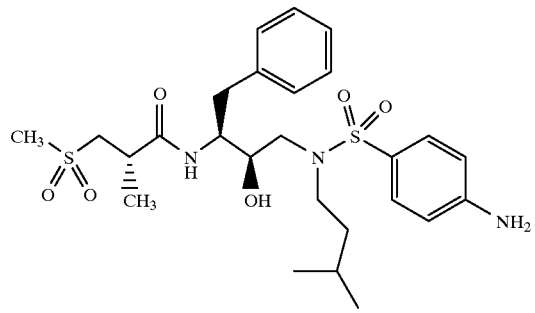

Preparation of [1S-[1R*(R*),2S*]]-N-[2-hydroxy-3-](3-methylbutyl) (4-aminophenylsulfonyl)amino]-1-(phenylmethyl)-propyl]-2-methyl-3-1 methylsulfonyl)propanamide Part A A solution of N-benzyloxycarbonyl-3(S)-amino-1,2(S) epoxy-4-phenylbutane (11.54 g, 38.81 mmol) and isoamylamine (66.90 g, .767 mol, 19.9 equivalents) in 90 mL of isopropyl alcohol was heated to reflux for 3.1 h. The solution was cooled to room temperature and partially concentrated in vacuo and the remaining solution poured into 200 mL of stirring hexanes whereupon the product crystallized from solution. The product was isolated by filtration and air dried to give 11.76 g, 79% of N-[[3(S)-phenylmethoxy)carbonyl)amino-2 (R)-hydroxy-4-phenylbutyl]N-[(3-methylbutyl)] amine, mp 118–122° C., FAB MS: MH$^+$=385.

Part B

A solution of N-[[3(S)-(phenylmethoxycarbonyl)amino-2 (R)-hydroxy-4-phenylbutyl]N-[(3-methylbutyl)]amine (1.1812 g, 3.07 mmol) and triethylamine (325.7 mg, 3.22 mmol) in 20 mL of dichloromethane was treated with 4-nitrobenzensulfonyl chloride (767 mg, 90% purity 3.11 mmol) at room temperature for 10 min. The solvent was removed in vacuo and the residue taken up in ethyl acetate and then washed with 1N KHSO$_4$, saturated aqueous NaHCO$_3$, brine, dried over anhyd MgSO$_4$, filtered and concentrated to give 2.3230 g, of a tan solid, that was crystallized from ethyl acetate and petroleum ether to provide 870 mg, 50%, mp 130–132° C. of pure product, HRFAB MS; M+Li, calc'd. for C$_{29}$H$_{35}$N$_3$O$_7$S+Li: 576.2316. Found: 576.2350.

Part C

A solution of product from Part B (574 mg, 1.01 mmol) in 40 mL of methanol, (the solution was not completely homogeneous), was treated with 70 mg of 10% palladium on carbon catalyst and hydrogenated at 42 psig for 15 h at room temperature. The catalyst was removed by filtration through diatomaceous earth and the filtrate concentrated in vacuo to give a white solid that was crystallized from chloroform, mp 123–127° C., FAB MS; M+Li$^+$=412, 400 mg, 91%, that was used directly in the next step without further purification.

Part D

A mixture of 2(S)-methyl-3-methylsulfonyl propionic acid (112.3 mg, 0.675 mmol), N-hydroxybenzotriazole (159.1 mg, 1.04 mmol), and 1-(3-dimethylaminopropyl)-3-ethylcarbodiimide hydrochloride (EDC) (147.8 mg, 0.77 mmol) was dissolved in 1.0 mL of dimethylformamide

53

(DMF) and allowed to react for 30 min at 0° C. The amine from Part C (261.9 mg, 0.646 mmol) dissolved in 0.5 mL of DMF was added to the above mixture and stirred at room temperature for 16.5 h. The solution was then poured into 75 mL of saturated aqueous NaHCO$_3$ and extracted with ethyl acetate. The ethyl acetate extracts were washed with 5% aqueous citric acid, saturated aqueous NaHCO$_3$, brine, dried over anhyd MgSO$_4$, filtered and concentrated to give a white foam, 326.3 mg. The material was purified by flash chromatography over silica gel eluting with ethyl acetate to provide 213.6 mg, 64% of pure product as a white foam, FAB MS; MH$^+$=554.

EXAMPLE 31

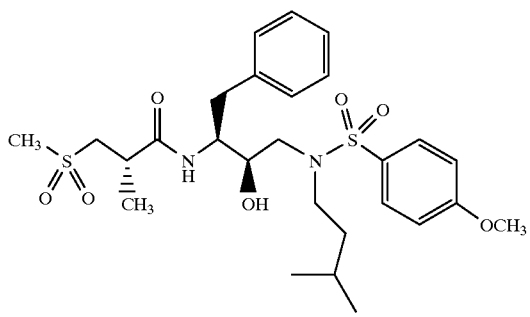

Preparation of [1S-[1R*(R*),2S*]]-N-[2-hydroxy-3-[(3-methylbutyl)(4-methoxyphenylsulfonyl)amino]-1-(phenylmethyl)propyl]-2-methyl-3-(methylsulfonyl)propanamide Part A A solution of N-benzyloxycarbonyl-3(S)-amino-1,2(S) epoxy-4-phenylbutane (11.54 g, 38.81 mmol) and isoamylamine (66.90 g, 0.767 mol, 19.9 equivalents) in 90 mL of isopropyl alcohol was heated to reflux for 3.1 h. The solution was cooled to room temperature and partially concentrated in vacuo and the remaining solution poured into 200 mL of stirring hexanes whereupon the product crystallized from solution. The product was isolated by filtration and air dried to give 11.76 g, 79% of N-[[3(S)-phenylmethoxy)carbonyl) amino-2(R)-hydroxy-4-phenylbutyl]N-[(3-methylbutyl)] amine, mp 118–122° C., FAB MS: MH$^+$=385.

Part B

A solution of N-([3(S)-phenylmethoxy)carbonyl)amino-2 (R)-hydroxy-4-phenylbutyl]N-[(3-methylbutyl)]amine (1.1515 g, 2.99 mmol), and triethylamine (313.5 mg, 3.10 mmol) in 15 mL of dichloromethane was treated with 4-methoxybenzenesulfonyl chloride (630.6 mg, 3.05 mmol) via syringe. The solution was stirred at room temperature for 40 min and then concentrated in vacuo. The residue was dissolved in ethyl acetate and washed with 1N KHSC$_4$, saturated aqueous NaHCO$_3$, brine, dried over anhyd MgSO$_4$, filtered and concentrated to give 1.5622 g, of a white foam. The crude product was purified by recrystallization from a mixture of hexanes and ethyl acetate to give 1.1047 g, 67% of pure product mp 95–98° C. High resolution FAB Mass spectrum calc'd. for $C_{30}H_{38}N_2O_6S$: 555.2529. Found: 555.2559.

Part C

A solution of the product from Part B (970 mg, 1.68 mmol) in 30 mL of methanol was treated with 70 mg of 10% palladium on carbon catalyst and hydrogenated at 41 psig for 16 h at room temperature. The catalyst was removed by filtration and the filtrate concentrated in vacuo to give a clear

54 oil that solidified upon standing, mp 81–85° C., FAB MS; MH$^+$=421, 764.1 mg that was used directly in the next step.

Part D

A mixture of 2(S)-methyl-3-methylsulfonyl propionic acid (194 mg, 1.17 mmol), N-hydroxybenzotriazole (276 mg, 1.34 mmol), and 1-(3-dimethylaminopropyl)-3-ethylcarbodiimide hydrochloride (EDC) (256 mg, 1.34 mmol) was dissolved in 3.5 mL of dimethylformamide (DMF) and allowed to react for 30 min at 0° C. The amine from Part C (451.1 mg, 1.07 mmol) dissolved in 1.5 mL of DMF was added to the above mixture and stirred at room temperature for 16 h. The solution was then poured into 20 mL of saturated aqueous NaHCO$_3$ and extracted 4 times with ethyl acetate. The combined ethyl acetate extracts were washed with 5% aqueous citric acid, saturated aqueous NaHCO$_3$, brine, dried over anhyd MgSO$_4$, filtered and concentrated to give a clear oil that crystallized upon standing. The material was recrystallized from hexanes and ethyl acetate to give 517.6 mg, 85% of pure product with mp 125–129° C. HRFAB MS; calc'd. for $C_{27}H_{40}N_2O_7S_2$: 569.2355. Found: 569.2397.

EXAMPLE 32

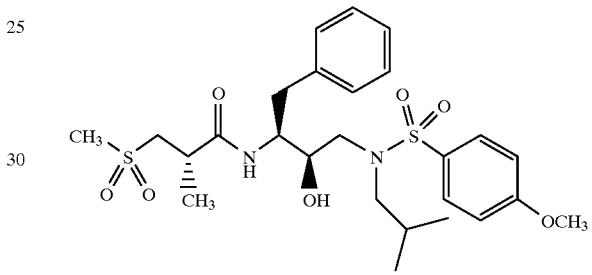

Preparation of [1S-[1R*(R*),2S*]]-N-[2-hydroxy-3-[(2-methylpropyl)(4-methoxyphenylsulfonyl)amino]-1-(phenylmethyl)propyl]-2-methyl-3-(methylsulfonyl)propanamide Part A A solution of N-benzyloxycarbonyl-3(S)-amino-1,2-(S)-epoxy-4-phenylbutane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N-[3(S)-benzyloxycarbonylamino-2(R)-hydroxy-4-phenyl] N-isobutylamine, mp 108.0–109.5 ° C., MH+m/z=371.

Part B

N-[3(S)-benzyloxycarbonylamino-2(R)-hydroxy-4-phenyl]-N-isobutylamine (1.1131 g, 3.00 mmol) and triethylamine (324.0 mg, 3.20 mmol) in 20 mL of dichloromethane was treated with 4-methoxy-benzenesulfonyl chloride (715.4 mg, 3.46 mmol). The solution was stirred at room temperature for 6 h and then was concentrated in vacuo. The residue was dissolved in ethyl acetate and washed with 1N KHSO$_4$, saturated aqueous NaHCO$_3$, brine, dried over anhyd MgSO$_4$, filtered, and concentrated to give a clear oil. The oil was crystallized from ether to give a white solid 1.273 g, 78%, mp 97–10° C., of pure product, FAB MS; MH$^+$=541.

Part C

The product from Part B (930 mg, 1.68 mmol) was dissolved in 30 mL of methanol and hydrogenated at 40 psig over 70 mg of 10% palladium on carbon at room temperature for 17 h. The catalyst was removed by filtration through diatomaceous earth and the filtrate was concentrated in vacuo to give 704 mg of a clear oil, that solidified upon standing, mp 105–110° C., FAB MS, MH⁺=407, and was used directly in the next step without further purification.

Part D

A mixture of 2-methyl-3(methylsulfonyl)propionic acid (174.9 mg, 1.05 mmol), N-hydroxybenzotriazole (230 mg, 1.50 mmol) and EDC (220.5 mg, 1.15 mmol) in 2 mL of DMF was stirred at 0° C. for 0.5 mL and then treated with the amine from Part C (401.2 mg, 0.99 mmol) in 1 mL of DMF. The solution was stirred at room temperature for 16 h and then poured into 20 mL of saturated aqueous NaHCO$_3$. The aqueous solution was extracted with ethyl acetate and then the ethyl acetate solution was washed with 5% aqueous citric acid, saturated aqueous NaHCO$_3$, brine, dried over anhyd MgSO$_4$, filtered and concentrated in vacuo to give a clear oil, 260 mg, which was purified by flash chromatography on Silica gel eluting with hexanes and ethyl acetate to provide 52.7 mg, 9.6%, mp 87–92° C., HRFAB MS; Calc'd for C$_{26}$H$_{38}$N$_2$O$_7$S$_2$: 555.2199. Found: 555.2234.

EXAMPLE 33

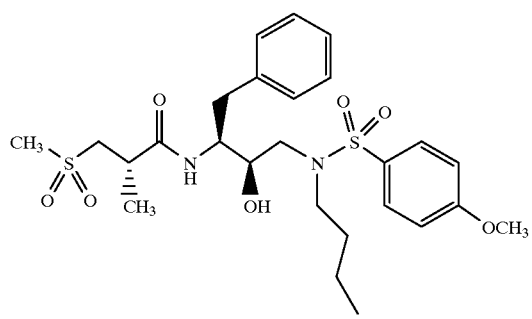

Preparation of [1S-1R*(R*) 2S*]]-N-[2-hydroxy-3-[(butyl)(4-methoxyphenylsulfonyl)amino]-1-(phenylmethyl)propyl]-2-methyl-3-(methylsulfonyl) propanamide Part A From the reaction of (1.48 g, 5.0 mmol) of N-benzyloxycarbonyl 3(S)-amino-1,2-(S)-epoxy-4-phenylbutane and (7.314 g, 100.0 mmol) of n-butylamine, one obtains 1.50 g (80%) of N-[3(S)-benzyloxycarbonylamino-2(R)-hydroxy-4-phenylbutyl]-N-butylamine, mp 125–128° C., FAB MS, Spectrum: MH⁺= 371.

Part B

The amine from Part A (1.52 mg, 4.10 mmol) and triethylamine (488 mg, 4.82 mmol) in 30 mL of dichloromethane was treated with 4-methoxybenzenesulfonyl chloride (869 mg, 4.20 mmol) at room temperature for 3 h. The solution was removed in vacuo and the residue was taken up in ethyl acetate. The ethyl acetate solution was washed with 1N KHSO$_4$, saturated aqueous NaHCO$_3$, brine, dried over anhyd MgSO$_4$, filtered and concentrated to give a white solid that was washed with ether and air dried to provide 1.71 g, 77%, mp 118–120° C., FAB MS; M+Li=547, of pure product.

Part C

The product from Part B (1.514 g, 2.80 mmol) in 30 mL of methanol was hydrogenated at 40 psig over 110 mg of 10% palladium on carbon for 16 h at room temperature. The catalyst was removed by filtration through diatomaceous earth and the filtrate concentrated to give a white solid, 1.20 g, 100%, mp 103–108° C., HRFAB MS; Calc'd for C$_{21}$H$_{30}$N$_2$O$_4$S: 413.2086. Found: 413.2121, which was used directly in the next step without further purification.

Part D

A mixture of 2(S)-methyl-3-(methylsulfonyl)propionic acid (354.4 mg, 2.13 mmol), N-hydroxybenzotriazole (473.4 mg, 3.09 mmol) and EDC (445.3 mg, 2.33 mmol) in 1.5 mL of DMF was stirred at 0° C. for 25 min. and then treated with the amine from Part C (815 mg, 2.00 mmol) in 2 mL of DMF. The mixture was stirred at room temperature for 16 h and then poured into 50 mL of saturated aqueous NaHCO$_3$ and then extracted with ethyl acetate. The ethyl acetate solution was washed with 5% aqueous citric acid, saturated aqueous NaHCO$_3$, brine, dried over anhyd MgSO$_4$, filtered and concentrated in vacuo to give 905 mg of a white foam. The product was purified by flash chromatography on Silica gel eluting with ethyl acetate/hexanes to provide 711.6 mg, 65%, of pure product, mp 87–92° C., HRFAB MS, M+Li; Calc'd for C$_{26}$H$_{38}$N$_2$O$_7$S$_2$Li: 561.2281 Found: 561.2346.

EXAMPLE 34

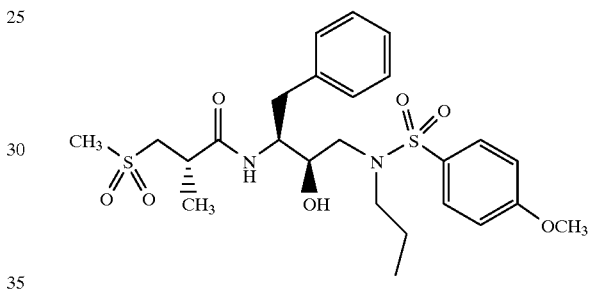

Preparation of [1S-[1R*(R*),2S*]]-N-[2-hydroxy-3-[(propyl)(4-methoxyphenylsulfonyl)amino]-1-(phenylmethyl)propyl]-2-methyl-3-(methylsulfonyl) propanamide Part A A solution of N-benzyloxycarbonyl 3(S)-amino-1,2-(S)-epoxy-4-phenylbutane (6.06 g, 20.4 mmol) and n-propylamine (20.9 g, 0.35 mmol) in 100 mL of isopropyl alcohol was heated to reflux for 3 h. The solution was then concentrated in vacuo to give a solid that was crystallized from hexanes and ethyl acetate to give 6.53 g, 90%, of the desired product, mp 120–123° C., FAB MS: MH⁺=357.

Part B

A solution of the product from Part A (620 mg, 1.74 mmol) and triethylamine (250 mg, 2.47 mmol) in 15 mL of dichloromethane was treated with 4-methoxybenzenesulfonyl chloride (371 mg, 1.79 mmol) at room temperature for 2.33 h. The solvent was removed in vacua and the residue taken up in ethyl acetate and then washed with 1N KHSO$_4$, saturated aqueous NaHCO$_3$, brine, dried over anhyd MgSO$_4$, filtered and concentrated to give 1.0622 g, of a white foam. The crude product was purified by flash chromatography over silica gel eluting with hexanes and ethyl acetate to give 615 mg, 67%, of pure product with mp 88–92° C., HRFAB MS; calc'd. for C$_{28}$H$_{34}$N$_2$O$_6$S: 533.2298. Found: 533.2329.

Part C

A solution of carbamic acid, product from Part B (519 mg, 0.98 mmol) in 30 mL of methanol was treated with 70 mg of 10% palladium on carbon catalyst and hydrogenated at 46 psig for 22 h at room temperature. The catalyst was removed by filtration through diatomaceous earth and the filtrate concentrated in vacuo to give a clear oil that solidified upon standing, mp 124–127° C., FAB MS; M+Li⁺=399, 387 mg, 100%, that was used directly in the next step.

Part D

A mixture of 2(S)-methyl-3-methylsulfonyl propionic acid (138.5 mg, 0.83 mmol), N-hydroxybenzotriazole (174.6 mg, 1.14 mmol), and 1-(3-dimethylaminopropyl)-3-ethylcarbodiimide hydrochloride (EDC) (171.8 mg, 0.90 mmol) was dissolved in 2.5 mL of dimethylformamide (DMF) and allowed to react for 30 min at 0 ° C. The amine from Part C (304.9 mg, 0.78 mmol) dissolved in 1.5 mL of DMF was added to the above mixture and stirred at room temperature for 14.5 h. The solution was then poured into 20 mL of saturated aqueous NaHCO₃ and extracted with ethyl acetate. The ethyl acetate extracts were washed with 5% aqueous citric acid, saturated aqueous NaHCO₃, brine, dried over anhyd MgSO₄, filtered and concentrated to give a white solid. The material was recrystallized from hexanes and ethyl acetate to give 228 mg, 54% of pure product with mp 115–118 ° C. HRFAB MS; calc'd. for $C_{27}H_{40}N_2O_7S_2$: 541.2042. Found: 541.2064.

EXAMPLE 35

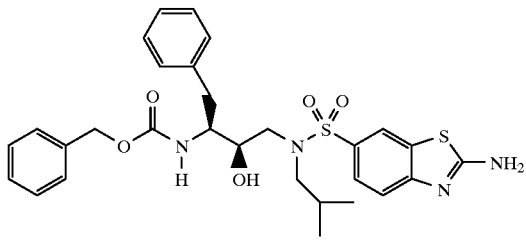

Preparation of Carbamic acid, 2 R-hydroxy-3-[[(2-aminobenzothiazol-6-yl)sulfonyl](2-methylpropyl) amino]-1S-(phenylmethyl)propyl-, phenylmethyl ester Carbamic acid, 2R-hydroxy-3-[[(4-aminophenyl) sulfonyl](2-methylpropyl)amino]-1S-(phenylmethyl) propyl-, phenylmethyl ester 0.30 g (0.571 mmol) was added to a well mixed powder of anhydrous copper sulfate (1.20 g) and potassium thiocyanate (1.50 g) followed by dry methanol (6 mL) and the resulting black-brown suspension was heated at reflux for 2 hrs. The reaction mixture was filtered and the filtrate was diluted with water (5 mL) and heated at reflux. Ethanol was added to the reaction mixture, cooled and filtered. The filtrate upon concentration afforded a residue which was chromatographed (ethyl acetate:hexane 80:20) to afford 0.26 g (78%) of the desired compound as a solid.

EXAMPLE 36

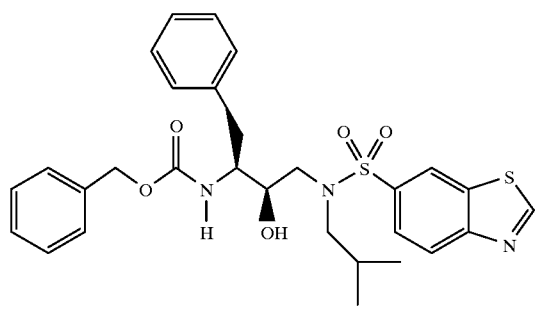

Preparation of Carbamic acid, 2R-hydroxy-3-[[(benzothiazol-6-yl)sulfonyl](2-methylpropyl) amino]-1S-(phenylmethyl)propyl-, phenylmethyl ester Method 1

Carbamic acid, 2R-hydroxy-3-[[(2-aminobenzothiazol-6-yl)sulfonyl](2-methylpropyl)amino)-1S-(phenylmethyl) propyl-, phenylmethyl ester (0.25 g, 0.429 mmol) was added to a solution of isoamylnitrite (0.116 mL, 0.858 mmol) in dioxane (5 mL) and the mixture was heated at 85° C. After the cessation of evolution of nitrogen, the reaction mixture was concentrated and the residue was purified by chromatography (hexane:ethyl acetate 5:3) to afford 0.130 g (53%) of the desired product as a solid.

Method 2

Crude benzothiazole-6-sulfonyl chloride in ethyl acetate-(100 mL) was added to N-[3S-benzyloxycarbonyl amino-2R-hydroxy-4-phenyl]-N-isobutylamine (1.03 g, 2.78 mmol) followed by N-methylmorpholine (4 mL). After stirring at room temperature for 18 hr., the reaction mixture was diluted with ethyl acetate (100 mL), washed with citric acid (5%, 100 mL), sodium bicarbonate (saturated, 100 mL) and brine (100 mL), dried (MgSO₄) and concentrated in vacuo. The residue was chromatographed (silica gel, ethyl acetate: hexane 1:1) to afford 0.340 g (23%) of desired product.

EXAMPLE 37

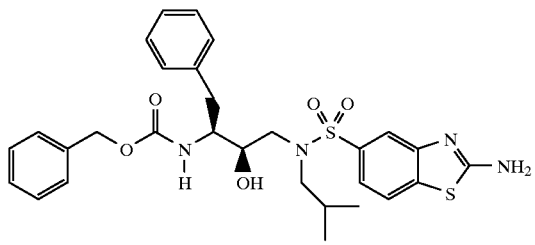

and

-continued

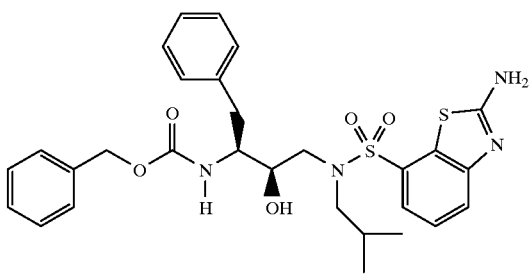

Preparation of Carbamic acid, 2R-hydroxy-3-[(2-aminobenzothiazol-5-yl)sulfonyl](2-methylpropyl)amino]-1S-(phenylmethyl)propyl-, phenylmethyl ester; and Carbamic acid, 2R-hydroxy-3-[[(2-aminobenzothiazol-7-yl)sulfonyl](2-methylpropyl)amino]-1S-(phenylmethyl)propyl-, phenylmethyl ester The carbamic acid, 2R-hydroxy-3-[(3-aminophenylsulfonyl) (2-methylpropyl)amino]-1S-(phenylmethyl)propyl-, phenylmethyl ester 0.36 g (0.685 mmol) was added to a well mixed powder of anhydrous copper sulfate (1.44 g) and potassium thiocyanate (1.80 g) followed by dry methanol (10 mL) and the resulting black-brown suspension was heated at reflux for 2 hrs. The reaction mixture was filtered and the filtrate was diluted with water (5 mL) and heated at reflux. Ethanol was added to the reaction mixture, cooled and filtered. The filtrate upon concentration afforded a residue which was chromatographed (ethyl acetate:hexane 1:1) to afford 0.18 g (45%) of the 7-isomer as a solid. Further elution of the column with (ethyl acetate:hexane 3:2) afforded 0.80 g (20%) afforded the 5-isomer as a solid.

EXAMPLE 38

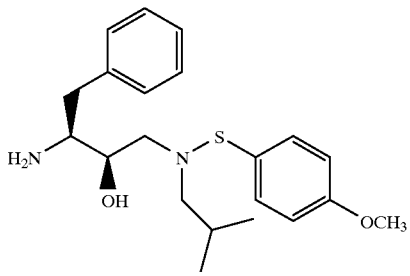

Preparation of 3S-amino-1-[N-(2-methylpropyl)-N-(4-methoxyphenylsulfonyl)amino]-4-phenyl-2R-butanol Part A N-benzyloxycarbonyl-3(S)-amino-1-chloro-4-phenyl-2(S)-butanol To a solution of N-benzyloxycarbonyl-L-phenylalanine chloromethyl ketone (75 g, 0.2 mol) in a mixture of 800 mL of methanol and 800 mL of tetrahydrofuran was added sodium borohydride (13.17 g, 0.348 mol, 1.54 equiv.) over 100 min. The solution was stirred at room temperature for 2 hours and then concentrated in vacuo. The residue was dissolved in 1000 mL of ethyl acetate and washed with 1N $KHSO_4$, saturated aqueous $NaHCO_3$, saturated aqueous NaCl, dried over anhydrous $MgSO_4$, filtered and concentrated in vacuo to give an oil. The crude product was dissolved in 1000 mL of hexanes at 60° C. and allowed to cool to room temperature where upon crystals formed that were isolated by filtration and washed with copious amounts of hexanes. This solid was then recrystallized from hot ethyl acetate and hexanes to provide 32.3 g 43% of N-benzyloxycarbonyl-3(S)-amino-1-chloro-4-phenyl-2(S)-butanol, mp 150–151° C., FAB MS: $MLi^+$=340.

Part B

3(S)-[N-(benzyloxycarbonyl)amino]-1,2(S)-epoxy-4-phenylbutane

A solution of potassium hydroxide (6.52 g. 0.116 mol, 1.2 equiv.) in 970 mL of absolute ethanol was treated with N-benzyloxycarbonyl-3(S)-amino-1-chloro-4-phenyl-2(S)-butanol (32.3 g, 0.097 mol). This solution was stirred at room temperature for 15 minutes and then concentrated in vacuo to give a white solid. The solid was dissolved in dichloromethane and washed with water, dried over anhyd $MgSO_4$, filetered and concentrated in vacuo to give a white solid. The solid was crystallized from hexanes and ethyl acetate to give 22.3 g, 77% of 3(S)-[N-(benzyloxycarbonyl)amino] -1,2(S) -epoxy-4-phenylbutane, mp 102–103° C., FAB MS: $MH^+$=298.

Part C

N-[3(S)-benzyloxycarbonylamino-2(R)-hydroxy-4-phenyl]N-isobutylamine

A solution of N-benzylcarbonyl-3(S)-amino-1,2-(S)-epoxy-4-phenyl butane (50.0 g, 0.168 mol) and isobutylamine (246 g, 3.24 mol, 20 equivalents) in 650 mL of isopropyl alcohol was heated to reflux for 1.25 hours. The solution was cooled to room temperature, concentrated in vacuo and then poured into 1 L of stirring hexane whereupon the product crystallized from solution. The product was isolated by filtration and air dried to give 57.56 g, 92% of N[3(S)-benzyloxycarbonylamino-2(R)-hydroxy-4-phenyl]-N-isobutylamine, mp 108.0–109.5° C., MH+m/z=371.

Part D phenylmethyl [2(R)-hydroxy-3-[N-(2-methylpropyl)-N-(4-methoxyphenylsulfonyl)amino]-1S-(phenylmethyl)propyl]carbamate The amine from Part C (936.5 mg, 2.53 mmol) and triethylamine (2.88.5 mg, 2.85 mmol) was dissolved in 20 mL of dichloromethane and treated with 4-methoxybenzenesulfonyl chloride (461 mg, 2.61 mmol). The solution was stirred at room temperature for 16 hours and then concentrated in vacuo. The residue was dissolved in ethyl acetate and this solution was washed with iN $KHSC_4$, saturated aqueous $NaHCO_3$, brine, dried over anhyd $MgSO_4$, filtered, and concentrated to give a clear oil 1.234 g. The oil was crystallized from a mixture of ether and hexanes, 729.3 mg, 56.5% mp 95–99° C., FAB MS: $MH^+$= 511.

Part E 3S-amino-1-[N-(2-methylpropyl)-N-(4-methoxyphenylsulfonyl)amino]-4-phenyl-2R-butanol A solution of phenylmethyl [2(R)-hydroxy-3-[N-(2-methylpropyl)-N-(4-methoxyphenylsulfonyl)amino]1-S-(phenylmethyl)propyl carbamate (671.1 mg, 1.31 mmol) from Part D in 10 mL of methanol was hydrogenated over 50 mg of 10% palladium on carbon at 40 psig at room temperature for 15 hours. The catalyst was removed by filtration through diatomaceous earth and the filtrate concentrated to give a white foam, 474.5 mg, 96%, FAB MS: $MH^+$=377.

EXAMPLE 39

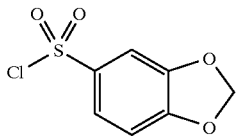

Preparation of 1.3-benzodioxole-5-sulfonyl chloride

Method 1

To a solution of 4.25 g of anhydrous N,N-dimethylformamide at 0° C. under nitrogen was added 7.84 g of sulfuryl chloride, whereupon a solid formed. After stirring for 15 minutes, 6.45 g of 1,3-benzodioxole was added, and the mixture heated at 100° C. for 2 hours. The reaction was cooled, poured into ice water, extracted with methylene chloride, dried over magnesium sulfate, filtered and concentrated to give 7.32 g of crude material as a black oil. This was chromatographed on silica gel using 20% methylene chloride/hexane to afford 1.9 g of (1,3-benzodioxol-5-yl)sulfonyl chloride.

Method 2

To a 22 liter round bottom flask fitted with a mechanical stirrer, a cooling condenser, a heating mantle and a pressure equalizing dropping funnel was added sulfur trioxide DMF complex (2778 g, 18.1 moles). Dichloroethane (4 liters) was then added and stirring initiated. 1,3-Benzodioxole (1905 g, 15.6 moles) as then added through the dropping funnel over a five minute period. The temperature was then raised to 75° C. and held for 22 hours (NMR indicated that the reaction was done after 9 hours.) The reaction was cooled to 26° and oxalyl chloride (2290 g, 18.1 moles) was added at a rate so as to maintain the temperature below 40° C. (1.5 hours). The mixture was heated to 67° C. for 5 hours followed by cooling to 16° C. with an ice bath. The reaction was quenched with water (5 l) at a rate which kept the temperature below 20° C. After the addition of water was complete, the mixture was stirred for 10 minutes. The layers were separated and the organic layer was washed again twice with water (5 l). The organic layer was dried with magnesium sulfate (500 g) and filtered to remove the drying agent. The solvent was removed under vacuum at 50° C. The resulting warm liquid was allowed to cool at which time a solid began to form. After one hour, the solid was washed with hexane (400 mL), filtered and dried to provide the desired sulfonyl chloride (2823 g). The hexane wash was concentrated and the resulting solid washed with 400 mL hexane to provide additional sulfonyl chloride (464 g). The total yield was 3287 g (95.5% based upon 1,3-benzodioxole).

Method 3

1,4-benzodioxan-6-sulfonyl chloride was prepared according to the procedure disclosed in EP 583960, incorporated herein by reference.

EXAMPLE 40

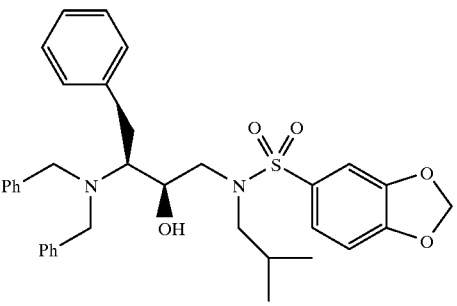

Preparation of 1-[N-[(1,3-benzodioxol-5-yl)sulfonyl]-N-(2-methylpropyl)amino]-3(S)-[bis(phenylmethyl)amino]-4-phenyl-2(R) -butanol Method 1

To a 5000 mL, 3-necked flask fitted with a mechanical stirrer was added N-[3(S)-[N,N-bis(phenylmethyl)amino]-2(R)-hydroxy-4-phenylbutyl]-N-isobutylamine-oxalic acid salt (354.7 g, 0.7 mole) and 1,4-dioxane (2000 mL). A solution of potassium carbonate (241.9 g, 1.75 moles) in water (250 mL) was then added.

The resultant heterogeneous mixture was stirred for 2 hours at room temperature followed by the addition of 1,3-benzodioxole-5-sulfonyl chloride (162.2 g, 0.735 mole) dissolved in 1,4-dioxane (250 oL) over 15 minutes. The reaction mixture was stirred at room temperature for 18 hours. Ethyl acetate (1000 mL) and water (500 mL) were charged to the reactor and stirring continued for another 1 hour. The aqueous layer was separated and further extracted with ethyl acetate (200 mL). The combined ethyl acetate layers were washed with 25% brine solution (500 mL) and dried over anhydrous magnesium sulfate. After filtering and washing the magnesium sulfate with ethyl acetate (200 mL), the solvent in the filtrate was removed under reduced pressure yielding the desired sulfonamide as an viscous yellow foamy oil (440.2 g 105% yield). HPLC/MS (electrospray) (m/z 601 [M+H$^+$].

EXAMPLE 41

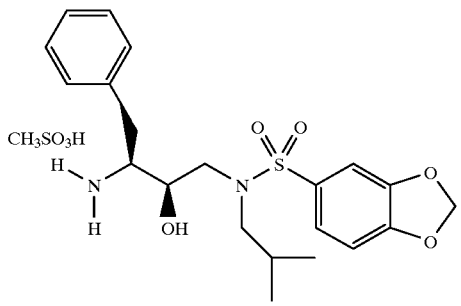

Preparation of 1-[N-[(1,3-benzodioxol-5-yl) sulfonyl]-N-(2-methylpropyl)amino]-3(S)-amino-4-phenyl-2(R)-butanol-methanesulfonic acid salt Method 1

Crude 1-[N-[(1,3-benzodioxol-5-yl)sulfonyl]-N-(2-methylpropyl)amino]-3(S)-[bis(phenylmethyl)amino]-4-phenyl-2(R)-butanol (6.2 g, 0.010 moles) was dissolved in methanol (40 mL). Methanesulfonic acid (0.969 g, 0.010 moles) and water (5 mL) were then added to the solution.

The mixture was placed in a 500 mL Parr hydrogenation bottle containing 20% Pd(OH)$_2$ on carbon (255 mg, 50% water content). The bottle was placed in the hydrogenator and purged 5 times with nitrogen and 5 times with hydrogen. The reaction was allowed to proceed at 35° C. with 63 PSI hydrogen pressure for 18 hours. Additional catalyst (125 mg) was added and, after purging, the hydrogenation continued for and additional 20 hours. The mixture was filtered through celite which was washed with methanol (2×10 mL). Approximately one third of the methanol was removed under reduced pressure. The remaining methanol was removed by aziotropic distillation with toluene at 80 torr. Toluene was added in 15, 10, 10 and 10 mL portions. The product crystallized from the mixture and was filtered and washed twice with 10 mL portions of toluene. The solid was dried at room temperature at 1 torr for 6 hours to yield the amine salt (4.5 g, 84%). HPLC/MS (electrospray) was consistent with the desired product (m/z 421 [M+H]$^+$).

Method 2

Part A

N-[3(S)-[N,N-bis(phenylmethyl)amino]-2(R)-hydroxy-4-phenylbutyl]-N-isobutylamine.oxalic acid salt (2800 g, 5.53 moles) and THF (4 L) were added to a 22 L round bottom flask fitted with a mechanical stirrer. Potassium carbonate (1921 g, 13.9 moles) was dissolved in water (2.8 L) and added to the THF slurry. The mixture was then stirred for one hour. 1,3-benzodioxole-5-sulfonyl chloride (1281 g, 5.8 moles) was dissolved in THF (1.4 L) and added to the reaction mixture over 25 minutes. An additional 200 mL of THF was used to rinse the addition funnel. The reaction was allowed to stir for 14 hours and then water (4 L) was added. This mixture was stirred for 30 minutes and the layers allowed to separate. The layers was removed and the aqueous layer washed twice with THF (500 mL). The combined THF layers were dried with magnesium sulfate (500 g) for one hour. This solution was then filtered to remove the drying agent and used in subsequent reactions.

Part B

To the THF solution of crude 1-[N-((1,3-benzodioxol-5-yl)sulfonyl]-N-(2-methylpropyl)amino]-3(S)-[bis(phenylmethyl)amino]-4-phenyl-2(R)-butanol was added water (500 mL) followed by methane sulfonic acid (531 g, 5.5 moles). The solution was stirred to insure complete mixing and added to a 5 gallon autoclave. Pearlman's catalyst (200 g of 20% Pd(OH)$_2$ on C/ 50% water) was added to the autoclave with the aid of THF (500 mL). The reactor was purged four times with nitrogen and four times with hydrogen. The reactor was charged with 60 psig of hydrogen and stirring at 450 rpm started. After 16 hours, HPLC analysis indicated that a small amount of the monobenzyl intermediate was still present. Additional catalyst (50 g) was added and the reaction was allowed to run overnight. The solution was then filtered through celite (500 g) to remove the catalyst and concentrated under vacuum in five portions. To each portion, toluene (500 mL) was added and removed under vacuum to azeotropically removed residual water. The resulting solid was divided into three portions and each washed with methyl t-butyl ether (2 L) and filtered. The residual solvent was removed at room temperature in a vacuum oven at less than 1 torr to yield the 2714 g of the expected salt.

If desired, the product can be further purified by the following procedure. A total of 500 mL of methanol and 170 g of material from above was heated to reflux until it all dissolved. The solution was cooled, 200 mL of isopropanol added and then 1000–1300 mL of hexane, whereupon a white solid precipitated. After cooling to 0° C., this precipitate was collected and washed with hexane to afford 123 g of the desired material. Through this procedure, the original material which was a 95:5 mixture of alcohol diastereomers was greater than 99:1 of the desired diastereomer.

EXAMPLE 42

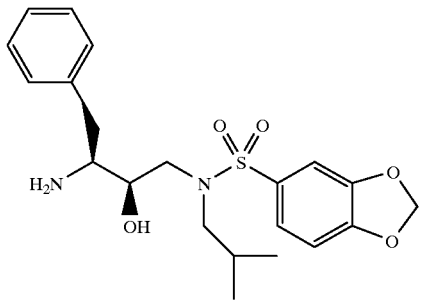

Preparation of 2R-hydroxy-3-[[(1,3-benzodioxol-5-yl)sulfonyl](2-methylpropyl)amino]-1S-(phenylmethyl)propylamine Part A Preparation of 2R-hydroxy-3-[[(1,3-benzodioxol-5-yl)sulfonyl](2-methylpropyl)amino]-1S-(phenylmethyl)propylcarbamic acid phenylmethyl ester To a solution of 3.19 g(8.6 mmol) of N-[3S-benzyloxycarbonylamino-2R-hydroxy-4-phenyl]-N-isobutylamine in 40 mL of anhydrous methylene chloride, was added 0.87 g of triethylamine. The solution was cooled to 0° C. and 1.90 g of (1,3-benzodioxol-5-yl)sulfonyl chloride was added, stirred for 15 minutes at 0° C., then for 17 hours at room temperature. Ethyl acetate was added, washed with 5% citric acid, saturated sodium bicarbonate, brine, dried and concentrated to yield crude material. This was recrystallized from diethyl ether/hexane to afford 4.77 g of pure 2R-hydroxy-3-([(1,3-benzodioxol-5-yl)sulfonyl](2-methylpropyl)amino]-1S-(phenylmethyl)propylcarbamic acid phenylmethyl ester.

Part B

Preparation of 2R-hydroxy-3-[[(1,3-benzodioxol-5-yl)sulfonyl](2-methylpropyl)amino]-1S-(phenylmethyl)propylamine A solution of 4.11 g of carbamic acid, 2R-hydroxy-3-[[(1,3-benzodioxol-5-yl)sulfonyl](2-methylpropyl)amino]-1S-(phenylmethyl)propyl-, phenylmethyl ester in 45 mL of tetrahydrofuran and 25 mL of methanol was hydrogenated over 1.1 g of 10% palladium-on-carbon under 50 psig of hydrogen for 16 hours. The catalyst was removed by filtration and the filtrate concentrated to afford 1.82 g of the desired 2R-hydroxy-3-[[(1,3-benzodioxol-5-yl)sulfonyl](2-methylpropyl)amino]-1S-(phenylmethyl)propylamine.

EXAMPLE 43

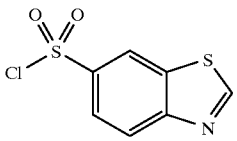

Preparation of Benzothiazole-6-sulfonyl Chloride

Part A

Preparation of N-(4-Sulfonamidophenyl)thiourea

A mixture of sulfanilamide (86 g, 0.5 mole), ammonium thiocyanate (76.0 g, 0.5 mole) and dilute hydrochloric acid (1.5 N, 1 L) was mechanically stirred and heated at reflux for 2 hr. About 200 mL of water was distilled off and concentration of the reaction mixture afforded a solid. The solid was filtered and was washed with cold water and air dried to afford 67.5 g (59%) of the desired product as a white powder.

Part B

Preparation of 2-Amino-6-sulfonamidobenzothiazole

Bromine (43.20 g, 0.27 mol) in chloroform (200 mL) was added over 1 hr. to a suspension of N-(4-sulfonamidophenyl)-thiourea (27.72, 0.120 mol) in chloroform (800 mL). After the addition, the reaction mixture was heated at reflux for 4.5 hr. The chloroform was removed in vacuo and the residue was repeatedly distilled with additional amounts of chloroform. The solid obtained was treated with water (600 mL) followed by ammonium hydroxide (to make it basic), then was heated at reflux for 1 hr. The cooled reaction mixture was filtered, washed with water and air dried to afford 22.0 g (80%) of the desired product as a white powder.

Part C

Preparation of Benzothiazole-6-sulfonic acid

A suspension of 2-amino-6-sulfonamido-benzothiazole (10.0 g, 43.67 mmol) in dioxane (300 mL) was heated at reflux. Isoamylnitrite (24 mL) was added in two portions to the reaction mixture. vigorous evolution of gas was observed (the reaction was conducted behind a shield as a precaution) and after 2 hr., a red precipitate was deposited in the reaction vessel. The reaction mixture was filtered hot, and the solid was washed with dioxane and was dried. The solid was recrystallized from methanol-water. A small amount of a precipitate was formed after 2 days. The precipitate was filtered off and the mother liquor was concentrated in vacuo to afford a pale red-orange solid (8.0 g, 85%) of pure product.

Part D

Preparation of 6-Chlorosulfonylbenzothiazole

Thionyl chloride (4 mL) was added to a suspension of the benzothiazole-6-sulfonic acid (0.60 g, 2.79 mmol) in dichloroethane (15 mL) and the reaction mixture was heated at reflux and dimethylformamide (5 mL) was added to the reaction mixture to yield a clear solution. After 1.5 hr. at reflux, the solvent was removed in vacuo and excess HCl and thionyl chloride was chased by evaporation with dichloroethane.

EXAMPLE 44

Preparation of 2R-hydroxy-3-[[(1,4-benzodioxan-6-yl)sulfonyl](2-methypropyl)amino]-1S-(phenylmethyl)propylcarbamic acid phenylmethyl ester

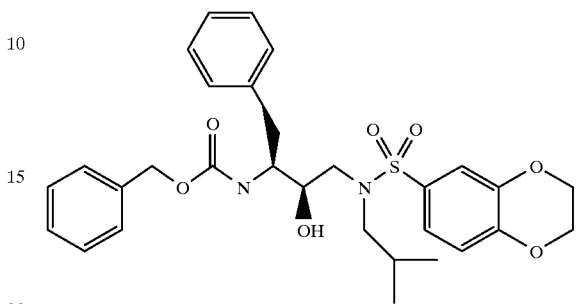

To a solution of the N-[3S-[(phenylmethoxycarbonyl)amino]3-2R-hydroxy-4-phenylbutyl]-N-(2-methylpropyl)amine (0.5 g, 1.35 mmol) in $CH_2Cl_2$ (5.0 mL) containing Et3N (0.35 mL, 2.5 mmol) was added 1,4-benzodioxan-6-sulfonyl chloride (0.34 g, 1.45 mmol) and stirred at 0° C. for 30 min. After stirring at room temperature for 1 hour, the reaction mixture was diluted with $CH_2Cl_2$ (20 mL), washed with cold 1N HCl (3×20 mL), water (2×20 mL), satd. $NaHCO_3$ (2×20 mL) and water (3×20 mL), dried ($Na_2SO_4$) and concentrated under reduced pressure. The resulting residue was purified by flash chromatography using 35% EtOAc in hexane to give the desired product as a white amorphous solid which crystallized from MeOH as a white powder (0.65 g. 84% yield): m. p. 82–84° C., HRMS-FAB: calcd for $C_{30}H_{37}N_2O_7S$ 569.2321 ($MH^+$), found 569.2323.

EXAMPLE 45

Preparation of [2R-hydroxy-3-[(benzothiazole-6-sulfonyl)-(2-methylpropyl)amino]-1S-(phenylmethyl)propyl]amine hydrochloride

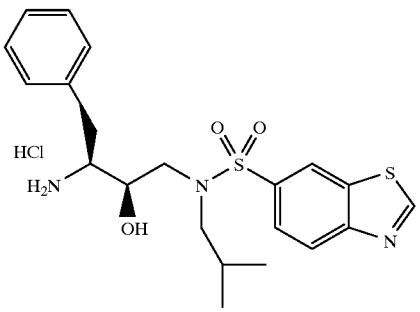

Part A

Preparation of [2R-hydroxy-3-[(4-aminophenylsulfonyl)(2-methylpropyl)amino]-1S-(phenylmethyl)propylcarbamic acid t-butyl ester

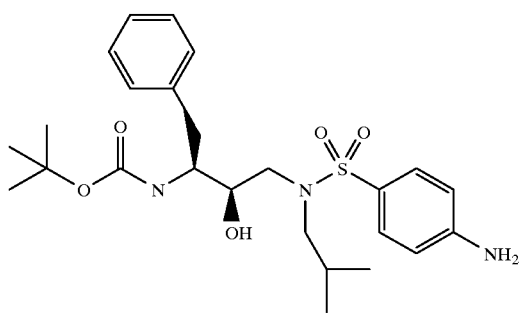

A mixture of [2R-hydroxy-3-[(4-aminophenylsulfonyl)(2-methylpropyl)-amino]-1S-(phenylmethyl)propylamine 3.7 g (9.45 mmol) and BOC-ON (2.33 g, 9.45 mmol) and triethylamine (0.954 g, 9.45 mmol) in tetrahydrofuran (60 mL) was stirred for 16 hours and concentrated in vacuo. The residue was dissolved in dichloromethane (200 mL), washed with sodium hydroxide (1N, 100 mL) and citric acid (5%, 100 mL), dried (MgSO₄), and concentrated to afford 1.18 g (94%) of the desired product as a white solid.

Part B

Preparation of [2R-Hydroxy-3-[[(2-aminobenzothiazol-6-yl)sulfonyl](2-methylpropyl)amino]-1S-(phenylmethyl) propylcarbamic acid t-butyl ester

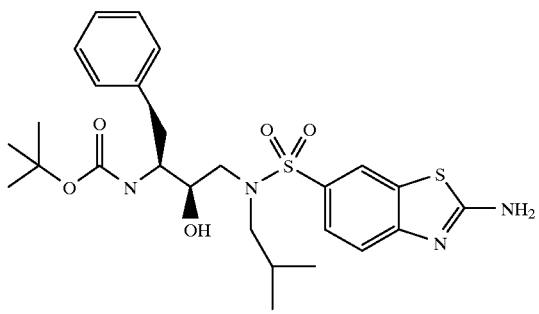

The [2R-hydroxy-3-[(4-aminophenylsulfonyl)(2-methylpropyl)amino]-1S-(phenylmethyl)propylcarbamic acid t-butyl ester (1.12 g, 2.279 mmol) was added to a well mixed powder of anhydrous copper sulfate (4.48 g) and potassium thiocyanate (5.60 g) followed by dry methanol (35 mL) and the resulting black-brown suspension was heated at reflux for 2 hours. The reaction mixture turned grey. The reaction mixture was filtered and the filtrate was diluted with water (50 mL) and heated at reflux. Ethanol was added to the reaction mixture, cooled and filtered. The filtrate upon concentration afforded a residue which was chromatographed (ethyl acetate:methanol 90:10) to afford 0.80 g (78%) of -he deprotected compound as a solid. This was directly reprotected via the following procedure; (2.25 g, 5.005 mmol) BOC-ON (1.24 g), and triethylamine (0.505 g, 5.005 mmol) in tetrahydrofuran (20 mL) was stirred at room temperature for 18 hours. The reaction mixture was concentrated and the residue was dissolved in dichloromethane (200 mL) and was washed with sodium hydroxide (1N, 100 mL) and citric acid (5%, 100 mL) dried (MgSO4) and concentrated to afford a residue which was chromatographed (ethyl acetate:hexane 3:1) to afford 1.8 g (65%) of the desired product as a solid.

Part C

Preparation of [2R-hydroxy-3-[[(benzothiazol-6-yl)sulfonyl](2-methylpropyl)amino]-1S-(phenylmethyl) propylcarbamic acid t-butyl ester

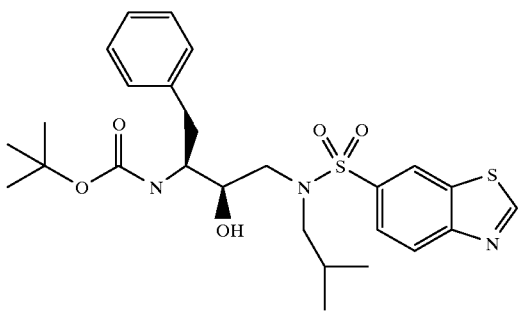

[2R-Hydroxy-3-[[(2-aminobenzothiazol-6-yl)sulfonyl] (2-methylpropyl)amino]-1S-(phenylmethyl)propylcarbamic acid t-butyl ester (1.80 g, 3.2755 mmol) was added to a solution of isoamylnitrite (0.88 mL) in dioxane (20 mL) and the mixture was heated at 85° C. After the cessation of evolution of nitrogen, the reaction mixture was concentrated and the residue was purified by chromatography (hexane:ethyl acetate 1:1) to afford 1.25 g (78%) of the desired product as a solid.

Part D

Preparation of [2R-hydroxy-3-[[(benzothiazol-6-yl) sulfonyl](2-methylpropyl)amino]-1S-(phenylmethyl) propylamine.hydrochloride.

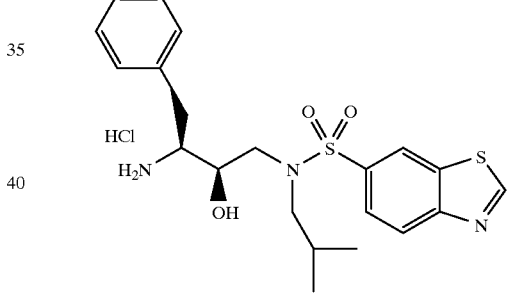

[2R-hydroxy-3-[[(benzothiazol-6-yl)sulfonyl](2-methylpropyl)amino]-1S-(phenylmethyl)propylcarbamic acid t-butyl ester (1.25 g, 2.3385 mmol) was added dioxane/HCl (4N, 10 mL) and was stirred at room temperature for 2 hours and concentrated. Excess HCl was chased with toluene to afford 1.0 g (quantitative yield) of the desired product.

EXAMPLE 46

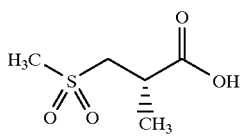

Preparation of 2(S)-methyl-3-(methylsulfonyl) propionic Acid

Part A

To a solution of 200 g (1.23 mol) of D-(−)-3-acetyl-b-mercaptoisobutyric acid in 1.0 L of methanol, was added 161.0 g (2.47 mol) of potassium hydroxide dissolved in 500 mL of methanol while maintaining the temperature below 10 C. while cooling with an ice bath. After stirring an additional 20 minutes, 117 mL (156 g, 1.23 mol) of dimethyl sulfate was added while maintaining the temperature below 20 C. The ice bath was removed and the mixture stirred for an additional 60 minutes. The salts were removed by filtration, the solvents removed under reduced pressure and ethyl acetate added. After separating the aqueous layer, it was acidified with concentrated hydrochloric acid, extracted with ethyl acetate, dried over anhydrous magnesium sulfate, filtered and concentrated to afford 164 g (99%) of the desired 2S-methyl-3-(methylthio)propionic acid, m/e =133 (M–H).

Part B

To a solution of 10.0 g (74.6 mmol) of 2S-methyl-3-(methylthio)propionic acid in 150 mL of acetone and 30 mL of water, cooled to 18 C in an ice bath, was added 161.8 g (263 mmol) of oxone. After approximately half of material had been added, the temperature rose to 24 C, the addition was stopped, temperature lowered to 18 C., then addition continued. After stirring at 15–20 C. for 15 minutes, the bath was removed and the reaction stirred at room temperature for 1 hour. The solids were filtered and washed with acetone, the filtrate concentrated to approximately 40 mL and the residue dissolved in 200 mL of ethyl acetate. The ethyl acetate layer was dried with anhydrous magnesium sulfate, filtered and concentrated to afford 11.4 g of an oil. This was dissolved in a minimum of ethyl acetate and hexane added to cause a precipitate to form. This was collected to afford 6.95 g of the desired product, m/e=167 (M+H).

EXAMPLE 47

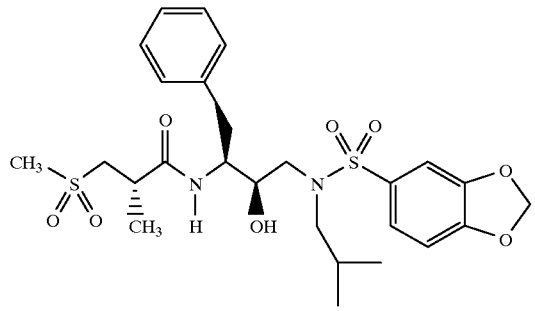

Preparation of N-[2R-hydroxy-3-[(2-methylpropyl) [(1,3-benzodioxol-5-yl)sulfonyl]amino]-1S-(phenylmethyl)propyl]-2S-methyl-3-(methylsulfonyl)propanamide To a solution of 5.0 g (30 mmol) of 2S-methyl-3-(methylsulfonyl)propionic acid and 6.90 g (45 mmol) N-hydroxybenzotriazole in 30 mL of anhydrous DMF at 0° C. under nitrogen, was added 6.34 g (33 mmol) of EDC. After approximately 10 minutes, the EDC was all dissolved. After 60 minutes at 0° C., a solution of 15.5 g (30 mmol) of 2R-hydroxy-3-[[(1,3-benzodioxol-5-yl)sulfonyl](2-methylpropyl)amino]-1S-(phenylmethyl)propylamine methanesulfonate in 30 mL of anhydrous DMF, previously neutralized with 3.4 mL (31.6 mmol) of 4-methylmorpholine, was added. After 3 hrs at 0° C., the mixture was then stirred overnight for 17 hrs. The DMF was removed under reduced pressure, ethyl acetate added, washed with 5% citric acid, saturated sodium bicarbonate, water, brine, dried over anhydrous magnesium sulfate, filtered and concentrated to afford 16 g of crude material, which was 88% pure by HPLC. The product was chromatographed on silica gel using 20%–80% ethyl acetate/hexane to afford the pure product, which was recrystallized from ethyl acetate/hexane to afford 8.84 g of pure product, mp 131.8–133.8° C.

Alternatively, to a solution of 35.0 g (211 mmol) of 2S-methyl-3-(methylsulfonyl)propionic acid and 48.3 g (315 mmol) N-hydroxybenzotriazole in 210 mL of anhydrous DMF at 0° C. under nitrogen, was added 44.4 g (231 mmol) of EDC. After approximately 30 minutes, the EDC was all dissolved. After an additional 60 minutes at 0° C., a solution of 108.8 g (211 mmol) of 2R-hydroxy-3-[[(1,3-benzodioxol-5-yl)sulfonyl](2-methylpropyl)amino]-1S-(phenylmethyl)propylamine methanesulfonate in 350 mL of anhydrous DMF previouly neutralized with 24 mL (22.3 g) of 4-methylmorpholine, was added. After 2 hrs at 0° C., the mixture was then stirred overnight for 18 hrs. The DMF was removed under reduced pressure, 1 L of ethyl acetate added, washed with 5% citric acid, saturated sodium bicarbonate, water, brine, dried over anhydrous magnesium sulfate, filtered and concentrated to afford 120.4 g of crude material, which was 90% purity by HPLC. The product was crystallized twice from 750–1000 mL of absolute ethanol to afford 82.6 g of the desired product, >99% purity by HPLC material.

EXAMPLE 48

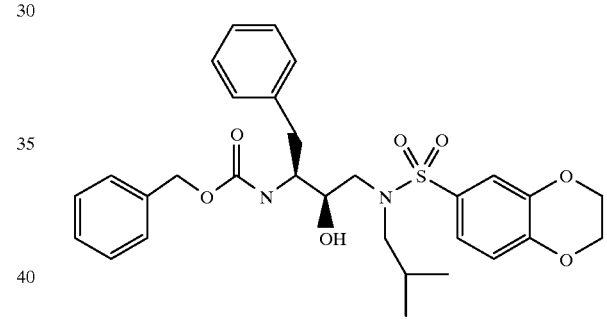

Preparation of 1-[(2-methylpropyl)[(1,4-benzodioxane-6-yl)sulfonyl]amino]-3S-[(phenylmethoxycarbonyl)amino]-4-phenylbutan-2R-ol To a solution of the N-[3S-[(phenylmethoxycarbonyl) amino]-2R-hydroxy-4-phenylbutyl]-N-(2-methylpropyl) amine (0.5 g, 1.35 mmol) in $CH_2Cl_2$ (5.0 mL) containing Et3N (0.35 mL, 2.5 mmol) was added 1,4-benzodioxan-6-sulfonyl chloride (0.34 g, 1.45 mmol) (prepared according to the literature procedure in EP 583960 A2, 1994) and stirred at 0° C. for 30 min. After stirring at room temperature for 1 h, the reaction mixture was diluted with $CH_2Cl_2$ (20 mL), washed with cold 1N HCl (3×20 mL), water (2×20 mL), satd. $NaHCO_3$ (2×20 mL), water (3×20 mL), dried ($Na_2SO_4$) and concentrated under reduced pressure. The resulting residue was purified by flash chromatography using 35% EtOAc in hexane to give the desired 1,4-benzodixan-sulfonamide as a white amorphous solid which crystallized from MeOH as a white powder (0.65 g. 84%): m.p. 82–84° C., HRMS-FAB : calcd for $C_{30}H_{37}N_2O_7S$ 569.2321 (MH$^+$), found 569.2323.

EXAMPLE 49

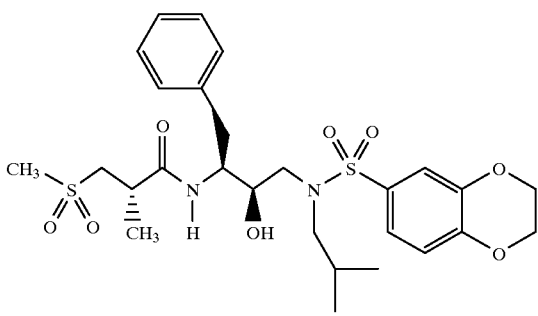

Preparation of N-[2R-hydroxy-3-[(2-methylpropyl)[(1,4-benzodioxane-6-yl)sulfonyl]amino]-1S-(phenylmethyl)propyl]-2S-methyl-3-(methylsulfonyl)propanamide Part A A solution of 1-[(2-methylpropyl)[(1,4-benzodioxane-6-yl)sulfonyl]amino]-3S-[(phenylmethoxycarbonyl)amino]-4-phenylbutan-2R-ol (0.6 g, 1.06 mmol) in THF (10 mL) was hydrogenated at 50 psi in the presence of 10% Pd/C (0.4 g, ) for 12 h, at room temperature. The catalyst was removed by filtration, filtrate was concentrated under reduced pressure.

Part B

The resulting residue from Part A was dissolved in $CH_2Cl_2$ (4.0 mL) and added to a cooled (0° C.) mixture of 2S-methyl-3-(methylsulfonyl)propionic acid (0.2 g, 1.2 mmol), HOBt (0.25 g, 1.6 mmol) and EDC (0.24 g, 1.25 mmol) in a solvent mixture of DMF (2 mL) and $CH_2Cl_2$ (2 mL) and stirred at 0° C. for 2 h. After stirring for 3 h at room temperature, the reaction mixture was diluted with $CH_2Cl_2$ (15 mL), washed with cold 0.5N NaOH (2×10 mL), water (3×15 mL), dried ($Na_2SO_4$) and concentrated in vacuo. The residue was purified by flash chromatography on silica gel using EtOAc as the eluent to furnish the desired sulfonamide as a white amorphous powder (0.5 g, 82%). $R_t$=19.9 min. FABMS m/z 589 (M+Li)$^+$; HRMS-FAB calcd. for $C_{27}H_{39}N_2O_8S_2$ 583.2148 (MH)+, found 583.2115.

EXAMPLE 50

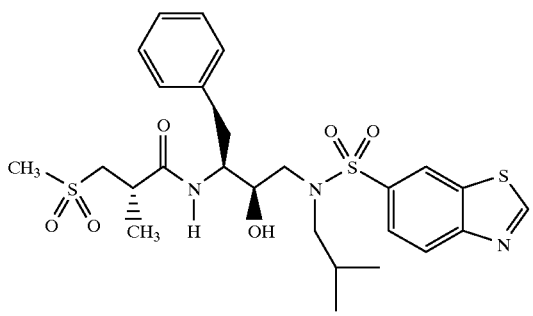

Preparation of N-[2R-hydroxy-3-[(2-methylpropyl)[(benzothiazol-5-yl)sulfonyl]amino]-1S-(phenylmethyl)propyl]-2S-methyl-3-(methylsulfonyl)propanamide A mixture of 2-(S)-methyl-3-methylsulfonylpropionic acid (0.220 g, 1.325 mmol), hydroxybenzotriazole (0.178 g, 1.325 mmol), EDC (0.253 g, 1.325 mmol) in DMF (20 mL0 was stirred for 1 h at room temperature. [2R-hydroxy-3-[(benzothiazole-6-sulfonyl)-(2-methylpropyl)amino]-1S-(phenylmethyl)propylamine hydrochloride (0.620 g, 1.325 mmol) was added followed by triethylamine (0.260 g, 2.66 mmol) and stirred for 18 h. The reaction mixture was concentrated in vacuo and the residue was partitioned between ethyl acetate (200 mL) and citric acid (5%, 100 mL). The organic layer was washed with saturated sodium bicarbonate (100 mL), brine (100 mL) dried (MgSO$_4$) and concentrated. Chromatography with ethyl acetate: hexane 3:1) afforded 0.330 g (43%) of the desired product as a powder. Calculated: M=581; Found: M+Li=588.

EXAMPLE 51

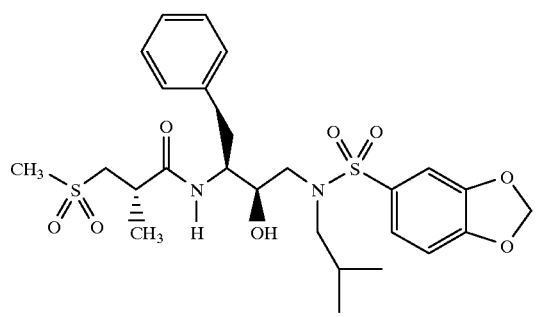

Preparation of N-[2R-hydroxy-3-[(2-methylpropyl)[(1,3-benzodioxol-5-yl)sulfonyl]amino]-1S-(phenylmethyl)propyl]-2S-methyl-3-methylsulfonyl)propanamide Part A Preparation of N-[2R-hydroxy-3-[(2-methypropyl)[(1,3-benzodioxol-5-yl)sulfonyl]amino]-1S-(phenylmethyl)propyl]-2S-methyl-3-(acetylthio)propanamide

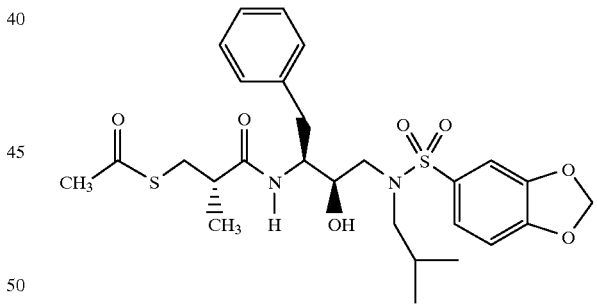

N-Hydroxybenzotriazole (1.79 g, 11.6 mmol) was added to solution D-(−)-S-acetyl-β-mercaptoisobutyric acid (1.26 g, 7.8 mmol) in 15 mL of dry dimethylformamide and cooled in an ice bath. To the cooled solution, was added EDC (1.64 g, 8.5 mmol) and stirred for 30 minutes. To this was added (3.27 g, 7.8 mmol) of 2R-hydroxy-3-[[(1,3-benzodioxol-5-yl)sulfonyl](2-methylpropyl)amino]-1S-(phenylmethyl)propylamine and this was stirred 16 hours with warming to room temperature. The solvent was removed and the residue partitioned between ethyl acetate and 5% aqueous potassium hydrogen sulfate. The organic layer was washed with saturated sodium bicarbonate, and brine, dried over magnesium sulfate filtered and concentrated to yield 4.4 grams of a crude oil, mass spectrum, m/z=571.8 (M+Li).

Part B
  Preparation of N-[2R-hydroxy-3-[(2-methylpropyl)[(1,3-benzodioxol-5-yl)sulfonyl]amino]-1S-(phenylmethyl)propyl]-2S-methyl-3-mercaptopropanamide

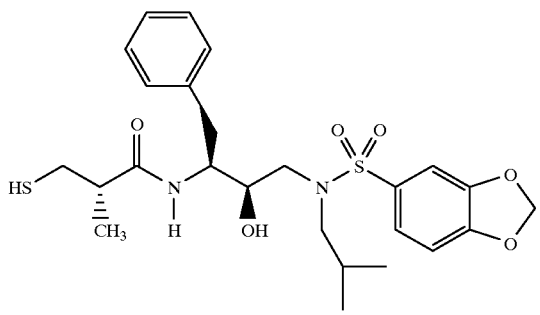

A solution of 4.29 g, (7.8 mmol) of S-acetyl compound from part A dissolved in 100 mL of dry methanol was cooled in an ice bath. Anhydrous ammonia was bubbled into the solution for one minute. The solution was stoppered and stirred to room temperature over 5 hours. The contents were concentrated on a rotory evaporator, and the residue was dissolved in ethyl acetate. The organic solution was washed with water, and brine, dried over magnesium sulfate, filtered and concentrated to yield 3.9 grams of the free mercaptan which was used without purification.

Part C
  Preparation of N-[2R-hydroxy-3-[(2-methylpropyl)[(1,3-benzodioxol-5-yl)sulfonyl]amino]-1S- (phenylmethyl)propyl]-2S-methyl -3 -(methyl thio)propanamide

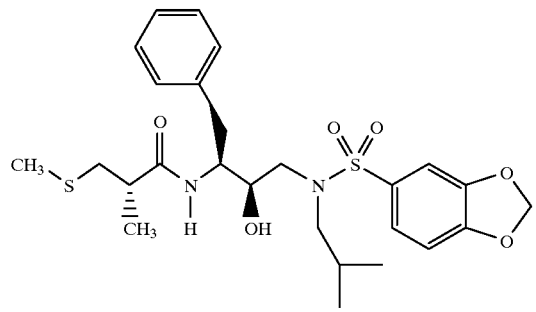

A solution of 1.65 g, ( 3.15 mmol) of the mercaptan from Part B in 25 mL of tetrahydrofuran was cooled in an ice bath. To this cooled solution was added 0.52 g, 3.52 mmol) of DBU followed by 0.22 mL, (3.5 mmol) of methyl iodide and the ice bath was removed after 5 minutes. After several hours at room temperature the contents were concentrated on a rotory evaporator, and the residue was dissolved in ethyl acetate. The organics were washed with potassium hydrogen sulfate, sodium bicarbonate and brine, dried over magnesium sulfate, filtered and concentrated to yield 1.48 g of a crude white foam.

Part D
  Preparation of N-[2R-hydroxy-3-[(2-methylpropyl)[(1,3-benzodioxol-5-yl)sulfonyl]amino]-1S-(phenylmethyl)propyl]-2S-methyl-3-(methylsulfonyl)propanamide To a solution of 440 mg, (0.8 mmol) of thiomethylether from part C above dissolved in 10 mL of methanol, was added 1.52 g, (24.0 mmol) of oxone followed by 10 mL of water. The suspension was stirred at room temperature for four hours. The mixture was concentrated on a rototry evaporator, diluted with 50 mL of water and extracted with ethyl acetate. The organic layer was washed with sodium bicarbonate, dried over magnesium sulfate, filtered and concentrated to yield 390 mg of crude sulfone. Purification by flash chromatography using 1;1 ethyl acetate;hexane as the eluant yielded 330 mg of the desired compound; mass spectrum, m/z=575.4 (M+Li).

EXAMPLE 52

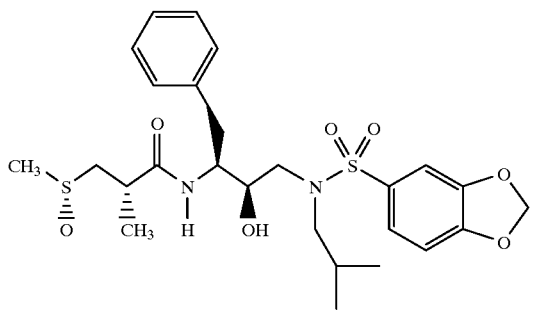

and

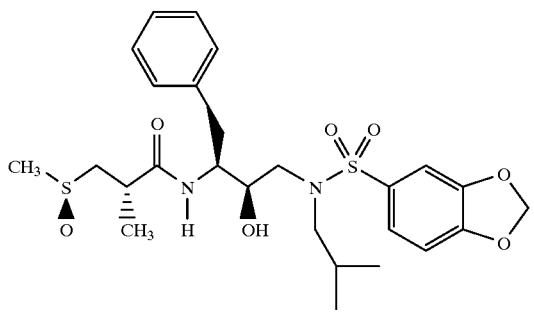

Preparation of N-[2R-hydroxy-3-[(2-methylpropyl)[(1,3-benzodioxol-5-yl)sulfonyl]amino]-1S-(phenylmethyl)propyl]-2S-methyl-3-(methylsulfinyl)propanamide To a solution of N-[2R-hydroxy-3-[(2-methylpropyl)[(1,3-benzodioxol-5-yl)sulfonyl]amino]-1S-(phenylmethyl)propyl]-2S-methyl-3-(methylthio)propanamide 1.04 g (1.94 mmoL) in 10 mL of glacial acetic acid was added 220 mg (1.94 mmoL) of 30% hydrogen peroxide with stirring. After one hour the reaction was stopped by diluting with water and neutralization by the careful addition of saturated sodium bicarbonate. The resulting aqueous suspension was extracted with ethyl acetate, and the organics were washed with 5% aqueous potassium hydrogen sulfate. The ethyl acetate layer was dried over magnesium sulfate, filtered, and concentrated to yield a mixture of diasteromeric sulfoxides. Separation of the two diastereomers by careful flash chromatography yielded 250 mg of fast moving isomer 1, and 250 mg of slow moving isomer 2, and 400 mg of the mixture, mass spectrum, m/z=559.3 (M+Li) isomer 1, and m/z =559.3 isomer 2.

EXAMPLE 53

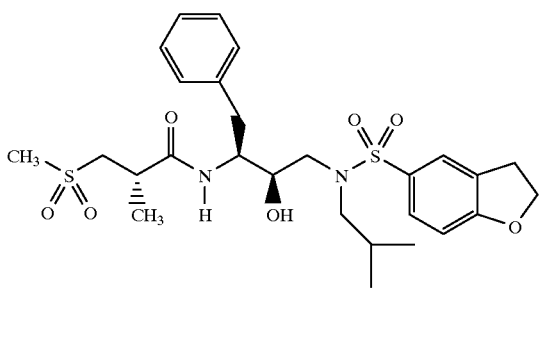

Preparation of N-[2R-hydroxy-3-[(2-methylpropyl)[(2.3-benzofuran-5-yl)sulfonyl]amino]-1S-(phenylmethyl)propyl]-2S-methyl-3-(methylsulfonyl)propanamide To a solution of 0.170 g (1 mmol) of 2-(S)-methyl-3-methylsulfonylpropionic acid dissolved in 5 mL of dry dimethylformamide was added 1.5 equivalents of N-hydroxybenzotriazole and the solution cooled in an ice bath. To this cooled solution was added 0.19 g (1.0 mmol) of EDC and the solution stirred for 30 minutes. To this was added 2R-hydroxy-3-[[(2,3-dihydrobenzofuran-5-yl)sulfonyl](2-methylpropyl)amino]-1S-(phenylmethyl)propylamine 0.418 g (1.0 mmol) and the reaction stirred for 16 hours. The contents were concentrated on a rotory evaporator and the residue was dissolved in ethyl acetate, washed with 5% potassium hydrogen sulfate, saturated sodium bicarbonate, and brine, dried over magnesium sulfate, filtered and concentrated to yield a crude oil. Purification by flash chromatograpy (SiO$_2$) using an eluant of 1:1 ethyl acetate:hexane yielded purified product: mass spectrum, m/z=573.5.

EXAMPLE 54

Preparation of 5-chlorosulfonyl-2-carbomethoxyamino-benzimidazole

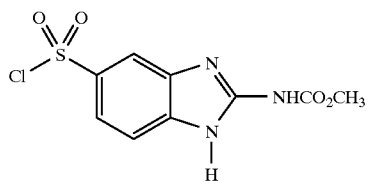

A solution of 2-carbomethoxyamino-benzimidazole (5.0 g, 0.026 mole) in chlorosulfonic acid (35.00 mL) was stirred at 0° C. for 30 minutes and at room temperature for 3 hours. The resulting dark colored reaction mixture was poured into an ice-water mixture (200 mL), and stirred at room temperature for 30 minutes. The resulting precipitate was filtered and washed with cold water (500 mL). The solid was dried overnight under high vacuum in a desiccator over NaOH pellets to give 5-chlorosulfonyl-2-carbomethoxyamino-benzimidazole (5.9 g, 78%) as a grey powder. $^1$H NMR (DMSO-d6) d: 3.89 (s, 3H), 7.55 (d, J=8.4 Hz, 1H), 7.65 (d, J=8.4 Hz, 1H), 7.88 (s, 1H). (German Patent DE 3826036)

EXAMPLE 55

Preparation of N-[2R-hydroxy-3-[N$^1$-[(2-carbomethoxyamino- benzimidazol-5-yl)sulfonyl]-N$^1$-(2-methylpropyl)amino]-1S-(phenylmethyl)propyl]carbamic acid phenylmethyl ester

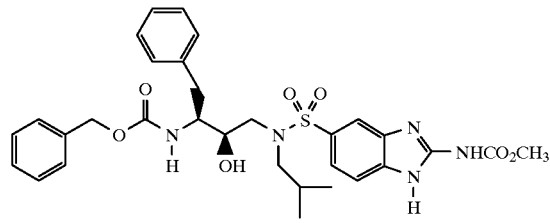

To a cold solution of N-[3S-[(phenylmethoxycarbonyl)amino]-2R-hydroxy-4-phenylbutyl]-N-(2-methylpropyl)amine (5.0 g, 13.5 mmol) in dichloromethane (70 mL) was added triethylamine (5.95 g, 54.0 mmol) followed by the addition of 5-chlorosulfonyl-2-carbomethoxyamino-benzimidazole (4.29 g, 14.85 mmol) in small portions as a solid. The reaction mixture was stirred at 0° C. for 30 minutes and at room temperature for 2.5 hours when reaction of the amino alcohol was complete. The mixture was cooled and filtered, and the filtrate was concentrated. The resulting residue was dissolved in EtOAc (200 mL), washed successively with cold 5% citric acid (3×50 mL), saturated aqueous sodium bicarbonate (3×50 mL) and water (3×100 mL), then dried (Na$_2$SO$_4$), concentrated and dried under vacuum. The residue was triturated with methanol, cooled, filtered, washed with MeOH-EtOAc (1:1, v/v) and dried in a desiccator to give pure N-[2R-hydroxy-3-[[(2-carbomethoxyamino-benzimidazol-5-yl)sulfonyl](2-methylpropyl)-amino]-1S-(phenylmethyl)propyl]carbamic acid phenylmethyl ester (6.02 g, 72%) as a light brown powder: FABMS: m/z=630 (M+Li); HRMS: calcd. for C$_{31}$H$_{38}$N$_5$O$_7$S (M+H) 624.2492, found 624.2488.

EXAMPLE 56

Preparation of 2R-hydroxy-3-[[(2-amino-benzimidazol-5-yl)sulfonyl](2-methyl-propyl)amino]-1S-(phenylmethyl)propylamine

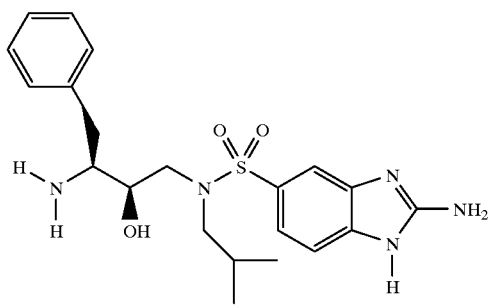

A solution of N-(2R-hydroxy-3-[C(2-carbomethoxyamino-benzimidazol-5-yl)sulfonyl](2-methylpropyl)amino]-1S-(phenylmethyl)propyl]carbamic acid phenylmethyl ester (0.36 g, 0.58 mmol) in 2.5 N methanolic KOH (2.00 mL) was heated at 70° C. under a nitrogen atmosphere for 3 hours. The reaction mixture was diluted with water (10 mL) and extracted with EtOAc (3×15 mL). The combined organic extracts were washed with brine, dried ($Na_2SO_4$) and concentrated. The resulting residue was purified by reverse-phase HPLC using a 10–90% $CH_3CN/H_2O$ gradient (30 min) at a flow rate of 70 mL/min. The appropriate fractions were combined and freeze dried to give pure 2R-hydroxy-3-[[(2-amino-benzimidazol-5-yl)sulfonyl](2-methylpropyl)amino]-1S-(phenyl-methyl)propylamine (0.22 g, 58%) as a white powder: FAB-MS m/z=432 (M+H); HRMS: calcd. for $C_{21}H_{30}N_5O_3S$ (M+H) 432.2069, found 432.2071.

EXAMPLE 57

Preparation of N-[2R-hydroxy-3-[[(2-amino-benzimidazol-5-yl)sulfonyl](2-methylpropyl)-amino]-1S-(phenylmethyl)propyl]carbamic acid phenylmethyl ester

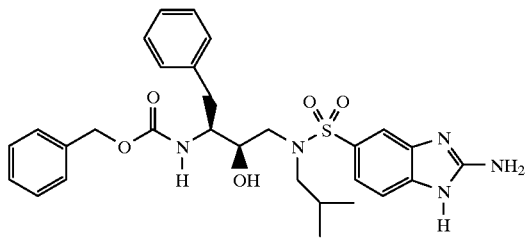

To a solution of 2R-hydroxy-3-[[(2-amino-benzimidazol-5-yl)sulfonyl](2-methyl-propyl)amino]-1S-(phenylmethyl)propylamine (0.22 g, 0.33 mmol) in THF (3.00 mL), triethylamine (0.11 g, 1.1 mmol) and benzyloxycarbonyl succinimide (0.09 g, 0.36 mmol) were added, and the reaction mixture was stirred at room temperature for 16 hours. The solution was concentrated, and the residue was partitioned between EtOAc (15 mL) and saturated aqueous sodium bicarbonate. The organic phase was washed with brine, dried ($Na_2SO_4$), and concentrated. The resulting residue was purified by reverse-phase HPLC using a 10–90% $CH_3CN/H_2O$ gradient (30 min) at a flow rate of 70 mL/min. The appropriate fractions were combined and freeze dried to give pure N-[2R-hydroxy-3-[[(2-amino-benzimidazol-5-yl)sulfonyl](2-methylpropyl)amino]-1S-(phenylmethyl)propyl]carbamic acid phenylmethyl ester (0.12 g, 61%) as a white powder: FAB-MS m/z=566 (M+H); HRMS: calcd. for $C_{29}H_{36}N_5O_5S$ 566.2437 (M+H), found 566.2434.

EXAMPLE 58

Preparation of 2R-hydroxy-3-[[(2-carbomethoxyamino-benzimidazol-5-yl)sulfonyl](2-methylpropyl)amino]-1S-(phenylmethyl)propylamine

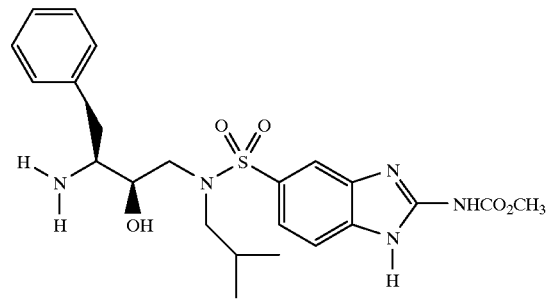

A solution of N-[2R-hydroxy-3-[[(2-carbomethoxyamino-benzimidazole-5-yl)sulfonyl](2-methylpropyl)-amino]-1S-(phenylmethyl)propyl]carbamic acid phenylmethyl ester (2.5 g, 0.4 mmol) in MeOH (10 mL) and THF (50 mL) was hydrogenated in the presence of 10% Pd/C (1.2 g) at room temperature at 60 psi for 16 hours. The catalyst was removed by filtration, and the filtrate was concentrated under reduced pressure. The resulting residue was triturated with ether and filtered. The solid substance thus obtained was washed with ether and dried in vacuo to afford pure 2R-hydroxy-3-[[(2-carbomethoxyamino-benzimidazol-5-yl)sulfonyl](2-methylpropyl)amino]-1S-(phenylmethyl)propylamine (1.5 g, 77%) as an off white powder: $R_t$=12.8 min; FAB-MS m/z=490 (M+H); HRMS: calcd. for $C_{23}H_{32}N_5O_5S$ 490.2124 (M+H), found 490.2142.

EXAMPLE 59

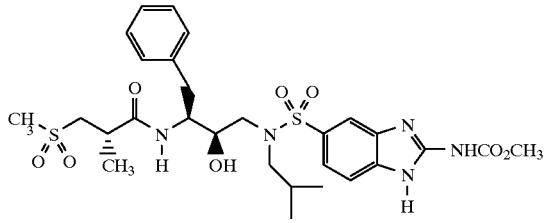

Preparation of N-[2R-hydroxy-3-[(2-methylpropyl)[(2-(carbomethoxyamino)benzimidazol-5-yl)sulfonyl]amino]-l1S-(phenylmethyl)propyl]-2S-methyl-3-(methylsulfonyl)propanamide A mixture of 2-(S)-methyl-3-methylsulfonyl propionic acid (157.0 mg, 0.94 mmol), 1-hydroxybenzotriazole hydrate (144.0 mg, 0.94 mmol), and 1-(3-dimethylamino-propyl)-3-ethylcarbodiimide hydrochloride (EDC) (180.0 mg, 0.94 mmol) was dissolved in dimethylformamide (5.0 mL), and the solution was stirred at room temperature for 45 minutes. Then 2R-hydroxy-3-([(2-(carbomethoxyamino)benzimidazol-5-yl)sulfonyl](2-methylpropyl)amino]-1S-(phenylmethyl)propylamine (459 mg, 0.94 mmol) and N-methylmorpholine (202.0 mg, 2.0 mmol) were added, and the reaction stirred at room temperature for 16 hours. The solution was poured into ethyl acetate (75 mL), and the ethyl acetate layer was washed with 10% aqueous acetic acid (3×25 mL), saturated aqueous sodium bicarbonate (3×25 mL) and saturated aqueous sodium chloride (25 mL). The organic layer was dried over anhydrous sodium sulfate, and the solvent removed in vacuo. The resulting residue was dissolved in hot ethyl acetate (25 mL). The solution was cooled to room temperature and a precipitate began to form. Hexanes (25 mL) were added and the solution was stirred at room temperature for 2 hours. The resulting product was collected by vacuum filtration to give pure N-[2R-hydroxy-3-[(2-methylpropyl)[(2-(carbomethoxyamino)benzimidazol-5-yl)sulfonyl]amino]-1S-(phenylmethyl)propyl]-2S-methyl-3-(methyl-sulfonyl)-propanamide as a white solid (395 mg, 65%); FAB-MS calcd for $C_{28}H_{39}N_5O_8S_2$ m/z 637 (M+H), found m/z=644 (M+Li).

EXAMPLE 60

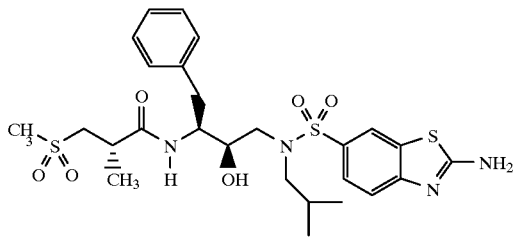

Preparation of N-[2R-hydroxy-3-[(2-methylpropyl)[(2-aminobenzothiazol-6-yl)sulfonyl]amino]-1S-(phenylmethyl)propyl]-2S-methyl-3-(methylsulfonyl)propanamide To a solution of 2-(S)-methyl-3-methylsulfonyl propionic acid (0.249 g, 1.5 mmol) in 5 mL of dry dimethylformamide, was added 1.5 equivalents of N-hydroxy-benzotriazole, and the solution was cooled in an ice bath. To this cooled solution was added EDC (0.200 g, 1.5 mmol), and the solution was stirred for 30 minutes. To this was added 2R-hydroxy-3-[[(2-aminobenzothiazol-6-yl)sulfonyl](2-methyl-propyl)amino]-1S-(phenylmethyl)propylamine (0.673 g, 1.5mmol), and the reaction stirred for 16 hours. The contents were concentrated in vacuo and the residue was dissolved in ethyl acetate, washed with 5% potassium hydrogen sulfate, saturated sodium bicarbonate, and brine, dried over magnesium sulfate, filtered and concentrated to yield a crude oil. Purification by flash column chromatograpy on silica gel using an eluant of 1:1:0.1 ethyl acetate: hexane:methanol yielded pure N-[2R-hydroxy-3-[(2-methylpropyl) [(2-amino-benzothiazol-6-yl)sulfonyl] amino]-1S-(phenylmethyl)propyl]-2S-methyl-3-(methyl-sulfonyl)propanamide; FAB-MS: m/z=598.6 (M+H).

EXAMPLE 61

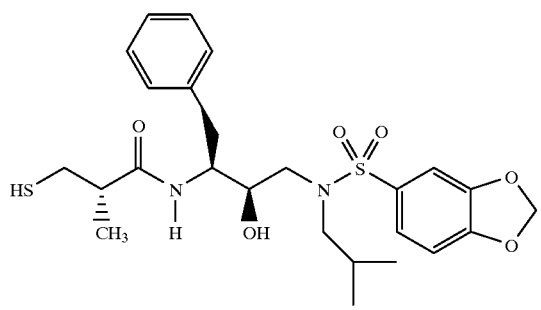

Preparation of N-[2R-hydroxy-3-[(2-methylpropyl)[(1.3-benzodioxol-5-yl)sulfonyl]-amino]-1S-(phenylmethyl)propyl]-2S-methyl-3-mercaptopropanamide Part A Preparation of N-[2R-hydroxy-3-[(2-methylpropyl)[(1,3-benzodioxol-5-yl)sulfonyl]amino]-1S-(phenylmethyl)propyl]-2S-methyl-3-(acetylthio)-propanamide N-Hydroxybenzotriazole (1.64 g, 10.7 mmol) was added to solution of D-(−)-S-acetyl-β-mercaptoisobutyric acid (1.16 g, 7.1 mmol) in 12 mL of dry dimethylformamide and cooled in an ice bath. To the cooled solution, was added EDC (1.5 g, 7.8 mmol), and the reaction was then stirred for 60 minutes. To this was added (3 g, 7.1 mmol) of 2R-hydroxy-3-[[(1,3-benzodioxol-5-yl)sulfonyl](2-methylpropyl)-amino]-1S-(phenylmethyl)propylamine, and this was stirred for 16 hours with warming to room temperature. The solvent was removed and the residue partitioned between ethyl acetate and 5% aqueous potassium hydrogen sulfate. The organic layer was washed with saturated sodium bicarbonate, brine, dried over magnesium sulfate, filtered, and concentrated to yield 3.7 g (91%) of the desired product as a crude oil; mass spectrum, m/z=571.8 (M+Li).

Part B

Preparation of N-[2R-hydroxy-3-[(2-methylpropyl)[(1,3-benzodioxol-5-yl)sulfonyl]amino]-1S-(phenylmethyl)propyl]-2S-methyl-3-mercaptopropanamide A solution of 4.29 g, (7.8 mmol) of the S-acetyl compound from Part A dissolved in 100 mL of dry methanol was cooled in an ice bath. Anhydrous ammonia was bubbled into the solution for one minute. The solution was stoppered and stirred at room temperature over 5 hours. The contents were concentrated on a rotory evaporator, and the residue was dissolved in ethyl acetate. The organic solution was washed with water, brine, dried over magnesium sulfate, filtered and concentrated to yield 3.9 g (95.6%) of the free mercaptan which was used without further purification; mass spectrum, m/z=529.8 (M+Li).

EXAMPLE 62

Following the procedures of the previous Examples, the compounds set forth in Tables 2 through 8 can be prepared.

TABLE 2

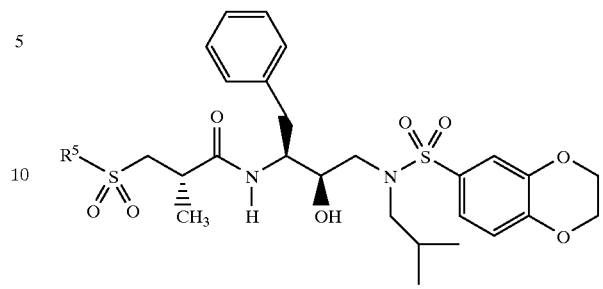

| Entry | R³ | R⁴ |
|---|---|---|
| 1 | isobutyl | 2-methyl-1,3-benzodioxol-5-yl |
| 2 | isobutyl | 2-methyl-1,3-benzodioxol-5-yl |
| 3 | cyclopentylmethyl | 2-methyl-1,3-benzodioxol-5-yl |
| 4 | cyclohexylmethyl | 2-methyl-1,3-benzodioxol-5-yl |
| 5 | cyclopentylmethyl | 1,3-benzodioxol-5-yl |
| 6 | cyclohexylmethyl | 1,3-benzodioxol-5-yl |
| 7 | cyclopentylmethyl | benzofuran-5-yl |
| 8 | cyclohexylmethyl | benzofuran-5-yl |
| 9 | cyclopentylmethyl | 2,3-dihydrobenzofuran-5-yl |
| 10 | cyclohexylmethyl | 2,3-dihydrobenzofuran-5-yl |
| 11 | isobutyl | 1,3-benzodioxol-5-yl |
| 12 | isobutyl | benzofuran-5-yl |
| 13 | isobutyl | 2,3-dihydrobenzofuran-5-yl |
| 14 | isobutyl | 1,4-benzodioxan-6-yl |
| 15 | isoamyl | 1,3-benzodioxol-5-yl |
| 16 | isoamyl | 2,3-dihydrobenzofuran-5-yl |
| 17 | isoamyl | 1,4-benzodioxan-6-yl |
| 18 | isobutyl | benzothiazol-6-yl |
| 19 | isobutyl | 2-amino-benzothiazol-6-yl |
| 20 | isobutyl | benzoxazol-5-yl |
| 21 | cyclopentylmethyl | 2,2-difluoro-1,3-benzodioxol-5-yl |
| 22 | cyclohexylmethyl | 2,2-difluoro-1,3-benzodioxol-5-yl |

TABLE 3A

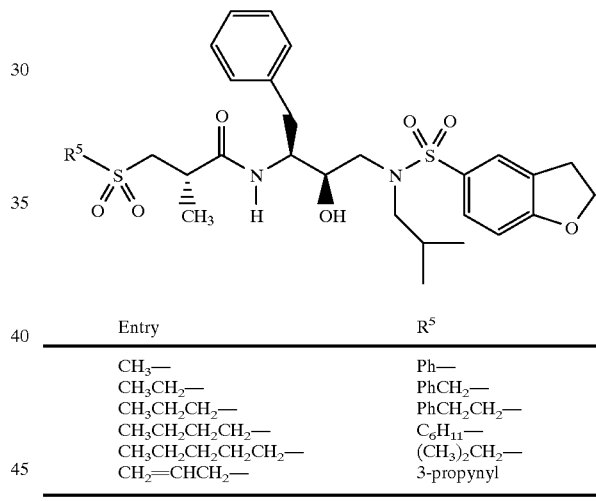

| Entry | R⁵ | |
|---|---|---|
| | CH₃— | Ph— |
| | CH₃CH₂— | PhCH₂— |
| | CH₃CH₂CH₂— | PhCH₂CH₂— |
| | CH₃CH₂CH₂CH₂— | C₆H₁₁— |
| | CH₃CH₂CH₂CH₂CH₂— | (CH₃)₂CH₂— |
| | CH₂=CHCH₂— | 3-propynyl |

TABLE 3B (same structure with 1,4-benzodioxane substituent)

| Entry | R⁵ | |
|---|---|---|
| | CH₃— | Ph— |
| | CH₃CH₂— | PhCH₂— |
| | CH₃CH₂CH₂— | PhCH₂CH₂— |
| | CH₃CH₂CH₂CH₂— | C₆H₁₁— |
| | CH₃CH₂CH₂CH₂CH₂— | (CH₃)₂CH₂— |
| | CH₂=CHCH₂— | 3-propynyl |

TABLE 3C

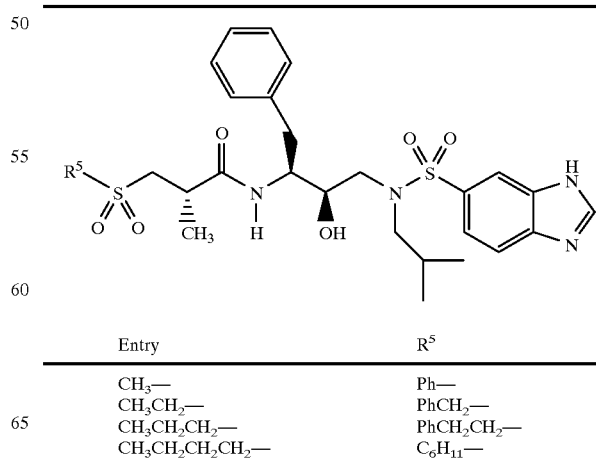

| Entry | R⁵ | |
|---|---|---|
| | CH₃— | Ph— |
| | CH₃CH₂— | PhCH₂— |
| | CH₃CH₂CH₂— | PhCH₂CH₂— |
| | CH₃CH₂CH₂CH₂— | C₆H₁₁— |
| | CH₃CH₂CH₂CH₂CH₂— | (CH₃)₂CH₂— |
| | CH₂=CHCH₂— | 3-propynyl |

TABLE 3D (benzimidazole substituent)

| Entry | R⁵ | |
|---|---|---|
| | CH₃— | Ph— |
| | CH₃CH₂— | PhCH₂— |
| | CH₃CH₂CH₂— | PhCH₂CH₂— |
| | CH₃CH₂CH₂CH₂— | C₆H₁₁— |

TABLE 3D-continued

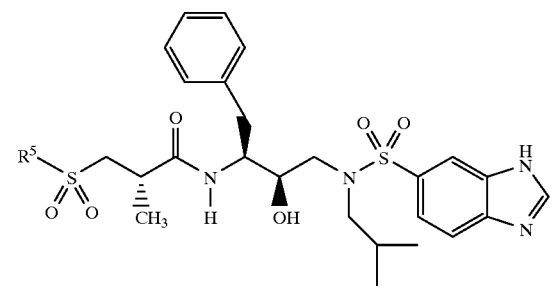

| Entry | R⁵ |
|---|---|
| CH₃CH₂CH₂CH₂CH₂— | (CH₃)₂CH₂— |
| CH₂=CHCH₂— | 3-propynyl |

TABLE 3E

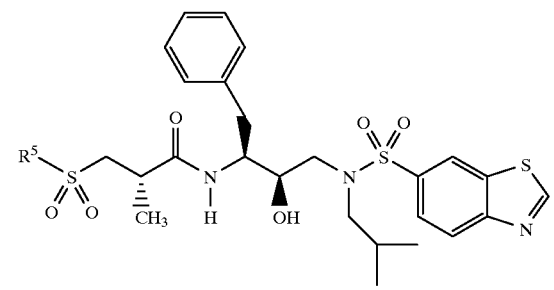

| Entry | R⁵ |
|---|---|
| CH₃— | Ph— |
| CH₃CH₂— | PhCH₂— |
| CH₃CH₂CH₂— | PhCH₂CH₂— |
| CH₃CH₂CH₂CH₂— | C₆H₁₁— |
| CH₃CH₂CH₂CH₂CH₂— | (CH₃)₂CH₂— |
| CH₂=CHCH₂— | 3-propynyl |

TABLE 3F

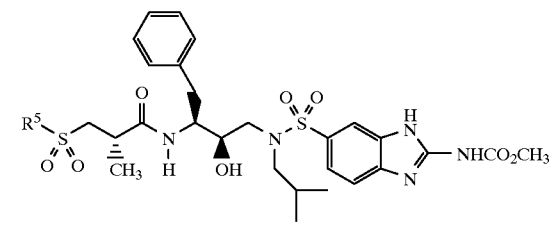

| Entry | R⁵ |
|---|---|
| CH₃— | Ph— |
| CH₃CH₂— | PhCH₂— |
| CH₃CH₂CH₂— | PhCH₂CH₂— |
| CH₃CH₂CH₂CH₂— | C₆H₁₁— |
| CH₃CH₂CH₂CH₂CH₂— | (CH₃)₂CH₂— |
| CH₂=CHCH₂— | 3-propynyl |

TABLE 3G

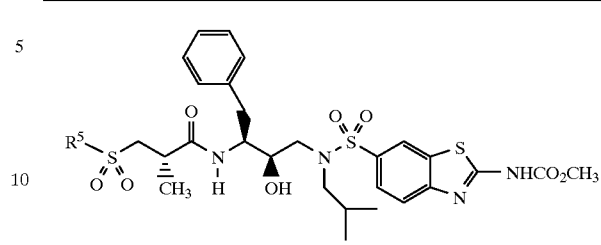

| Entry | R⁵ |
|---|---|
| CH₃— | Ph— |
| CH₃CH₂— | PhCH₂— |
| CH₃CH₂CH₂— | PhCH₂CH₂— |
| CH₃CH₂CH₂CH₂— | C₆H₁₁— |
| CH₃CH₂CH₂CH₂CH₂— | (CH₃)₂CH₂— |
| CH₂=CHCH₂— | 3-propynyl |

TABLE 4A

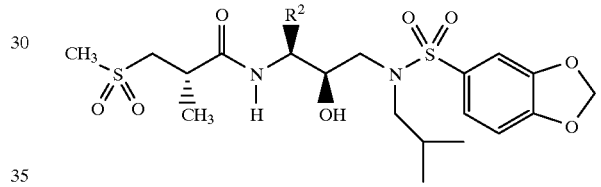

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 4B

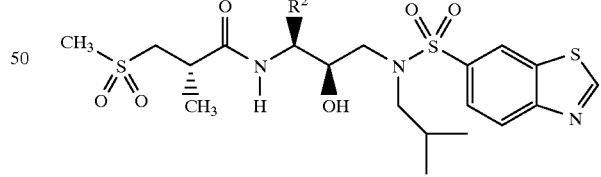

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 4C

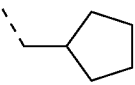

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 4D

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 4E

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 4F

| Entry | R² |
|---|---|
| (CH₃)₂CHCH₂— | (4-FC₆H₅)CH₂— |
| CH₃CH₂CH₂CH₂— | (naphth-2-yl)CH₂— |

TABLE 4F-continued

| Entry | R² |
|---|---|
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 4G

| Entry | R² |
|---|---|
| (CH₃)₂CHCH₂— | (4-FC₆H₅)CH₂— |
| CH₃CH₂CH₂CH₂— | (naphth-2-yl)CH₂— |
| CH₃SCH₂CH₂— | C₆H₁₁CH₂— |
| C₆H₅CH₂— | C₆H₅SCH₂— |
| (4-CH₃OC₆H₅)CH₂— | (naphth-2-yl)SCH₂— |

TABLE 5A

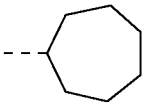

| Entry | R³ |
|---|---|
| —CH₂CH₂CH₃ | 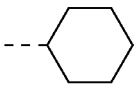 |
| —CH₂CH₂CH₂CH₃ | |
| —CH₂CH(CH₃)₂ | |
| —CH₂CH₂CH(CH₃)₂ | |

TABLE 5A-continued

[Structure: (methylsulfonyl)propanamide with phenyl, hydroxyl, and benzodioxole sulfonamide groups, N-R³]

| Entry | R³ |
|---|---|
| | cyclohexylmethyl |

TABLE 5B

[Structure: (methylsulfonyl)propanamide with phenyl, hydroxyl, and 2,3-dihydrobenzofuran sulfonamide groups, N-R³]

| Entry | R³ |
|---|---|
| —CH₂CH₂CH₃ | |
| —CH₂CH₂CH₂CH₃ | |
| —CH₂CH(CH₃)₂ | |
| —CH₂CH₂CH(CH₃)₂ | |
| | cyclopentyl |
| | cyclopentylmethyl |
| | cycloheptyl |
| | cyclohexyl |
| | cyclohexylmethyl |

TABLE 5C

[Structure: (methylsulfonyl)propanamide with phenyl, hydroxyl, and 2,3-dihydro-1,4-benzodioxin sulfonamide groups, N-R³]

| Entry | R³ |
|---|---|
| —CH₂CH₂CH₃ | |
| —CH₂CH₂CH₂CH₃ | |
| —CH₂CH(CH₃)₂ | |
| —CH₂CH₂CH(CH₃)₂ | |
| | cyclopentyl |
| | cyclopentylmethyl |
| | cycloheptyl |
| | cyclohexyl |
| | cyclohexylmethyl |

TABLE 5D

[Structure: (methylsulfonyl)propanamide with phenyl, hydroxyl, and benzothiazole sulfonamide groups, N-R³]

| Entry | R³ |
|---|---|
| —CH₂CH₂CH₃ | |
| —CH₂CH₂CH₂CH₃ | |
| —CH₂CH(CH₃)₂ | |
| —CH₂CH₂CH(CH₃)₂ | |
| | cyclopentyl |
| | cyclopentylmethyl |

TABLE 5D-continued

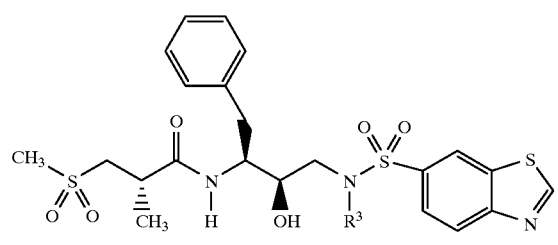

| Entry | R³ |
|---|---|
| | cycloheptyl |
| | cyclohexyl |
| | CH₂-cyclohexyl |

TABLE 5E

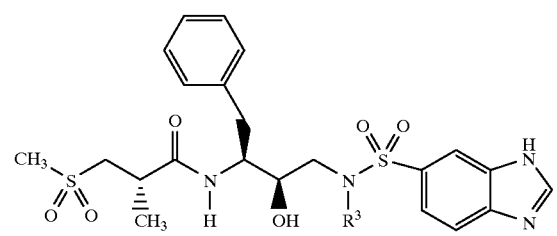

| Entry | R³ |
|---|---|
| —CH₂CH₂CH₃<br>—CH₂CH₂CH₂CH₃<br>—CH₂CH(CH₃)₂<br>—CH₂CH₂CH(CH₃)₂ | cyclopentyl |
| | CH₂-cyclopentyl |
| | cycloheptyl |
| | cyclohexyl |

TABLE 5E-continued

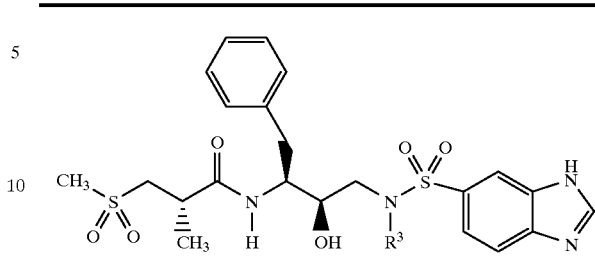

| Entry | R³ |
|---|---|
| | CH₂-cyclohexyl |

TABLE 5F

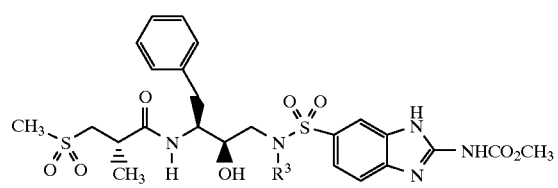

| Entry | R³ |
|---|---|
| —CH₂CH₂CH₃<br>—CH₂CH₂CH₂CH₃<br>—CH₂CH(CH₃)₂<br>—CH₂CH₂CH(CH₃)₂ | cyclopentyl |
| | CH₂-cyclopentyl |
| | cycloheptyl |
| | cyclohexyl |
| | CH₂-cyclohexyl |

TABLE 6A
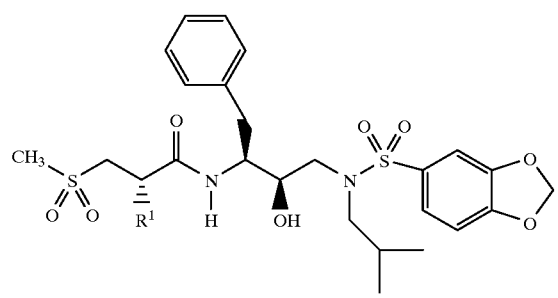
Entry R¹
TABLE 6B
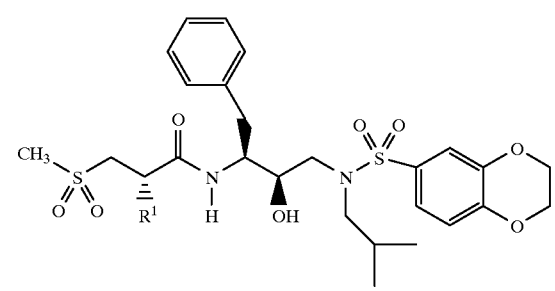
Entry R¹
TABLE 6B-continued
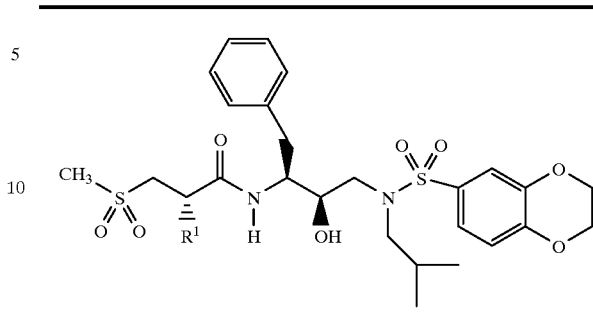
Entry R¹
TABLE 6C
Entry R¹
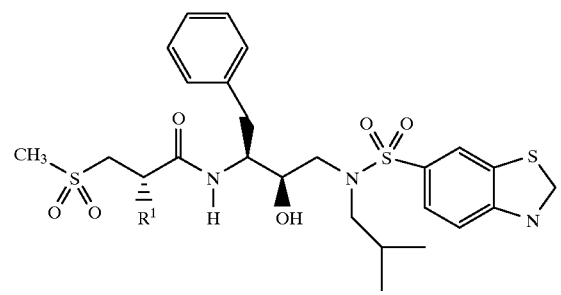

TABLE 6D
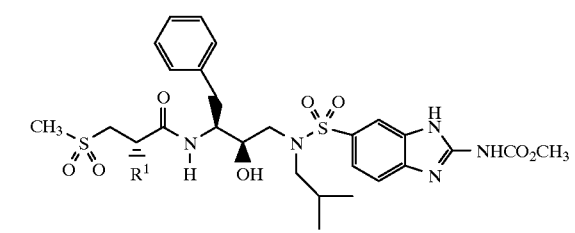
| Entry | R¹ |
|---|---|
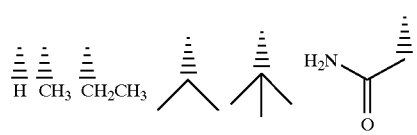
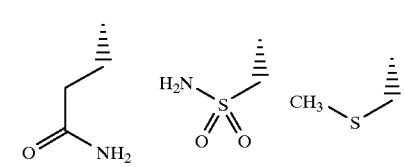
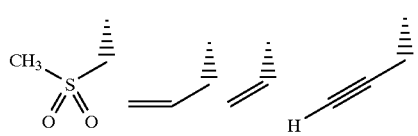
TABLE 6E
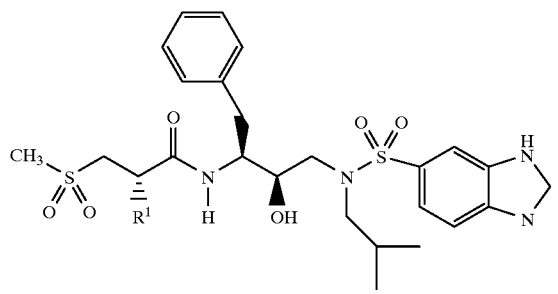
| Entry | R¹ |
|---|---|
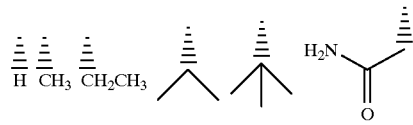
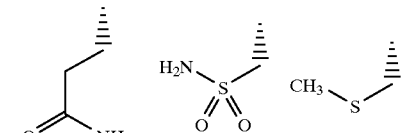
TABLE 6E-continued
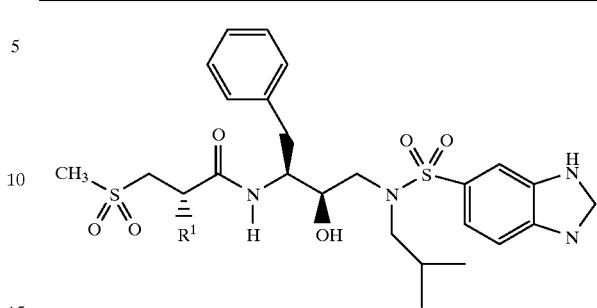
| Entry | R¹ |
|---|---|
TABLE 6F
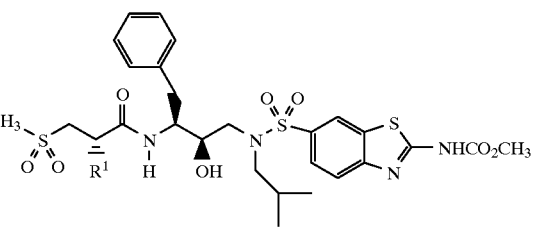
| Entry | R¹ |
|---|---|
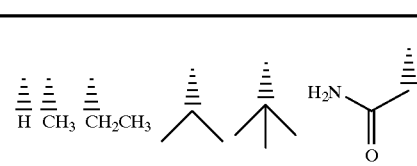

TABLE 6G

[Structure: core scaffold with R¹ substituent]

| Entry | R¹ |
|---|---|
| | H, CH₃, CH₂CH₃, isopropyl, tert-butyl, -CH₂C(O)NH₂ |
| | -CH₂CH₂C(O)NH₂, -CH₂S(O)₂NH₂, -CH₂SCH₃ |
| | -CH₂S(O)₂CH₃, allyl, allyl, propargyl |

TABLE 7

[Structure: core scaffold with R⁴ substituent, ethyl group at stereocenter]

| Entry | R⁴ |
|---|---|
| | benzo[1,3]dioxole-5-yl, 2,3-dihydrobenzo[1,4]dioxin-6-yl |
| | 2,3-dihydrobenzofuran-5-yl, 2-methyl-benzo[1,3]dioxol-5-yl |

TABLE 7-continued

| Entry | R⁴ |
|---|---|
| | benzothiazol-6-yl, benzothiazol-5-yl |
| | isoquinolin-7-yl, 2,2-dimethyl-benzo[1,3]dioxol-5-yl |
| | quinolin-7-yl, isoquinolin-6-yl |
| | quinolin-6-yl, 2,2-dichloro-benzo[1,3]dioxol-5-yl |
| | chroman-6-yl, benzoxazol-6-yl |
| | benzoxazol-5-yl, 2,2-difluoro-benzo[1,3]dioxol-5-yl |
| | benzimidazol-5-yl, 2-amino-benzothiazol-6-yl |
| | 2-amino-benzothiazol-5-yl, benzofuran-5-yl |
| | 2,2-dideutero-benzo[1,3]dioxol-5-yl |

TABLE 7-continued

[Structure: phenyl-CH2-CH(NH-C(=O)-CH(CH2CH3)-CH2-S(=O)2-CH3)-CH(OH)-CH2-N(CH2CH(CH3)2)-S(=O)2-R4]

| Entry | R4 |
|---|---|
| | 5-benzimidazolyl-2-NHCO2CH3 (NH) |
| | 5-benzothiazolyl-2-NHCO2CH3 (S,N) |
| | 5-benzothiazolyl-2-NHCO2CH3 (N,S) |

TABLE 8A

[Structure: phenyl-CH2-CH(NH-C(=O)-CH(CH3)-CH2-S(=O)2-CH3)-CH(OH)-CH2-N(CH2CH(CH3)2)-S(=O)2-R4]

| Entry | R4 | |
|---|---|---|
| | 5-benzo[1,3]dioxolyl | 6-benzo[1,4]dioxanyl |
| | 5-(2,3-dihydrobenzofuranyl) | 5-benzo[1,3]dioxolyl-2-CH3 |
| | 5-benzothiazolyl | 5-benzothiazolyl |

TABLE 8A-continued

[Structure: same as TABLE 8A]

| Entry | R4 | |
|---|---|---|
| | 7-isoquinolinyl | 5-benzo[1,3]dioxolyl-2,2-(CH3)2 |
| | 7-quinolinyl | 6-isoquinolinyl |
| | 6-quinolinyl | 5-benzo[1,3]dioxolyl-2,2-Cl2 |
| | 6-chromanyl | 6-benzoxazolyl |
| | 5-benzoxazolyl | 5-benzo[1,3]dioxolyl-2,2-F2 |
| | 5-benzimidazolyl (NH) | 6-benzothiazolyl-2-NH2 |
| | 5-benzothiazolyl-2-NH2 | 5-benzofuranyl |
| | 5-benzo[1,3]dioxolyl-2,2-D2 | |
| | 5-benzimidazolyl-2-NHCO2CH3 (NH) | |

TABLE 8A-continued

[Structure: CH₃-S(O₂)-CH₂-CH(CH₃)-C(O)-NH-CH(CH₂Ph)-CH(OH)-CH₂-N(iBu)-SO₂-R⁴]

| Entry | R⁴ |
|---|---|
| | 6-(2-NHCO₂CH₃)-benzothiazolyl |
| | 5-(2-NHCO₂CH₃)-benzothiazolyl |

TABLE 8B

[Structure: CH₃-S(O)-CH₂-CH(CH₃)-C(O)-NH-CH(CH₂Ph)-CH(OH)-CH₂-N(iBu)-SO₂-R⁴]

| Entry | R⁴ |
|---|---|
| | benzo[1,3]dioxol-5-yl |
| | 2,3-dihydro-benzo[1,4]dioxin-6-yl |
| | 2,3-dihydro-benzofuran-5-yl |
| | 2-methyl-benzo[1,3]dioxol-5-yl |
| | benzothiazol-6-yl |
| | benzothiazol-5-yl |
| | isoquinolin-7-yl |
| | 2,2-dimethyl-benzo[1,3]dioxol-5-yl |

TABLE 8B-continued

[Structure: CH₃-S(O)-CH₂-CH(CH₃)-C(O)-NH-CH(CH₂Ph)-CH(OH)-CH₂-N(iBu)-SO₂-R⁴]

| Entry | R⁴ |
|---|---|
| | quinolin-7-yl |
| | isoquinolin-6-yl |
| | quinolin-6-yl |
| | 2,2-dichloro-benzo[1,3]dioxol-5-yl |
| | chroman-6-yl |
| | benzo[1,3]oxazol-6-yl |
| | benzo[1,3]oxazol-5-yl |
| | 2,2-difluoro-benzo[1,3]dioxol-5-yl |
| | benzimidazol-5-yl |
| | 2-amino-benzothiazol-6-yl |
| | 2-amino-benzothiazol-5-yl |
| | benzofuran-5-yl |
| | 2,2-dideutero-benzo[1,3]dioxol-5-yl |
| | 2-(NHCO₂CH₃)-benzimidazol-5-yl |
| | 2-(NHCO₂CH₃)-benzothiazol-6-yl |

TABLE 8B-continued
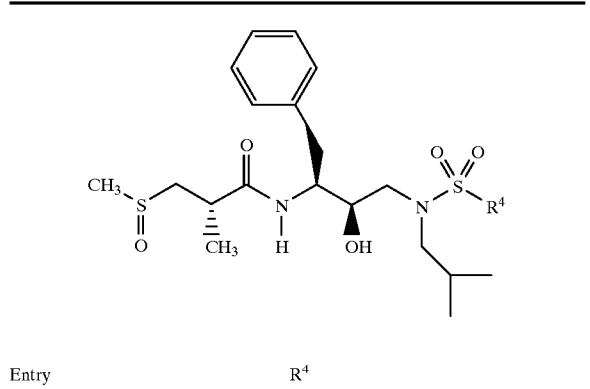
| Entry | R⁴ |
|---|---|
| |  |
TABLE 8C
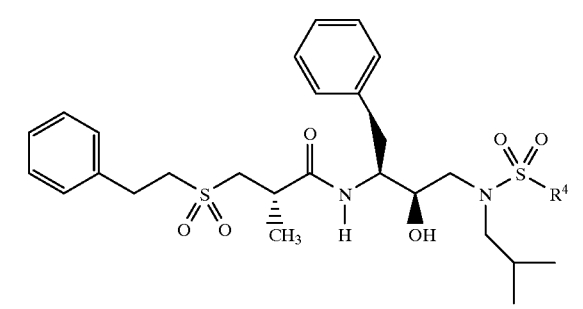
| Entry | R⁴ |
|---|---|
| |   |
| | 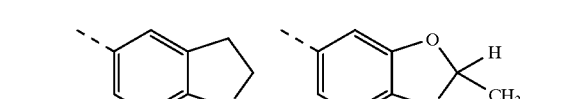 |
| | 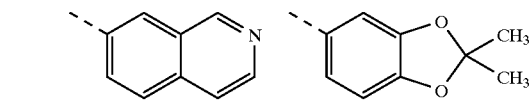 |
TABLE 8C-continued
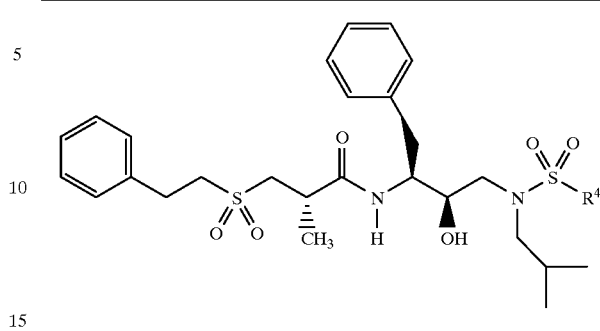
| Entry | R⁴ |
|---|---|
| | 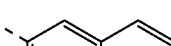 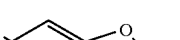 |
| | 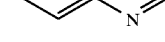 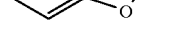 |
| | 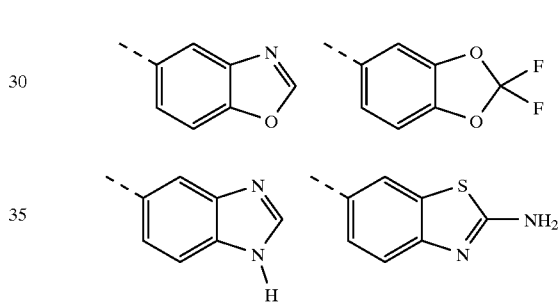 |
| |  |
| | 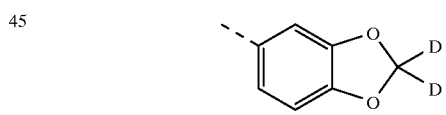 |
| |  |
| | 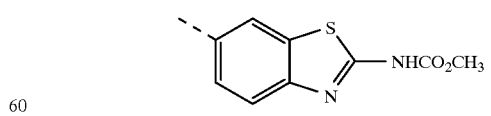 |
| |  |

TABLE 8D

[Structure: Phenethyl-S(=O)-CH2-CH(CH3)-C(=O)-NH-CH(CH2Ph)-CH(OH)-CH2-N(iBu)-S(=O)2-R4]

| Entry | R4 |
|---|---|
| | benzo[1,3]dioxole-5-yl |
| | 2,3-dihydrobenzo[1,4]dioxine-6-yl |
| | 2,3-dihydrobenzofuran-5-yl |
| | 2-methyl-benzo[1,3]dioxole-5-yl |
| | benzothiazole-5-yl |
| | benzothiazole-6-yl |
| | isoquinoline-7-yl |
| | 2,2-dimethyl-benzo[1,3]dioxole-5-yl |
| | quinoline-7-yl |
| | isoquinoline-6-yl |
| | quinoline-6-yl |
| | 2,2-dichloro-benzo[1,3]dioxole-5-yl |
| | chroman-6-yl |
| | benzoxazole-5-yl |
| | benzoxazole-6-yl |
| | 2,2-difluoro-benzo[1,3]dioxole-5-yl |
| | benzimidazole-5-yl |
| | 2-amino-benzothiazole-6-yl |

TABLE 8D-continued

[Same core structure]

| Entry | R4 |
|---|---|
| | 2-amino-benzothiazole-5-yl |
| | benzofuran-5-yl |
| | 2,2-dideutero-benzo[1,3]dioxole-5-yl |
| | 2-(NHCO2CH3)-benzimidazole-5-yl |
| | 2-(NHCO2CH3)-benzothiazole-6-yl |
| | 2-(NHCO2CH3)-benzothiazole-5-yl |

EXAMPLE 62

The compounds of the present invention are effective HIV protease inhibitors. Utilizing an enzyme assay as described below, the compounds set forth in the examples herein disclosed inhibited the HIV enzyme. The preferred compounds of the present invention and their calculated $IC_{50}$ (inhibiting concentration 50%, i.e., the concentration at which the inhibitor compound reduces enzyme activity by 50%) values are shown in Table 9. The enzyme method is described below. The substrate is 2-Ile-Nle-Phe(p-$NO_2$)-Gln-Arg$NH_2$. The positive control is MVT-101 (Miller, M. et al, *Science,* 246, 1149 (1989)] The assay conditions are as follows:

Assay buffer 20 mM sodium phosphate, pH 6.4

20% glycerol 1 mM EDTA 1 mM DTT 0.1% CHAPS

The above described substrate is dissolved in DMSO, then diluted 10 fold in assay buffer. Final substrate concentration in the assay is 80 μM. HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 µl of the enzyme preparation is added, the materials mixed and then the mixture is incubated at ambient temperature for 15 minutes. The enzyme reaction is initiated by the addition of 40 µl of substrate. The increase in fluorescence is monitored at 4 time points (0, 8, 16 and 24 minutes) at ambient temperature. Each assay is carried out in duplicate wells.

The preceding examples can be repeated with similar success by substituting the generically or specifically described reactants and/or operating conditions of this invention for those used in the preceding examples.

EXAMPLE 63

The effectiveness of various compounds were determined in the above-described enzyme assay and in a CEM cell assay.

The HIV inhibition assay method of acutely infected cells is an automated tetrazolium based colorimetric assay essentially that reported by Pauwles et al, *J. Virol. Methods*, 20, 309–321 (1988). Assays were performed in 96-well tissue culture plates. CEM cells, a CD4+ cell line, were grown in RPMI-1640 medium (Gibco) supplemented with a 10% fetal calf serum and were then treated with polybrene (2 µg/ml). An 80 µl volume of medium containing 1×10$^4$ cells was dispensed into each well of the tissue culture plate. To each well was added a 100µl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ TCID$_{50}$ per ml (TCID$_{50}$=the dose of virus that infects 50% of cells in tissue culture), and a 20 µL volume of the virus sample (containing 1000 TCID$_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

| | Cells | Drug | Virus |
|---|---|---|---|
| 1. | + | − | − |
| 2. | + | + | − |
| 3. | + | − | + |
| 4. | + | + | + |

In experiments 2 and 4 the final concentrations of test compounds were 1, 10, 100 and 500 µg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% CO$_2$ atmosphere for 7 days. Test compounds could be added on days 0, 2 and 5 if desired. On day 7, post-infection, the cells in each well were resuspended and a 100 µl sample of each cell suspension was removed for assay. A 20 µL volume of a 5 mg/ml solution of 3-(4,5-dimethylthiazol-2-yl)-2,5-diphenyltetrazolium bromide (MTT) was added to each 100 µL cell suspension, and the cells were incubated for 4 hours at 27° C. in a 5% CO$_2$ environment. During this incubation, MTT is metabolically reduced by living cells resulting in the production in the cell of a colored formazan product. To each sample was added 100 µl of 10% sodium dodecylsulfate in 0.01 N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 9

| Entry | Compound | IC$_{50}$ (nM) | EC$_{50}$ (nM) |
|---|---|---|---|
| 1 | | 2 | 20 |

TABLE 9-continued

| Entry | Compound | IC$_{50}$ (nM) | EC$_{50}$ (nM) |
|---|---|---|---|
| 2 | | 2 | 28 |
| 3 | | 3 | 26 |
| 4 | | 2 | 12 |
| 5 | | 2 | 52 | isomer 1, Example 52

TABLE 9-continued

| Entry | Compound | IC$_{50}$ (nM) | EC$_{50}$ (nM) |
|---|---|---|---|
| 6 | 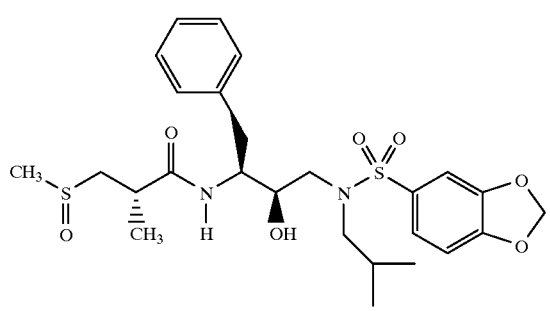<br>isomer 2, Example 52 | 7 | 80 |

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment, proplylaxis of retroviral infections and/or the prevention of the spread of retroviral infections.

The subject compounds are also effective in preventing the growth of retroviruses in a solution. Both human and animal cell cultures, such as T-lymphocyte cultures, are utilized for a variety of well known purposes, such as research and diagnostic procedures including calibrators and controls. Prior to and during the growth and storage of a cell culture, the subject compounds may be added to the cell culture medium at an effective concentration to prevent the unexpected or undesired replication of a retrovirus that may inadvertently, unknowingly or knowingly be present in the cell culture. The virus may be present originally in the cell culture, for example HIV is known to be present in human T-lymphocytes long before it is detectable in blood, or through exposure to the virus. This use of the subject compounds prevents the unknowing or inadvertent exposure of a potentially lethal retrovirus to a researcher or clinician.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen- containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with glucosidase inhibitors, such as N-butyl-1-deoxynojirimycin or prodrugs thereof, for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound represented by the formula:

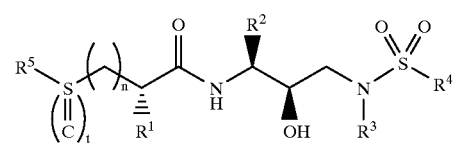

or a pharmaceutically acceptable salt, prodrug or ester thereof, wherein n and t each independently represent 0, 1 or 2;

$R^1$ represents hydrogen, alkyl of 1–5 carbon atoms, alkenyl of 2–5 carbon atoms, alkynyl of 2–5 carbon atoms, hydroxyalkyl of 1–3 carbon atoms, alkoxyalkyl of 1–3 alkyl and 1–3 alkoxy carbon atoms, cyanoalkyl of 1–3 alkyl carbon atoms, —CH$_2$CONH$_2$, —CH$_2$CH$_2$CONH$_2$, —CH$_2$S(O)$_2$NH$_2$, —CH$_2$SCH$_3$, —CH$_2$S(O)CH$_3$ or —CH$_2$S(O)$_2$CH$_3$ radicals;

$R^2$ represents radicals of alkyl of 1–5 carbon atoms, aralkyl of 1–3 alkyl carbon atoms, alkylthioalkyl of 1–3 alkyl carbon atoms, arylthioalkyl of 1–3 alkyl carbon atoms or cycloalkylalkyl of 1–3 alkyl carbon atoms and 3–6 ring member carbon atoms;

$R^3$ represents radicals of alkyl radical of 1–5 carbon atoms, cycloalkyl of 5–8 ring members or cycloalkylmethyl radical of 3–6 ring members;

$R^4$ represents benzo fused 5 to 6 ring member heteroaryl or benzo fused 5 to 6 ring member heterocyclo radicals, or a radical of the formula

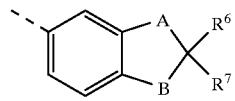

wherein A and B each independently represent O, S, SO or SO$_2$; $R^6$ represents deuterium, alkyl of 1–5 carbon atoms, fluoro or chloro radicals; $R^7$ represents hydrogen, deuterium, methyl, fluoro or chloro radicals; or a radical of the formula

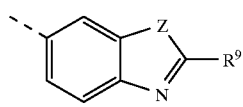

wherein Z represents O, S or NH; and $R^9$ represents a radical of formula

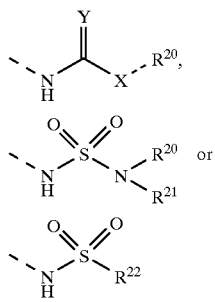

wherein Y represents O, S or NH; X represents a bond, O or $NR^{21}$;

$R^{20}$ represents hydrogen, alkyl of 1 to 5 carbon atoms, alkenyl of 2 to 5 carbon atoms, alkynyl of 2 to 5 carbon atoms, aralkyl of 1 to 5 alkyl carbon atoms, heteroaralkyl of 5 to 6 ring members and 1 to 5 alkyl carbon atoms, heterocycloalkyl of 5 to 6 ring members and 1 to 5 alkyl carbon atoms, aminoalkyl of 2 to 5 carbon atoms, N-mono-substituted or N,N-disubstituted aminoalkyl of 2 to 5 alkyl carbon atoms wherein said substituents are radicals of alkyl of 1 to 3 carbon atoms, aralkyl of 1 to 3 alkyl carbon atoms radicals, carboxyalkyl of 1 to 5 carbon atoms, alkoxycarbonylalkyl of 1 to 5 alkyl carbon atoms, cyanoalkyl of 1 to 5 carbon atoms or hydroxyalkyl of 2 to 5 carbon atoms;

$R^{21}$ represents hydrogen radical or alkyl radical of 1 to 3 carbon atoms; or the radical of formula —$NR^{20}R^{21}$ represents a 5 to 6 ring member heterocyclo radical; and $R^{22}$ represents alkyl radical of 1 to 3 carbon atoms or $R^{20}R^{21}$N-alkyl radical of 1 to 3 alkyl carbon atoms; and $R^5$ represents an alkyl radical of 1–5 carbon atoms, alkenyl radical of 2–5 carbon atoms, alkynyl radical of 2–5 carbon atoms or aryl substituted alkyl radical of 1–5 carbon atoms.

2. Compound of claim 1, or a pharmaceutically acceptable salt, prodrug or ester thereof, wherein n represents 1;

t represents 1 or 2;

$R^1$ represents hydrogen radical, alkyl radical of 1–3 carbon atoms, alkenyl radical of 2–3 carbon atoms, alkynyl radical of 2–3 carbon atoms radicals or cyanomethyl;

$R^2$ represents radicals of alkyl of 3–5 carbon atoms, arylmethyl, alkylthioalkyl of 1–3 alkyl carbon atoms, arylthiomethyl or cycloalkylmethyl of 5–6 ring member carbon atoms radicals;

$R^3$ represents alkyl of 1–5 carbon atoms, cycloalkylmethyl of 3–6 ring members, cyclohexyl or cycloheptyl radicals;

$R^4$ represents 2-amino-benzothiazol-5-yl, 2-amino-benzothiazol-6-yl, benzothiazol-5-yl, benzothiazol-6-yl, benzoxazol-5-yl, 2,3-dihydrobenzofuran-5-yl, benzofuran-5-yl, 1,3-benzodioxol-5-yl or 1,4-benzodioxan-6-yl radicals; or a radical of the formula

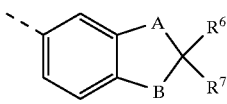

wherein A and B each represent O; $R^6$ represents deuterium, methyl, ethyl, propyl, isopropyl or fluoro radicals; and $R^7$ represents hydrogen, deuterium, methyl or fluoro radicals; or a radical of the formula

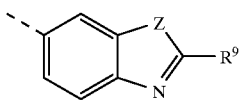

wherein Z represents O, S or NH; and $R^9$ represents a radical of formula

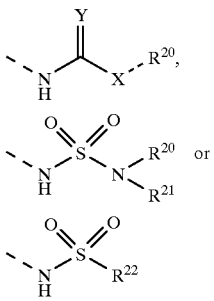

wherein Y represents O, S or NH; X represents a bond, O or $NR^{21}$;

$R^{20}$ represents hydrogen, alkyl of 1 to 5 carbon atoms, phenylalkyl of 1 to 3 alkyl carbon atoms, heterocycloalkyl of 5 to 6 ring members and 1 to 3 alkyl carbon atoms, or N-mono-substituted or N,N-disubstituted aminoalkyl of 2 to 3 alkyl carbon atoms wherein said substituents are alkyl radicals of 1 to 3 carbon atoms; and $R^{21}$ represents hydrogen or methyl radicals; or the radical of formula —$NR^{20}R^{21}$ represents pyrrolidinyl, piperidinyl, piperazinyl, 4-methylpiperazinyl, 4-benzylpiperazinyl, morpholinyl or thiamorpholinyl radicals; and $R^{22}$ represents alkyl radical of 1 to 3 carbon atoms; and $R^5$ represents an alkyl radical of 1–5 carbon atoms, alkenyl radical of 3–4 carbon atoms, alkynyl radical of 3–4 carbon atoms or aryl substituted alkyl radical of 1–4 carbon atoms.

3. Compound of claim 2, or a pharmaceutically acceptable salt, prodrug or ester thereof, wherein $R^1$ represents hydrogen, methyl, ethyl or cyanomethyl radicals;

$R^2$ represents isobutyl, n-butyl, $CH_3SCH_2CH_2$—, phenylthiomethyl, (2-naphthylthio)methyl, benzyl, 4-methoxyphenylmethyl, 4-hydroxyphenylmethyl, 4-fluorophenylmethyl or cyclohexylmethyl radicals;

$R^3$ represents propyl, isoamyl, isobutyl, butyl, cyclohexyl, cycloheptyl, cyclopentylmethyl or cyclohexylmethyl radicals; and $R^4$ represents benzothiazol-5-yl, benzothiazol-6-yl, benzoxazol-5-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl or 1,4-benzodioxan-6-yl radicals; or a radical of the formula

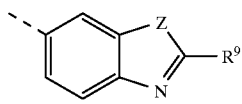

wherein Z represents O, S or NH; and $R^9$ represents a radical of formula

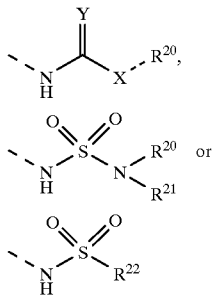

wherein Y represents O, S or NH; X represents a bond, O or $NR^{21}$;

$R^{20}$ represents hydrogen, methyl, ethyl, propyl, isopropyl, isobutyl, benzyl, 2-(1-pyrrolidinyl)ethyl, 2-(1-piperidinyl)ethyl, 2-(1-piperazinyl)ethyl, 2-(4-methylpiperazin-1-yl)ethyl, 2-(1-morpholinyl)ethyl, 2-(1-thiamorpholinyl)ethyl or 2-(N,N-dimethylamino) ethyl radicals;

$R^{21}$ represents a hydrogen radical; and $R^{22}$ represents methyl radical; and $R^5$ represents an alkyl radical of 1–5 carbon atoms or phenyl substituted alkyl radical of 2–4 carbon atoms.

4. Compound of claim 3 or a pharmaceutically acceptable salt, prodrug or ester thereof, wherein $R^1$ represents methyl or ethyl radicals;

$R^2$ represents benzyl, 4-fluorophenylmethyl or cyclohexylmethyl radicals;

$R^4$ represents benzothiazol-5-yl, benzothiazol-6-yl, 2,3-dihydrobenzofuran-5-yl, benzofuran-5-yl, 1,3-benzodioxol-5-yl, 2-methyl-1,3-benzodioxol-5-yl, 2,2-dimethyl-1,3-benzodioxol-5-yl, 2,2-dideutero-1,3-benzodioxol-5-yl, 2,2-difluoro-1,3-benzodioxol-5-yl, 1,4-benzodioxan-6-yl, 2-(methoxycarbonylamino) benzothiazol-6-yl or 2-(methoxycarbonylamino) benzimidazol-5-yl radicals; and $R^5$ represents methyl, ethyl, propyl, isopropyl or 2-phenylethyl radicals.

5. Composition comprising a compound of claim 1 and a pharmaceutically acceptable carrier.

6. Method of inhibiting a retroviral protease comprising administering an effective amount of a compound of claim 1.

7. Method of treating a retroviral infection comprising administering an effective amount of a composition of claim 5.

8. Method of inhibiting replication of a retrovirus comprising administering an effective amount of a compound of claim 1.

9. Method of preventing replication of a retrovirus in vitro comprising administering an effective amount of a compound of claim 1.

10. Method of treating HIV infection comprising administering an effective amount of a composition of claim 5.

* * * * *

UNITED STATES PATENT AND TRADEMARK OFFICE
CERTIFICATE OF CORRECTION

PATENT NO.: 5,985,870
DATED: November 16, 1999
INVENTOR(S): GETMAN et al.

It is certified that an error appears in the above-identified patent and that said Letters Patent is hereby corrected as shown below:

In claim 1 at column 112, line 25, replace the formula therein with the following:

--

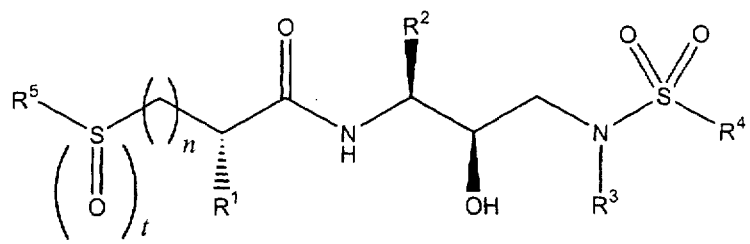

Signed and Sealed this

Third Day of April, 2001

Attest:

NICHOLAS P. GODICI

Attesting Officer

Acting Director of the United States Patent and Trademark Office